US010006097B2

(12) United States Patent
Shu et al.

(10) Patent No.: US 10,006,097 B2
(45) Date of Patent: Jun. 26, 2018

(54) COMPOSITIONS AND METHODS FOR DETECTION AND DISCRIMINATION OF INFLUENZA VIRUSES

(71) Applicant: The United States of America as represented by the Secretary of the Dept. of Health and Human Services, Washington, DC (US)

(72) Inventors: Bo Shu, Lilburn, GA (US); Stephen Lindstrom, Atlanta, GA (US); Kai-Hui Wu, Atlanta, GA (US); LaShondra Berman, Decatur, GA (US); Shannon L. Emery, Atlanta, GA (US); Christine Warnes, Alpharetta, GA (US); Catharine McCord, Denver, CO (US)

(73) Assignee: The United States of America, as represented by the Secretry, Department of Health and Human Services, Washington, DC (US)

( * ) Notice: Subject to any disclaimer, the term of this patent is extended or adjusted under 35 U.S.C. 154(b) by 0 days. days.

(21) Appl. No.: 15/030,843

(22) PCT Filed: Oct. 22, 2014

(86) PCT No.: PCT/US2014/061802
§ 371 (c)(1),
(2) Date: Apr. 20, 2016

(87) PCT Pub. No.: WO2015/061475
PCT Pub. Date: Apr. 30, 2015

(65) Prior Publication Data
US 2016/0251732 A1 Sep. 1, 2016

Related U.S. Application Data

(60) Provisional application No. 61/894,291, filed on Oct. 22, 2013.

(51) Int. Cl.
*C12Q 1/70* (2006.01)
*C07H 21/00* (2006.01)
*A61K 39/12* (2006.01)
*A61K 35/76* (2015.01)
*A61K 39/42* (2006.01)

(52) U.S. Cl.
CPC ............ *C12Q 1/701* (2013.01); *C07H 21/00* (2013.01); *C12Q 2600/16* (2013.01)

(58) Field of Classification Search
CPC ........ A61K 39/12; A61K 35/76; A61K 39/42; C12N 7/00; C12N 2830/008; C12N 2760/16151; C12N 2760/16121; C12N 2760/16221; C12N 2760/16321; C12N 2760/16021; G01N 2333/11; C12Q 1/70
See application file for complete search history.

(56) References Cited

U.S. PATENT DOCUMENTS

| 7,744,901 | B2 | 6/2010 | Yang et al. | |
| 7,972,786 | B2 | 7/2011 | Hartshorn et al. | |
| 8,097,419 | B2 | 1/2012 | Fischer et al. | |
| 8,232,058 | B2 | 7/2012 | McBride et al. | |
| 8,241,853 | B2 * | 8/2012 | Lindstrom | C12Q 1/701 435/287.2 |
| 8,389,221 | B2 | 3/2013 | Minekawa et al. | |
| 8,568,981 | B2 * | 10/2013 | Lindstrom | C12Q 1/701 435/287.2 |
| 9,382,592 | B2 * | 7/2016 | Lindstrom | C12Q 1/701 |
| 2006/0019406 | A1 * | 1/2006 | Wei | G01N 33/558 436/514 |
| 2009/0111089 | A1 * | 4/2009 | Lindstrom | C12Q 1/701 435/5 |
| 2009/0298049 | A1 * | 12/2009 | Kurnool | C12Q 1/6876 435/5 |
| 2010/0048423 | A1 * | 2/2010 | Pan | C12Q 1/701 506/16 |
| 2011/0212117 | A1 | 9/2011 | Yang et al. | |
| 2012/0283135 | A1 * | 11/2012 | Lindstrom | C12Q 1/701 506/9 |
| 2014/0094383 | A1 * | 4/2014 | Lee | G01N 33/5432 506/9 |
| 2014/0128279 | A1 * | 5/2014 | Lindstrom | C12Q 1/701 506/9 |
| 2015/0160217 | A1 * | 6/2015 | Wong | G01N 33/53 506/9 |
| 2016/0289777 | A1 * | 10/2016 | Lindstrom | C12Q 1/701 |

FOREIGN PATENT DOCUMENTS

| WO | WO 2006/098901 | 9/2006 |
| WO | WO 2007/095155 | 8/2007 |
| WO | WO 2009/151407 | 12/2009 |

OTHER PUBLICATIONS

Das et al., "Development and bench validation of real-time reverse transcription polymerase chain reaction protocols for rapid detection of the subtypes H6, H9, and H11 of avian influenza viruses in experimental samples," *J. Vet. Diagn. Invest.*, vol. 19, pp. 625-634. 2007.

(Continued)

*Primary Examiner* — Rachel B Gill
(74) *Attorney, Agent, or Firm* — Klarquist Sparkman, LLP

(57) ABSTRACT

Compositions and methods for detecting presence of an influenza virus in a sample, such as a biological sample obtained from a subject or an environmental sample, are provided. In some embodiments, the compositions and methods can be used to quickly identify particular subtypes of influenza virus (such as seasonal or variant influenza subtype H3, influenza subtype H5, Eurasian influenza subtype H7, North American influenza subtype H7, and/or influenza subtype H9) present in a sample. Probes and primers are provided herein that permit the rapid detection and/or discrimination of influenza virus subtype nucleic acids in a sample. Devices (such as arrays) and kits for detection and/or discrimination of influenza virus subtype nucleic acids are also provided.

14 Claims, 9 Drawing Sheets

(56) References Cited

OTHER PUBLICATIONS

Li et al., "Typing and Subtyping Influenza Virus Using DNA Microarrays and Multiplex Reverse Transcriptase," *Journal of Clinical Microbiology*, vol. 39, No. 2, pp. 696-704, 2001.
Monne et al. "Development and Validation of a One-Step Real-Time PCR Assay for Simultaneous Detection of Subtype H5, H7, and H9 Avian Influenza Viruses," *J. Clin. Microbiol.*, vol. 46, No. 5, pp. 1769-1773, 2008.
Spackman et al., "Development of a real-time reverse transcriptase PCR assay for Type A influenza virus and the avian H5 and H7 hemagglutinin subtypes," *Journal of Clinical Microbiology*, vol. 40, No. 9, pp. 3256-3260, 2002.
Stone et al., "Rapid detection and simultaneous subtype differentiation of influenza a viruses by real time PCR," *Journal of Virological Methods*, vol. 117, No. 2, pp. 103-112, 2004.
Ward et al., "Design and performance testing of quantitative real time PCR assays for influenza A and B viral load measurement," *Journal of Clinical Virology*, vol. 29, No. 3, pp. 179-188, 2004.

\* cited by examiner

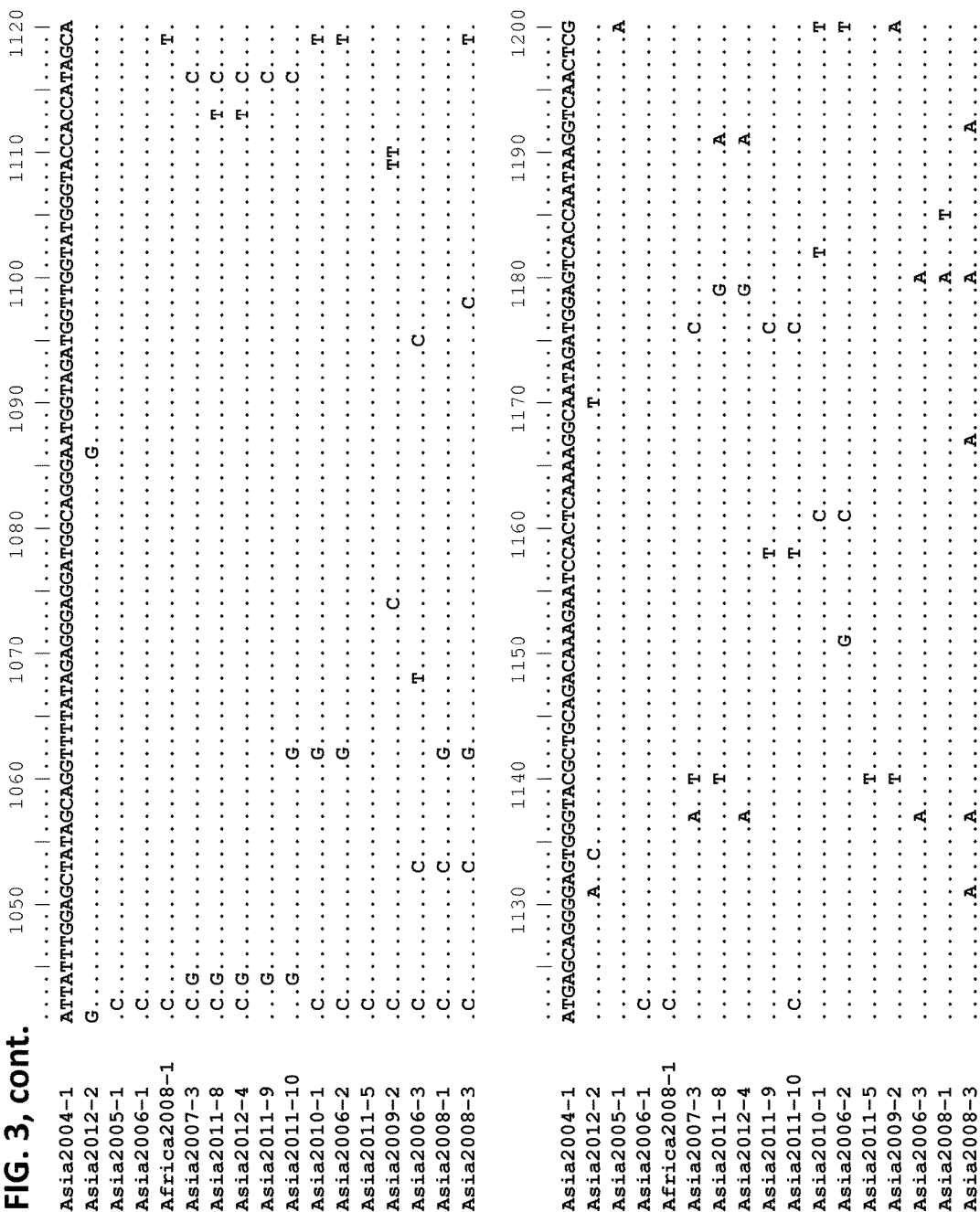
FIG. 3, cont.

FIG. 4

```
                      1050      1060      1070      1080      1090      1100      1110      1120
                 ....|....|....|....|....|....|....|....|....|....|....|....|....|....|....|....|
Asia2013-1       AGGCCTATTTGGTGCTATAGCGGGTTTCATTGAAAATGGATGGGAAGGCCTAATTGATGGTTGGTATGGTTTCAGACACC
Asia2013-2       ................................................................................
Asia2009-1       ......G........C.....A.....T........C...........T..G........A........C........T.
Africa2007-1     ...............C................................T..G.....C..G........C.....G..T.
Europe2007-1     ....................................C...........T..G.....C..G........C.....G..T.
Europe2000-1     ................................................T..G........G........C.....G..T.

1130      1140      1150      1160      1170      1180      1190      1200
                 ....|....|....|....|....|....|....|....|....|....|....|....|....|....|....|....|
Asia2013-1       AGAATGCACAGGGAGAGGGAACTGCTGCAGATTACAAAAGCACTCAATCGGCAATTGATCAAATAACAGGAAAATTAAAC
Asia2013-2       ................................................................................
Asia2009-1       .A..C.....A.....A....................G...........A.......................G.....T
Africa2007-1     .A........A..G.....G.......................C.....A..............................
Europe2007-1     ..........A..G.............................C.....A...........G........G.........
Europe2000-1     .A........A..G.............................C.....A..............................

1210      1220      1230      1240      1250      1260      1270      1280
                 ....|....|....|....|....|....|....|....|....|....|....|....|....|....|....|....|
Asia2013-1       CGGCTTATAGAAAAAACCAACCAACAATTTGAGTTGATAGACAATGAATTCAATGAGGTAGAGAAGCAAATCGGTAATGT
Asia2013-2       ....................................................C...........................
Asia2009-1       ..A..C..............T..........................G....C......T..A.....G..T..C.....
Africa2007-1     ........T........T.............................G....C......T..A........T..C.....
Europe2007-1     .................T...........C.....A.....T..........C......T..A.GA.....T..C.....
Europe2000-1     .................T.................A................C......T..A........T..C.....

1290      1300      1310      1320      1330      1340      1350      1360
                 ....|....|....|....|....|....|....|....|....|....|....|....|....|....|....|....|
Asia2013-1       GATAAATTGGACCAGAGATTCTATAACAGAAGTGTGGTCATACAATGCTGAACTCTTGGTAGCAATGGAGAACCAGCATA
Asia2013-2       ................................................................................
Asia2009-1       ..............................G..........................A....................C.
Africa2007-1     .....................C..G..............C..T..C..........................T.....C.
Europe2007-1     .....................C..G..............C..T..C..........................T.....C.
Europe2000-1     .....................C..G..............C..T..C..........................T.....C.
```

```
                   1530      1540      1550      1560      1570      1580      1590      1600
           ....|....|....|....|....|....|....|....|....|....|....|....|....|....|....|....|
Asia2011-1 AAGGCAGAAAATAGAAGGGATAAAGCTGGAGTCTGAGGGGACTTACAAAATCCTCACTATTTATTCGACTGTCGCCTCAT
Asia2012-1 G...............................................................................
Asia2009-1 ----------------...G.G..A.....A.................G........C......................
Asia2012-2 ...A...........G...G.C........A.....A..A.................C......................
Asia2009-2 ----------------...G.G..A.....A........A........G........C......................
Asia2008-1 ...A...........G...G.C........A.....A..A.................C......................
Asia2006-1 .C.................G.C.....A..A........A.......G......T..C...........C..........

1610      1620      1630      1640      1650      1660      1670
           ....|....|....|....|....|....|....|....|....|....|....|....|....|....|..
Asia2011-1 CTCTTGTACTTGCAATGGGGTTTGCTGCCTTCTTGTTCTGGGCCATGTCTAATGGATCATGCAGGTGCAACA
Asia2012-1 ........................................................................
Asia2009-1 .......G........................T..A..............C........T.....A.......
Asia2012-2 ..A....GA.........................................C.....G..T.....A.......
Asia2009-2 .......G........................T..A..............C........T.....A.......
Asia2008-1 .......GA.........................................C.....G.---------------
Asia2006-1 .......G........A.................A...............C.....G..T.............
```

COMPOSITIONS AND METHODS FOR DETECTION AND DISCRIMINATION OF INFLUENZA VIRUSES

CROSS REFERENCE TO RELATED APPLICATION

This is the § 371 U.S. National Stage of International Application No. PCT/US2014/061802, filed Oct. 22, 2014, which was published in English under PCT Article 21(2), which in turn claims the benefit of U.S. Provisional Application No. 61/894,291, filed Oct. 22, 2013, which is incorporated herein by reference in its entirety.

FIELD

This disclosure relates to probes and primers for detecting one or more subtypes of influenza virus and methods of using the probes and primers.

BACKGROUND

Influenza virus types A and B are members of the orthomyxoviridae family of viruses that cause influenza infection. The infective potential of influenza is frequently underestimated and can result in high morbidity and mortality rates, especially in elderly persons and in high-risk patients, such as the very young and the immuno-compromised. Influenza A and B viruses primarily infect the nasopharyngeal and oropharyngeal cavities and produce highly contagious, acute respiratory disease that results in significant morbidity and economic costs. Typical influenza viral infections in humans have a relatively short incubation period of one to two days, with symptoms that last about a week including an abrupt onset of fever, sore throat, cough, headache, myalgia, and malaise. When a subject is infected with a highly virulent strain of influenza these symptoms can progress rapidly to pneumonia and in some circumstances death. Pandemic outbreaks of highly virulent influenza present a serious risk to human and animal health worldwide.

The immunodominant antigens present on the surface of influenza viruses are hemagglutinin (HA or H) and neuraminidase (NA or N). Genetic reassortment between human and avian or swine influenza viruses can result in a novel virus with a hemagglutinin and/or neuraminidase against which humans lack immunity. In the 20$^{th}$ century, the pandemics of 1918, 1957, and 1968 were the result of such antigenic shifts. The avian and swine influenza outbreaks of the early 21$^{st}$ century caused by H1N1pdm09, H5N1, H7N3, H7N7, H7N9, and H9N2 subtype influenza viruses, and their infection of humans, have created a new awareness of the pandemic potential of influenza viruses that circulate in domestic poultry and swine. The impact of a major influenza pandemic has been estimated to be up as many as 200,000 deaths, 730,000 hospitalizations, 42 million outpatient visits, and 50 million additional illnesses in the U.S. alone.

Thus, the need remains for tests that provide sensitive, specific detection of influenza types and subtypes in a relatively short time in order to permit rapid and effective treatment of an infected person. In addition, detection and characterization of novel viruses infecting humans and wild or domesticated animals are critical for detection and vaccination for emerging influenza viruses, including those with pandemic potential.

SUMMARY

The present disclosure relates to compositions and methods for detecting presence of an influenza virus in a sample. The disclosed compositions and methods can be used for diagnosing an influenza infection in a subject suspected of having an influenza infection by analyzing a biological specimen from a subject to detect a variety of influenza subtypes. Alternatively, the compositions and methods can be used to quickly identify particular subtypes of influenza virus (such as seasonal or variant influenza subtype H3, influenza subtype H5, influenza subtype Eurasian or North American H7 and/or influenza subtype H9) present in a sample. Probes and primers are provided herein that permit the rapid detection and/or discrimination of influenza virus subtype nucleic acids in a sample.

Disclosed herein are probes capable of hybridizing to and discriminating influenza viruses from specific subtypes. In some embodiments, the probes are between 20 and 40 nucleotides in length and are capable of hybridizing to an influenza HA nucleic acid in a subtype-specific manner. In several embodiments, the probes are between 20 and 40 nucleotides in length and include a nucleic acid sequence at least 90% identical to the nucleic acid sequence set forth as SEQ ID NO: 3, SEQ ID NO: 4, SEQ ID NO: 9, SEQ ID NO: 10, SEQ ID NO: 13, SEQ ID NO: 16, SEQ ID NO: 106, or SEQ ID NO: 109, or the reverse complement thereof. In some examples, the probe is labeled with a detectable label (such as a fluorophore and/or fluorescent quencher).

Also disclosed herein are primers capable of hybridizing to and directing amplification of an influenza nucleic acid, such as an influenza HA nucleic acid, in a subtype-specific manner. In some embodiments, the primers are between 20 and 40 nucleotides in length and include a nucleic acid sequence at least 90% identical to the nucleic acid sequence set forth as SEQ ID NO: 1, SEQ ID NO: 2, SEQ ID NO: 5, SEQ ID NO: 6, SEQ ID NO: 7, SEQ ID NO: 8, SEQ ID NO: 11, SEQ ID NO: 12, SEQ ID NO: 14, SEQ ID NO: 15, SEQ ID NO: 104, SEQ ID NO: 105, SEQ ID NO: 107, SEQ ID NO: 108, or the reverse complement thereof.

Disclosed herein are methods of detecting influenza virus nucleic acid and/or discriminating the subtype of an influenza virus nucleic acid in a sample (such as a biological sample from a subject or an environmental sample). In some embodiments, the methods include contacting a sample with one or more of the probes disclosed herein and detecting hybridization between the sample and an influenza virus nucleic acid in the sample. In some examples, detecting hybridization between the sample and the probe indicates an influenza virus infection in a subject.

In some embodiments, the disclosed methods permit detecting or discriminating presence of influenza subtype H3 (seasonal or variant), subtype H5, subtype Eurasian or North American H7, or subtype H9 in a sample, utilizing particular subtype-specific probes described herein. In some examples, detecting hybridization of a probe including the nucleic acid sequence set forth as SEQ ID NO: 3 to an influenza virus nucleic acid in the sample indicates the presence of influenza subtype seasonal H3 in the sample, detecting hybridization of a probe including the nucleic acid sequence set forth as SEQ ID NO: 4 to an influenza virus nucleic acid in the sample indicates the presence of influenza subtype variant H3 in the sample, detecting hybridization of a probe including the nucleic acid sequence set forth as SEQ ID NO: 9, SEQ ID NO: 10, or SEQ ID NO: 13 to an influenza virus nucleic acid in the sample indicates the presence of influenza subtype H5 in the sample, detecting hybridization of a probe including the nucleic acid sequence set forth as SEQ ID NO: 16 to an influenza virus nucleic acid in the sample indicates the presence of influenza subtype Eurasian H7 in the sample, detecting hybridization of a probe including the nucleic acid sequence set forth as SEQ ID NO: 106 to an influenza virus nucleic acid in the sample indicates the presence of influenza subtype North American H7 in the sample, and detecting hybridization of a probe including the nucleic acid sequence set forth as SEQ ID NO: 109 to an influenza virus nucleic acid in the sample indicates the presence of influenza subtype H9 in the sample. In some examples, the methods further include contacting the sample with one or more additional type or subtype-specific influenza virus probes, such as one or more additional probes specific for influenza type A, influenza pandemic type A, influenza type B, influenza subtype H1, influenza subtype pandemic H1, influenza subtype H3, influenza subtype H5, influenza subtype North American H7, influenza subtype Eurasian H7, or influenza subtype H9.

In some embodiments, the methods further include amplifying the influenza virus nucleic acid with at least one primer capable of hybridizing to and amplifying the influenza virus nucleic acid. In some embodiments, the methods include contacting the sample with one or more of the primers disclosed herein (such as one or more pairs of primers disclosed herein) and amplifying the influenza virus nucleic acid.

In some examples, the methods include contacting the sample with one or more influenza subtype H3 primers (for example, one or more primers set forth as SEQ ID NO: 1 or SEQ ID NO: 2), one or more influenza subtype H5 primers (for example, one or more primers set forth as SEQ ID NO: 5, SEQ ID NO: 6, SEQ ID NO: 7, SEQ ID NO: 8, SEQ ID NO: 11, or SEQ ID NO: 12), one or more influenza subtype Eurasian H7 primers (for example, one or more primers set forth as SEQ ID NO: 14 or SEQ ID NO: 15), one or more influenza subtype North American H7 primers (for example, one or more primers set forth as SEQ ID NO: 104 or SEQ ID NO: 105), and/or one or more influenza subtype H9 primers (for example, one or more primers set forth as SEQ ID NO: 107 or SEQ ID NO: 108). In additional examples, the methods further include contacting the sample with one or more additional type or subtype-specific influenza virus primers, such as one or more primers specific for influenza type A, influenza pandemic type A, influenza type B, influenza subtype H1, influenza subtype pandemic H1, influenza subtype H3, influenza subtype H5, influenza subtype North American H7, influenza subtype Eurasian H7, or influenza subtype H9.

The disclosure also includes devices (such as arrays) and kits for detecting and/or discriminating an influenza nucleic acid in a sample. In some embodiments, the devices and kits include at least one of the probes disclosed herein, for example, at least one probe including a nucleic acid sequence at least 90% identical to the nucleic acid sequence set forth as SEQ ID NO: 3, SEQ ID NO: 4, SEQ ID NO: 9, SEQ ID NO: 10, SEQ ID NO: 13, SEQ ID NO: 16, SEQ ID NO: 106, or SEQ ID NO: 109. In some examples, the disclosed kits also include one or more of the primers (such as one or more pair of primers) disclosed herein, such as one or more primers including a nucleic acid sequence at least 90% identical to the nucleic acid sequence set forth as SEQ ID NO: 1, SEQ ID NO: 2, SEQ ID NO: 5, SEQ ID NO: 6, SEQ ID NO: 7, SEQ ID NO: 8, SEQ ID NO: 11, SEQ ID NO: 12, SEQ ID NO: 14, SEQ ID NO: 15, SEQ ID NO: 104, SEQ ID NO: 105, SEQ ID NO: 107, or SEQ ID NO: 108. The disclosed devices and kits may further include one or more additional probes and/or primers for typing and/or subtyping an influenza virus nucleic acid, such as one or more probes and/or primers specific for influenza type A, influenza pandemic type A, influenza type B, influenza subtype H1, influenza subtype pandemic H1, influenza subtype H3, influenza subtype H5, influenza subtype North American H7, influenza subtype Eurasian H7, or influenza subtype H9.

The foregoing and other features of the disclosure will become more apparent from the following detailed description, which proceeds with reference to the accompanying figures.

BRIEF DESCRIPTION OF THE DRAWINGS

FIG. 1 is a sequence alignment of a portion of the HA gene from H3 seasonal and variant viruses. Viruses are designated as follows: West Virginia, A/West_Virginia/06/2011_H3v (SEQ ID NO: 17); Indiana, A/Indiana/08/2011_H3v (SEQ ID NO: 18); Wisconsin, A/Wisconsin/67/2005_vaccine seed (SEQ ID NO: 19); Brisbane, A/Brisbane/10/2007_vaccine seed (SEQ ID NO: 20); Perth, A/Perth/16/2009_vaccine seed (SEQ ID NO: 21); and Victoria, A/Victoria/361/2011 vaccine seed (SEQ ID NO: 22). Dots indicate that the sequence is identical to that of the West Virginia virus sequence.

FIG. 2 is a series of panels showing sequence alignment of a portion of the HA gene from H5 influenza viruses. Viruses are designated as follows: Asia2004-1 (SEQ ID NO: 53); Asia2011-1 (SEQ ID NO: 54); Asia2005-1 (SEQ ID NO: 55); Asia2011-2 (SEQ ID NO: 56); Asia2011-3 (SEQ ID NO: 57); Asia2006-1 (SEQ ID NO: 58); Africa2008-1 (SEQ ID NO: 59); Asia2007-3 (SEQ ID NO: 60); Asia2011-8 (SEQ ID NO: 61); Asia2012-4 (SEQ ID NO: 62); Asia2011-9 (SEQ ID NO: 63); Asia2011-10 (SEQ ID NO: 64); Asia2010-1 (SEQ ID NO: 65); Asia2006-2 (SEQ ID NO: 66); Asia2008-1 (SEQ ID NO: 67); Asia2007-2 (SEQ ID NO: 68); Asia2011-4 (SEQ ID NO: 69); Asia2011-5 (SEQ ID NO: 70); Asia2009-2 (SEQ ID NO: 71); Asia2006-3 (SEQ ID NO: 72); Asia2008-1 (SEQ ID NO: 73); and Asia2008-3 (SEQ ID NO: 74). Dots indicate that the sequence is identical to that of the Asia2004-1 virus.

FIG. 4 is a sequence alignment of a portion of the HA gene from Eurasian H7 influenza viruses. Viruses are designated as follows: Asia2013-1_H7N9 (SEQ ID NO: 23); Asia2013-2_H7N9 (SEQ ID NO: 24), Asia2009-1_H7N3 (SEQ ID NO: 25); Africa2007-1_H7N3 (SEQ ID NO: 26); Europe2007-1_H7N3 (SEQ ID NO: 27); and Europe2000-1_H7N3 (SEQ ID NO: 28). Dots indicate that the sequence is identical to that of the Asia2013-1_H7N9 virus sequence.

Figure 5:
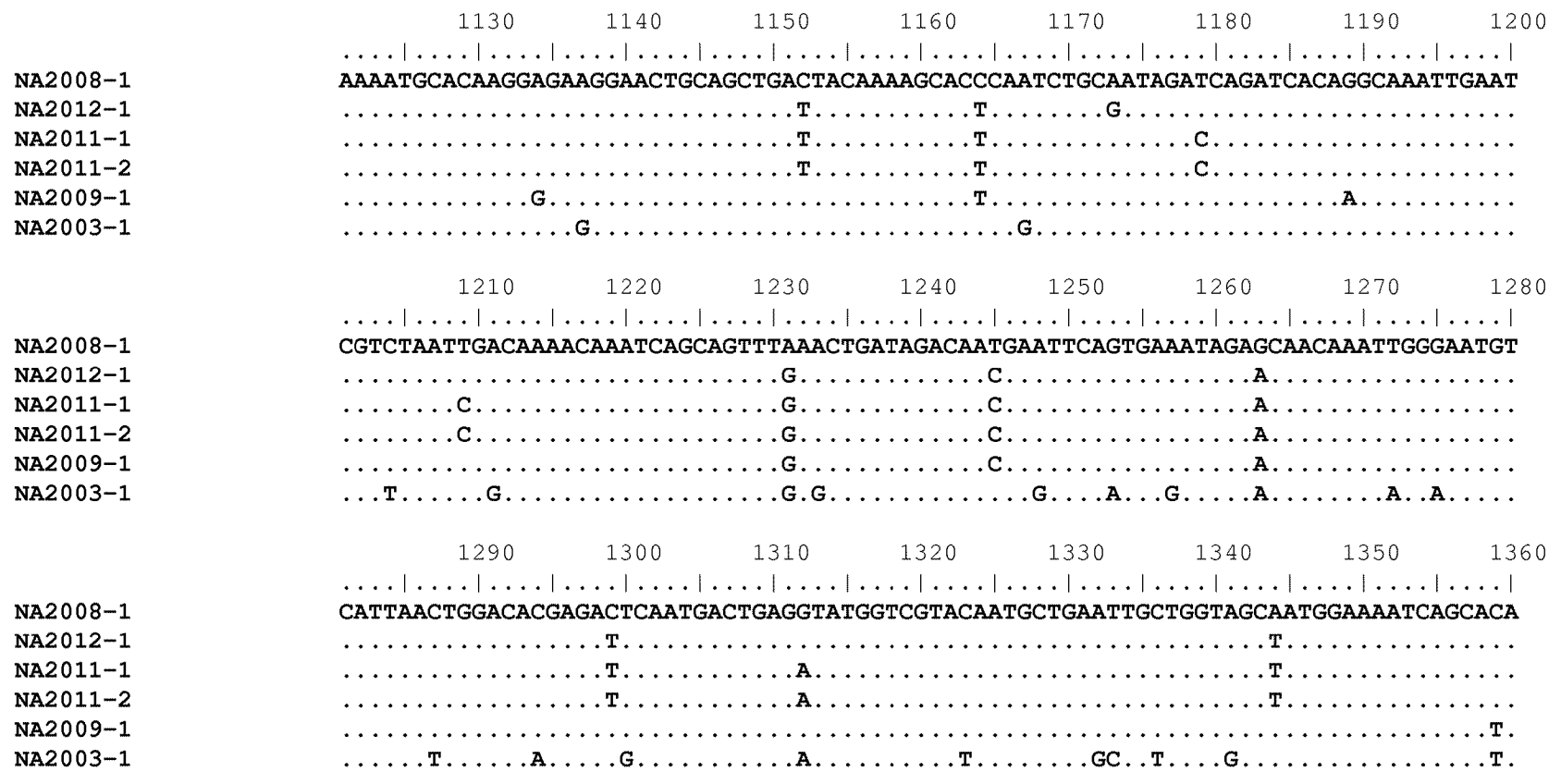

FIG. 5 is a sequence alignment of a portion of the HA gene from North American H7 influenza viruses. Viruses are designated as follows: North America 2008-1_H7N3 (SEQ ID NO: 110); North America 2012-1_H7N3 (SEQ ID NO: 111); North America 2011-1_H7N9 (SEQ ID NO: 112); North America 2011-2_H7N9 (SEQ ID NO: 113); North America 2009-1_H7N9 (SEQ ID NO: 114); and North America 2003-1_H7N2 (SEQ ID NO: 115). Dots indicate that the sequence is identical to that of the 2008-1_H7N3 virus sequence.

FIG. 6 is a sequence alignment of a portion of the HA gene from H9 influenza viruses. Viruses are designated as follows: Asia2011-1_H9N2 (SEQ ID NO: 116); Asia2012-1_H9N2 (SEQ ID NO: 117); Asia2009-1_H9N2 (SEQ ID NO: 118), Asia2012-2_H9N2 (SEQ ID NO: 119); Asia2009-2_H9N2 (SEQ ID NO: 120); Asia2008-1_H9N2 (SEQ ID NO: 121); and Asia2006-1_H9N2 (SEQ ID NO: 122). Dots indicate that the sequence is identical to that of the Asia2011-1_H9N2 virus. Dashes indicate gaps introduced in the alignment.

SEQUENCE LISTING

Figure 3:
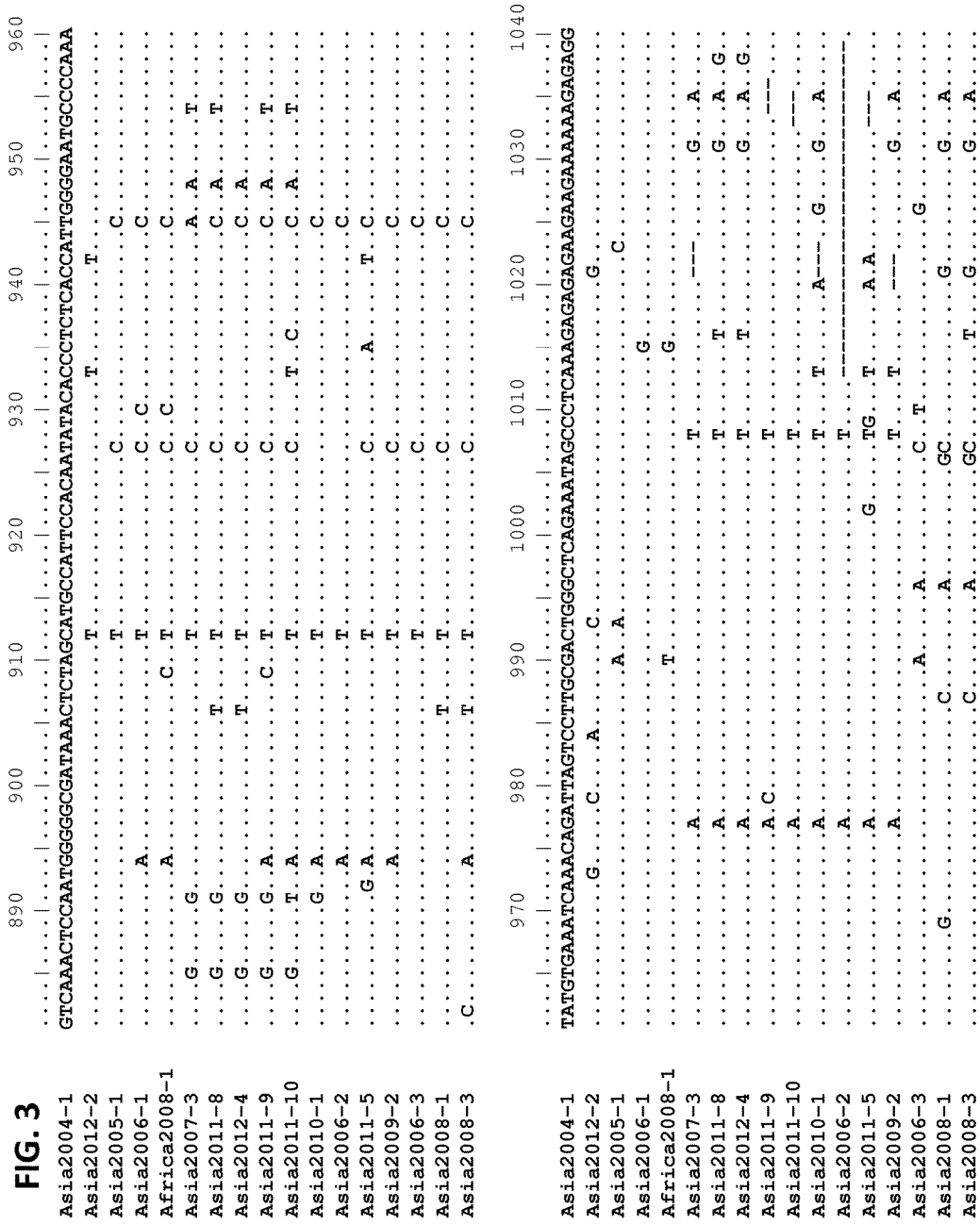
FIG. 3 is a series of panels showing sequence alignment of a portion of the HA gene from H5 influenza viruses. Viruses are designated as follows: Asia2004-1 (SEQ ID NO: 75); Asia2012-2 (SEQ ID NO: 76); Asia2005-1 (SEQ ID NO: 77); Asia2006-1 (SEQ ID NO: 78); Africa2008-1 (SEQ ID NO: 79); Asia2007-3 (SEQ ID NO: 80); Asia2011-8 (SEQ ID NO: 81); Asia2012-4 (SEQ ID NO: 82); Asia2011-9 (SEQ ID NO: 83); Asia2011-10 (SEQ ID NO: 84); Asia2010-1 (SEQ ID NO: 85); Asia2006-2 (SEQ ID NO: 86); Asia2011-5 (SEQ ID NO: 87); Asia2009-2 (SEQ ID NO: 88); Asia2006-3 (SEQ ID NO: 89); Asia2008-1 (SEQ ID NO: 90); and Asia2008-3 (SEQ ID NO: 91). Dots indicate that the sequence is identical to that of the Asia2004-1 virus. Dashes indicate gaps introduced in the alignment.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Apr. 16, 2016, and is 41,335 bytes, which is incorporated by reference herein.

SEQ ID NOs: 1 and 2 are nucleic acid sequences of influenza subtype H3 forward and reverse primers, respectively.

SEQ ID NO: 3 is the nucleic acid sequence of an influenza subtype seasonal H3 probe.

SEQ ID NO: 4 is the nucleic acid sequence of an influenza subtype variant H3 probe.

SEQ ID NOs: 5 and 6 are the nucleic acid sequences of two influenza subtype H5 assay A (H5a) forward primers.

SEQ ID NOs: 7 and 8 are the nucleic acid sequences of two influenza subtype H5 assay A (H5a) reverse primers.

SEQ ID NOs: 9 and 10 are the nucleic acid sequences of two influenza subtype H5 assay A (H5a) probes.

SEQ ID NOs: 11 and 12 are the nucleic acid sequences of influenza subtype H5 assay B (H5b) forward and reverse primers, respectively.

SEQ ID NO: 13 is the nucleic acid sequence of an influenza subtype H5 assay B (H5b) probe.

SEQ ID NOs: 14 and 15 are nucleic acid sequences of influenza subtype Eurasian H7 forward and reverse primers, respectively.

SEQ ID NO: 16 is the nucleic acid sequence of an influenza subtype Eurasian H7 probe.

SEQ ID NOs: 17 and 18 are nucleic acid sequences of a portion of the HA gene of two influenza subtype variant H3 viruses.

SEQ ID NOs: 19-22 are nucleic acid sequences of a portion of the HA gene of four influenza subtype H3 vaccine seed viruses.

SEQ ID NOs: 23-28 are nucleic acid sequences of a portion of the HA gene of six influenza subtype Eurasian H7 viruses.

SEQ ID NO: 29 is the nucleic acid sequence of a prior influenza type A probe.

SEQ ID NO: 30 is the nucleic acid sequence of an influenza pandemic type A probe.

SEQ ID NO: 31 is the nucleic acid sequence of an influenza type B probe.

SEQ ID NO: 32 is the nucleic acid sequence of an influenza subtype H1 probe.

SEQ ID NO: 33 is the nucleic acid sequence of an influenza pandemic subtype H1 probe.

SEQ ID NO: 34 is the nucleic acid sequence of a prior influenza subtype North American H7 probe.

SEQ ID NO: 35 is the nucleic acid sequence of a prior influenza subtype H9 probe.

SEQ ID NO: 36 is the nucleic acid sequence of a human RNase P probe.

SEQ ID NOs: 37 and 38 are nucleic acid sequences of prior influenza type A forward and reverse primers, respectively.

SEQ ID NOs: 39 and 40 are nucleic acid sequences of influenza pandemic type A forward and reverse primers, respectively.

SEQ ID NOs: 41 and 42 are nucleic acid sequences of influenza type B forward and reverse primers, respectively.

SEQ ID NOs: 43 and 44 are nucleic acid sequences of influenza subtype H1 forward and reverse primers, respectively.

SEQ ID NOs: 45 and 46 are nucleic acid sequences of influenza subtype pandemic H1 forward and reverse primers, respectively.

SEQ ID NOs: 47 and 48 are nucleic acid sequences of prior influenza subtype North American H7 forward and reverse primers, respectively.

SEQ ID NOs: 49 and 50 are nucleic acid sequences of prior influenza subtype H9 forward and reverse primers, respectively.

SEQ ID NOs: 51 and 52 are nucleic acid sequences of human RNase P forward and reverse primers, respectively.

SEQ ID NOs: 53-91 are nucleic acid sequences of a portion of the HA gene of influenza subtype H5 viruses.

SEQ ID NOs: 92-94 are nucleic acid sequences of a prior influenza subtype H3 forward primer, reverse primer, and probe, respectively.

SEQ ID NOs: 95-97 are nucleic acid sequences of prior influenza subtype H5 assay A (H5a) forward primer, reverse primer, and probe, respectively.

SEQ ID NOs: 98-100 are nucleic acid sequences of prior influenza subtype H5 assay B (H5b) forward primer, reverse primer, and probe, respectively.

SEQ ID NOs: 101-103 are nucleic acid sequences of prior influenza subtype Eurasian H7 forward primer, reverse primer, and probe, respectively.

SEQ ID NOs: 104 and 105 are nucleic acid sequences of influenza subtype North American H7 forward and reverse primers, respectively.

SEQ ID NO: 106 is the nucleic acid sequence of an influenza subtype North American H7 probe.

SEQ ID NOs: 107 and 108 are nucleic acid sequences of influenza subtype H9 forward and reverse primers, respectively.

SEQ ID NO: 109 is the nucleic acid sequence of an influenza subtype H9 probe.

SEQ ID NOs: 110-1115 are nucleic acid sequences of a portion of the HA gene of influenza subtype North American H7 viruses.

SEQ ID NOs: 116-122 are nucleic acid sequences of a portion of the HA gene of influenza subtype H9 viruses.

DETAILED DESCRIPTION

I. Abbreviations

FAM 6-carboxyfluorescein
FRET fluorescence resonance energy transfer

HA hemagglutinin gene or protein
LOD limit of detection
M matrix gene or protein
NA neuraminidase gene or protein
NP nucleoprotein gene or protein
PCR polymerase chain reaction
RT-PCR reverse transcription-polymerase chain reaction
rRT-PCR real-time reverse transcription-polymerase chain reaction

II. Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe." As used herein, the term "comprises" means "includes." Thus, "comprising a probe" means "including a probe" without excluding other elements. It is further to be understood that all base sizes or amino acid sizes, and all molecular weight or molecular mass values, given for nucleic acids or polypeptides are approximate, and are provided for descriptive purposes, unless otherwise indicated.

All publications, patent applications, patents, and other references mentioned herein are incorporated by reference in their entirety for all purposes. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the disclosure, the following explanations of terms are provided:

Amplification:

To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR; real-time reverse transcriptase PCR (rt RT-PCR or rRT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134); amongst others.

Complementary:

A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Detect:

To determine if an agent (such as a signal or particular nucleotide(s) or amino acid(s)) is present or absent. In some examples, this can further include quantification. Use of the disclosed probes in particular examples permits detection of a fluorophore, for example detection of a signal from an acceptor fluorophore, which can be used to determine if a nucleic acid corresponding to nucleic acid of an influenza virus is present.

Fluorophore:

A chemical compound, which when excited by exposure to a particular stimulus such as a defined wavelength of light, emits light (fluoresces), for example at a different wavelength (such as a longer wavelength of light). Examples of particular fluorophores that can be used in the probes are disclosed herein.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to a nucleic acid molecule.

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET):

A spectroscopic process by which energy is passed between an initially excited donor to an acceptor molecule usually separated by about 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule.

Examples of oligonucleotides using FRET that can be used to detect amplicons include linear oligoprobes (such as HybProbes), 5' nuclease (or hydrolysis) oligoprobes (such as TAQMAN® probes), hairpin oligoprobes (such as molecular beacons, scorpion primers, UniPrimers, and sunrise primers) and minor groove binding probes.

Hybridization:

The ability of complementary single-stranded DNA or RNA to form a duplex molecule (also referred to as a hybridization complex). Nucleic acid hybridization techniques can be used to form hybridization complexes between a probe or primer and a nucleic acid, such as an influenza nucleic acid. For example, a probe or primer having some identity to an influenza nucleic acid molecule will form a hybridization complex with an influenza nucleic acid molecule.

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)

Hybridization: 5×SSC at 65° C. for 16 hours
Wash twice: 2×SSC at room temperature (RT) for 15 minutes each
Wash twice: 0.5×SSC at 65° C. for 20 minutes each High Stringency (Detects Sequences that Share at Least 80% Identity)

Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each Low Stringency (Detects Sequences that Share at Least 50% Identity)

Hybridization: 6×SSC at RT to 55° C. for 16-20 hours
Wash at least twice: 2×-3×SSC at RT to 55° C. for 20-30 minutes each The probes and primers disclosed herein are capable of hybridizing to influenza nucleic acids under low stringency, high stringency, and very high stringency conditions.

Influenza Virus:

Influenza viruses are enveloped negative-strand viruses belonging to the orthomyxoviridae family. Influenza viruses are classified on the basis of their core proteins into three distinct types: A, B, and C. Within these broad classifications, subtypes are further divided based on the characterization of two antigenic surface proteins hemagglutinin (HA or H) and neuraminidase (NA or N). While B and C type influenza viruses are largely restricted to humans, influenza A viruses are pathogens of a wide variety of species including humans, non-human mammals, and birds. Periodically, non-human strains, particularly of swine and avian influenza, have infected human populations, in some cases causing severe disease with high mortality. Reassortment between such swine or avian strains and human strains in co-infected individuals has given rise to reassortant influenza viruses to which immunity is lacking in the human population, resulting in influenza pandemics. Four such pandemics occurred during the past century (pandemics of 1918, 1957, 1968, and 2009) and resulted in numerous deaths worldwide.

Influenza viruses have a segmented single-stranded (negative or antisense) genome. The influenza virion consists of an internal ribonucleoprotein core containing the single-stranded RNA genome and an outer lipoprotein envelope lined by a matrix protein. The segmented genome of influenza consists of eight linear RNA molecules that encode ten polypeptides. Two of the polypeptides, HA and NA, include the primary antigenic determinants or epitopes required for a protective immune response against influenza. Based on the antigenic characteristics of the HA and NA proteins, influenza strains are classified into subtypes. For example, recent outbreaks of avian influenza in Asia have been categorized as H1N1, H5N1, H7N3, H7N9, and H9N2 based on their HA and NA phenotypes.

HA is a surface glycoprotein which projects from the lipoprotein envelope and mediates attachment to and entry into cells. The HA protein is approximately 566 amino acids in length, and is encoded by an approximately 1780 base polynucleotide sequence of segment 4 of the genome. Nucleotide and amino acid sequences of HA (and other influenza antigens) isolated from recent, as well as historic, avian influenza strains can be found, for example in the GenBank database (available on the world wide web at ncbi.nlm.nih.gov/entrez) or the Influenza Research Database (available on the world wide web at fludb.org). For example, H1 subtype HA sequences include GenBank Accession Nos. AY038014, J02144, JF915184 and GQ334330; H3 subtype HA sequences include GenBank Accession Nos. AY531037, M29257, and U97740; H5 subtype HA sequences include GenBank Accession Nos. AY075033, AY075030, AY818135, AF046097, AF046096, and AF046088; H7 subtype HA sequences include GenBank Accession Nos. AJ704813, AJ704812, and Z47199; and H9 subtype HA sequences include GenBank Accession Nos. AY862606, AY743216, and AY664675, all of which are incorporated by reference herein as present in the GenBank database on Aug. 22, 2013. One of ordinary skill in the art can identify additional HA nucleic acid sequences, including those now known or identified in the future.

In addition to the HA antigen, which is the predominant target of neutralizing antibodies against influenza, the neuraminidase (NA) envelope glycoprotein is also a target of the protective immune response against influenza. NA is an approximately 450 amino acid protein encoded by an approximately 1410 nucleotide sequence of influenza genome segment 6. Recent pathogenic avian strains of influenza have belonged to the N1, N2, N3, and N9 subtypes. Exemplary NA nucleotides include for example, N1: GenBank Accession Nos. AY651442, AY651447, and AY651483; N7: GenBank Accession Nos. AY340077, AY340078 and AY340079; N2: GenBank Accession Nos. AY664713, AF508892, and AF508588; N3: GenBank Accession Nos. CY035841, CY125730, and JQ906581; and N9: GenBank Accession Nos. KC853765, KF239720, and CY147190; all of which are incorporated by reference herein as present in the GenBank database on Aug. 22, 2013. One of ordinary skill in the art can identify additional NA nucleic acid sequences, including those now known or identified in the future.

The remaining segments of the influenza genome encode the internal proteins. PB2 is a 759 amino acid polypeptide which is one of the three proteins which comprise the RNA-dependent RNA polymerase complex. PB2 is encoded by approximately 2340 nucleotides of the influenza genome segment 1. The remaining two polymerase proteins, PB1, a 757 amino acid polypeptide, and PA, a 716 amino acid polypeptide, are encoded by a 2341 nucleotide sequence and a 2233 nucleotide sequence (and 3), respectively.

Segment 5 consists of about 1565 nucleotides encoding an about 498 amino acid nucleoprotein (NP) protein that forms the nucleocapsid. Segment 7 consists of an about 1027 nucleotide sequence of the M gene, which encodes the two matrix (M) proteins; an about 252 amino acid M1 protein, and an about 96 amino acid M2 protein, which is translated from a spliced variant of the M RNA. Segment 8 consists of the NS gene, which encodes two different non-structural proteins, NS1 and NS2.

Isolated:

An "isolated" biological component (such as a nucleic acid) has been substantially separated or purified away from other biological components in which the component naturally occurs, such as other chromosomal and extrachromosomal DNA, RNA, and proteins. Nucleic acids that have been "isolated" include nucleic acids purified by standard purification methods. The term also embraces nucleic acids prepared by recombinant expression in a host cell as well as chemically synthesized nucleic acids, such as probes and primers. Isolated does not require absolute purity, and can include nucleic acid molecules that are at least 50% isolated, such as at least 75%, 80%, 90%, 95%, 98%, 99% or even 100% isolated.

Label or Detectable Label:

An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Limit of Detection (LOD):

The lowest analyte concentration that can be reliably (for example, reproducibly) detected for a given type of sample and/or assay method. In some examples, LOD is determined by testing serial dilutions of a sample known to contain the analyte and determining the lowest dilution at which detection occurs. In some examples, the LOD for an influenza virus assay (such as those described herein) is expressed as level of infectivity (for example, 50% tissue culture infective dose/ml ($TCID_{50}$/ml) or 50% embryo (or egg) infective dose/ml ($EID_{50}$/ml), expressed as a $log_{10}$ scale) or RNA copy number/μl that can be detected. One of skill in the art can determine the LOD for a particular assay and/or sample type using conventional methods.

Primers:

Short nucleic acid molecules, such as a DNA oligonucleotide, for example sequences of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of an influenza nucleic acid), wherein the sequence of the primer is specific for the target nucleic acid molecule, for example so that the primer will hybridize to the target nucleic acid molecule under high or very high stringency hybridization conditions.

In particular examples, a primer is at least 15 nucleotides in length, such as at least 15 contiguous nucleotides complementary to a target nucleic acid molecule. Particular lengths of primers that can be used to practice the methods of the present disclosure (for example, to amplify a region of an influenza nucleic acid) include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, 20-40 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer3 (world wide web at flypush.imgen.bcm.tmc.edu/primer/primer3_www.cgi).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe:

A probe comprises an isolated nucleic acid capable of hybridizing to a target nucleic acid (such as an influenza nucleic acid). A detectable label or reporter molecule can be attached to a probe. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 20 nucleotides in length, such as at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 20-60 nucleotides, 20-50 nucleotides, 20-40 nucleotides, or 20-30 nucleotides.

Quantitating a Nucleic Acid Molecule:

Determining or measuring a quantity (such as an absolute or a relative quantity) of nucleic acid molecules present, such as the number of amplicons or the number of nucleic acid molecules present in a sample. In particular examples, it is determining the relative amount or actual number of nucleic acid molecules present in a sample.

Quenching of Fluorescence:

A reduction of fluorescence. For example, quenching of a fluorophore's fluorescence occurs when a quencher molecule (such as the fluorescence quenchers disclosed herein) is present in sufficient proximity to the fluorophore that it reduces the fluorescence signal (for example, prior to the binding of a probe to an influenza nucleic acid sequence, when the probe contains a fluorophore and a quencher).

Real-Time PCR:

A method for detecting and measuring products generated during each cycle of a PCR, which are proportionate to the amount of template nucleic acid prior to the start of PCR. The information obtained, such as an amplification curve, can be used to determine the presence of a target nucleic acid (such as an influenza nucleic acid) and/or quantitate the initial amounts of a target nucleic acid sequence. In some examples, real time PCR is real time reverse transcriptase PCR (rRT-PCR).

In some examples, the amount of amplified target nucleic acid (such as an influenza nucleic acid) is detected using a labeled probe, such as a probe labeled with a fluorophore, for example a TAQMAN® probe. In this example, the increase in fluorescence emission is measured in real time, during the course of the RT-PCR. This increase in fluorescence emission is directly related to the increase in target nucleic acid amplification (such as influenza nucleic acid amplification). In some examples, the change in fluorescence (dRn) is calculated using the equation $dRn = Rn^+ - Rn^-$, with $Rn^+$ being the fluorescence emission of the product at each time point and $Rn^-$ being the fluorescence emission of the baseline. The dRn values are plotted against cycle number, resulting in amplification plots. The threshold value (Ct) is the PCR cycle number at which the fluorescence emission (dRn) exceeds a chosen threshold, which is typically 10 times the standard deviation of the baseline (this threshold level can, however, be changed if desired).

Sample:

As used herein, a sample (for example a biological sample) includes all clinical samples useful for detecting influenza virus in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin, and/or embedded in paraffin; autopsy material; tears; milk; skin scrapes; surface washings; urine; sputum; cerebrospinal fluid; prostate fluid; pus; bone marrow aspirates; middle ear fluids; bronchoalveolar lavage; tracheal aspirates; nasopharyngeal aspirates or swabs; oropharyngeal aspirates or swabs; or saliva. Samples also include environmental samples, for example, food, water (such as water from cooling towers, central air conditioning systems, swimming pools, domestic water systems, fountains, or freshwater creeks or ponds), surface swabs (for example, a swab of a counter, bed, floor, wall, or other surface), or other materials that may contain or be contaminated with influenza virus.

Sensitivity and Specificity:

Statistical measurements of the performance of a binary classification test. Sensitivity measures the proportion of actual positives which are correctly identified (e.g., the percentage of samples that are identified as including nucleic acid from a particular organism). Specificity measures the proportion of negatives which are correctly identified (e.g., the percentage of samples that are identified as not including nucleic acid from a particular organism).

Sequence Identity/Similarity:

Sequence identity between two or more nucleic acid or amino acid sequences can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 90%, at least 95%, at least 96%, at least 97%, at least 98%, or at least 99% sequence identity to any of SEQ ID NOS: 1-16 or 104-109 are provided herein. One of ordinary skill in the art will appreciate that these sequence identity ranges are provided for guidance only; it is possible that probes and primer can be used that fall outside these ranges.

Signal:

A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Subject:

A living multi-cellular vertebrate organism, a category that includes human and non-human mammals and birds.

TAQMAN® Probes:

A linear oligonucleotide probe with a 5' reporter fluorophore (for example, 6-carboxyfluorescein (FAM)) and an internal or 3' quencher fluorophore, (for example, BLACK-HOLE QUENCHER™ 1 (BHQ™ 1)). In the intact TAQ-MAN® probe, energy is transferred (via FRET) from the short-wavelength fluorophore to the long-wavelength fluorophore, quenching the short-wavelength fluorescence. After hybridization, the probe is susceptible to degradation by the endonuclease activity of a processing Taq polymerase. Upon degradation, FRET is interrupted, increasing the fluorescence from the short-wavelength fluorophore and decreasing fluorescence from the long-wavelength fluorophore.

Target Nucleic Acid Molecule:

A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule, which can include RNA (such as viral RNA) or DNA (such as DNA produced by reverse transcription of viral RNA). Purification or isolation of the target nucleic acid molecule, if needed, can be conducted by methods known to those in the art, such as by using a commercially available purification kit or the like. In one example, a target nucleic molecule is an influenza nucleic acid molecule.

III. Probes and Primers

Probes and primers capable of hybridizing to influenza virus nucleic acid and suitable for use in the disclosed methods are described herein.

A. Influenza Subtype-Specific Probes

Probes capable of hybridizing to and detecting the presence of influenza nucleic acids are disclosed. The disclosed probes are between 20 and 40 nucleotides in length, such as 20, 21, 22, 23, 24, 25, 26, 27, 28, 29, 30, 31, 32, 32, 34, 35, 36, 37, 38, 39, or 40 nucleotides in length and are capable of hybridizing to influenza virus nucleic acids. In several embodiments, a probe is capable of hybridizing under high stringency or very high stringency conditions to an influenza virus nucleic acid such as an HA nucleic acid, for example an influenza subtype seasonal H3 HA nucleic acid (for example, nucleic acids set forth as SEQ ID NOs: 19-22), an influenza subtype variant H3 HA nucleic acid (for example, nucleic acids set forth as SEQ ID NO: 17 or SEQ ID NO: 18), an influenza subtype H5 HA nucleic acid (for example, nucleic acids set forth as SEQ ID NOs: 53-91), an influenza subtype Eurasian H7 HA nucleic acid (for example, nucleic acids set forth as SEQ ID NOs: 23-28), an influenza subtype North American H7 HA nucleic acid (for example, nucleic acids set forth as SEQ ID NOs: 110-115), or an influenza subtype H9 HA nucleic acid (for example, nucleic acids set forth as SEQ ID NOs: 116-122).

In several embodiments, a probe capable of hybridizing to an influenza nucleic acid contains a nucleic acid sequence that is at least 90% identical, such as at least 91%, at least 92%, at least 93%, at least 94%, at least 95%, at least 96%, at least 97%, at least 98%, at least 99%, or even 100% identical to the nucleotide sequence set forth as SEQ ID NO: 3, SEQ ID NO: 4, SEQ ID NO: 9, SEQ ID NO: 10, SEQ ID NO: 13, SEQ ID NO: 16, SEQ ID NO: 106, or SEQ ID NO: 109. In several embodiments, a probe capable of hybridizing to an influenza nucleic acid consists essentially of a nucleic acid sequence set forth as SEQ ID NO: 3, SEQ ID NO: 4, SEQ ID NO: 9, SEQ ID NO: 10, SEQ ID NO: 13, SEQ ID NO: 16, SEQ ID NO: 106, or SEQ ID NO: 109.

In several embodiments, the probe is influenza subtype-specific. An influenza subtype-specific probe is capable of hybridizing under stringent conditions (such as high stringency or very high stringency conditions) to an influenza virus nucleic acid from a specific influenza subtype, such as influenza subtype H3 (seasonal or variant), H5, H7 (Eurasian or North American), or H9. Subtype-specific probes can be used to detect the presence of and/or differentiate between various influenza subtypes. Such probes are specific for one influenza subtype, for example specific for an influenza HA nucleic acid that is subtype-specific, such as a seasonal H3, variant H3, H5, Eurasian H7, North American H7, or H9 nucleic acid. Seasonal H3 influenza A viruses are routinely circulating in human (sometimes called "human influenza viruses") and are responsible for seasonal influenza epidemics each year. H3 variant influenza A viruses are normally circulating in swine populations. These are called "swine influenza viruses" when isolated from pigs, but are called "H3 variant viruses" when they are found in humans. Influenza subtype H7 viruses fall into two predominant genetic groups based on their HA gene evolution, termed North American and Eurasian H7 subtype lineages. Generally, these two lineages reflect the geographic separation of viruses circulating in avian hosts (both poultry and wild birds) primarily restricted in movement to either the Eastern or Western Hemispheres.

In some examples, a probe that is subtype-specific for (for example, hybridizes to) seasonal influenza subtype H3 is not subtype-specific for (for example, does not substantially hybridize to) variant influenza subtype H3, influenza subtype H5, influenza subtype H7 (Eurasian or North American), or influenza subtype H9. In another example, a probe that is subtype-specific for (for example, hybridizes to) variant influenza subtype H3 is not subtype-specific for (for example, does not substantially hybridize to) seasonal influenza subtype H3, influenza subtype H5, influenza subtype H7 (Eurasian or North American), or influenza subtype H9. In another example, a probe that is subtype-specific for (for example, hybridizes to) influenza subtype H5 is not subtype-specific for (for example, does not substantially hybridize to) influenza subtype H3 (seasonal or variant), influenza subtype H7 (Eurasian or North American), or influenza subtype H9. In another example, a probe that is subtype-specific for (for example, hybridizes to) influenza subtype Eurasian H7 is not subtype-specific for (for example, does not substantially hybridize to) influenza subtype H3 (seasonal or variant), influenza subtype H5, influenza subtype North American H7, or influenza subtype H9. In another example, a probe that is subtype-specific for (for example, hybridizes to) influenza subtype North American H7 is not subtype-specific for (for example, does not substantially hybridize to) influenza subtype H3 (seasonal or variant), influenza subtype H5, influenza subtype Eurasian H7, or influenza subtype H9. In a further example, a probe that is subtype-specific for (for example, hybridizes to) influenza subtype H9 is not subtype-specific for (for example, does not substantially hybridize to) influenza subtype H3 (seasonal or variant), influenza subtype H5, or influenza subtype H7 (Eurasian or North American). One of ordinary skill in the art will understand that subtype-specific probes, such as those disclosed herein are also not subtype-specific for (for example, do not hybridize to) other influenza virus subtypes, such as influenza subtype H1.

In some embodiments, the probe is specific for an influenza subtype seasonal H3 nucleic acid, such as a nucleic acid including the sequence set forth in any one of SEQ ID NOs: 19-22. In a specific example, a probe specific for an influenza subtype seasonal H3 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 3. In other embodiments, the probe is specific for an influenza subtype variant H3 sequence, such as a nucleic acid including the sequence set forth as SEQ ID NO: 17 or SEQ ID NO: 18. In a specific example, a probe specific for an influenza subtype variant H3 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 4. In further embodiments, the probe is specific for an influenza subtype H5 nucleic acid, such as a nucleic acid including the sequence set forth as SEQ ID NOs: 53-91. In a specific example, a probe specific for an influenza subtype H5 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 9, SEQ ID NO: 10, or SEQ ID NO: 13. In additional embodiments, the probe is specific for an influenza subtype Eurasian H7 nucleic acid, such as a nucleic acid including the sequence set forth as any one of SEQ ID NOs: 23, 24, 25, 26, 27, or 28. In a specific example, a probe specific for an influenza subtype Eurasian H7 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 16. In additional embodiments, the probe is specific for an influenza subtype North American H7 nucleic acid, such as a nucleic acid including the sequence set forth as any one of SEQ ID NOs: 110, 111, 112, 113, 114, or 115. In a specific example, a probe specific for an influenza subtype North American H7 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 106. In still further embodiments, the probe is specific for an influenza subtype H9 nucleic acid, such as a nucleic acid including the sequence set forth as any one of SEQ ID NOs: 116, 117, 118, 119, 120, 121, or 122. In a specific example, a probe specific for an influenza subtype H9 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 109.

In certain embodiments the probes are included a set of probes, such as one or more (for example, 1-30, 5-20, or 10-30, such as 2, 3, 4, 5, 6, 7, 8, 9 or 10) probes capable of hybridizing to an influenza nucleic acid. In some examples, the set of probes includes one or more probes that are specific for influenza subtype seasonal H3 (for example, SEQ ID NO: 3), subtype variant H3 (for example, SEQ ID NO: 4), subtype H5 (for example, SEQ ID NOs: 9, 10, or 13), subtype Eurasian H7 (for example, SEQ ID NO: 16), subtype North American H7 (for example, SEQ ID NO: 106), subtype H9 (for example, SEQ ID NO: 109), or a combination of two or more thereof (such as 2, 3, 4, 5, 6, 7 or 8 of such probes). In further examples, the set of probes also includes additional influenza type or subtype-specific probes, such as probes that are specific for one or more of influenza type A, influenza type A pandemic 2009, influenza type B, influenza subtype H1, influenza subtype H1 pandemic 2009, influenza subtype H3, influenza subtype H5, influenza subtype Eurasian H7, influenza subtype North American H7, and/or influenza subtype H9 (for example SEQ ID NO: 29, 30, 31, 32, 33, 34, 35, 94, 97, 100, or 103). In some embodiments, the set of probes further includes one or more control probes, such as a probe specific for a human nucleic acid (for example, RNase P, such as SEQ ID NO: 36).

In some embodiments, the probe is detectably labeled, either with an isotopic or non-isotopic label, or alternatively the target nucleic acid (such as an influenza nucleic acid) is labeled. Non-isotopic labels can, for instance, comprise a fluorescent or luminescent molecule, a hapten (for example, biotin), an enzyme or enzyme substrate, or a chemical. Such labels are preferentially chosen such that the hybridization of the probe with target nucleic acid (such as an influenza nucleic acid) can be detected. In some examples, the probe is labeled with a fluorophore. Examples of suitable fluorophore labels are given below. In some examples, the fluorophore is a donor fluorophore. In other examples, the fluorophore is an accepter fluorophore, such as a fluorescence quencher. In some examples, the probe includes both a donor fluorophore and an accepter fluorophore. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3' end to prevent extension of the probe by a polymerase.

In particular examples, the acceptor fluorophore (such as a fluorescence quencher) is attached to the 3' end of the probe and the donor fluorophore is attached to a 5' end of the probe. In another particular example, the acceptor fluorophore (such as a fluorescence quencher) is attached to a modified nucleotide (such as a T, for example, an internal T) and the donor fluorophore is attached to a 5' end of the probe.

In a particular example, an acceptor fluorophore is a dark quencher, such as Dabcyl, QSY7 (Molecular Probes), QSY33 (Molecular Probes), BLACK HOLE QUENCHERS™ (Glen Research), ECLIPSE™ Dark Quencher (Epoch Biosciences), or IOWA BLACK™ (Integrated DNA Technologies).

Examples of particular fluorophores that can be used in the probes disclosed herein are known to those of skill in the art and include those provided in U.S. Pat. No. 5,866,366 to Nazarenko et al., such as 4-acetamido-4'-isothiocyanatostilbene-2,2'disulfonic acid; acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; Cy5.5; Cy56-carboxyfluorescein; boron dipyrromethene difluoride (BODIPY); acridine; stilbene; Texas Red®; Cy3®; Cy5®, VIC® (Applied Biosystems); LC Red 640; LC Red 705; and Yakima yellow, amongst others.

Other suitable fluorophores include those known to those skilled in the art, for example those available from Molecular Probes (Eugene, Oreg.). In particular examples, a fluorophore is used as a donor fluorophore or as an acceptor fluorophore.

B. Primers for Amplification of Influenza Virus Nucleic Acids

Primers capable of hybridizing to and directing the amplification of influenza virus nucleic acids are disclosed. The primers disclosed herein are between 15 to 40 nucleotides in length, such as 15, 16, 17, 18, 19, 20, 21, 22, 23, 24, 25, 26, 27, 28, 29, 30, 31, 32, 33, 34, 35, 36, 37, 38, 39, or 40 nucleotides in length. In several embodiments, a primer is capable of hybridizing under high or very high stringency conditions to an influenza virus nucleic acid sequence set forth as SEQ ID NOs: 17-28, 53-91, or 110-122 and directing the amplification of the influenza nucleic acid or a portion thereof.

In several embodiments, a primer capable of hybridizing to and directing the amplification of an influenza nucleic acid contains a nucleic acid sequence that is at least 90% identical such as at least 91%, at least 92%, at least 93%, at least 94%, at least 95%, at least 96%, at least 97%, at least 98%, at least 99%, or even 100% identical to the nucleic acid sequence set forth as SEQ ID NO: 1, SEQ ID NO: 2, SEQ ID NO: 5, SEQ ID NO: 6, SEQ ID NO: 7, SEQ ID NO: 8, SEQ ID NO: 11, SEQ ID NO: 12, SEQ ID NO: 14, SEQ ID NO: 15, SEQ ID NO: 104, SEQ ID NO: 105, SEQ ID NO: 107, or SEQ ID NO: 108. In several embodiments, a primer capable of hybridizing to an influenza nucleic acid consists essentially of a nucleic acid sequence set forth as SEQ ID NO: 1, SEQ ID NO: 2, SEQ ID NO: 5, SEQ ID NO: 6, SEQ ID NO: 7, SEQ ID NO: 8, SEQ ID NO: 11, SEQ ID NO: 12, SEQ ID NO: 14, SEQ ID NO: 15, SEQ ID NO: 104, SEQ ID NO: 105, SEQ ID NO: 107, or SEQ ID NO: 108.

In several embodiments, the primer is influenza subtype-specific. An influenza subtype-specific primer is capable of hybridizing under stringent conditions (such as high stringency or very high stringency conditions) to an influenza virus nucleic acid from a specific influenza subtype, such as influenza subtype H3, H5, Eurasian H7, North American H7, or H9. Such primers are specific for one influenza subtype, for example specific for an influenza HA sequence that is subtype-specific, such as an H3, H5, Eurasian H7, North American H7, or H9 HA nucleic acid sequence. Subtype-specific primers can be used to amplify sequences specific to the various influenza subtypes. In some examples, a primer that is subtype-specific for (for example, hybridizes to) influenza subtype H3 (seasonal and/or variant) is not subtype-specific for (for example, does not substantially hybridize to) influenza subtype H5, influenza subtype H7 (Eurasian or North American) or influenza subtype H9. In another example, a primer that is subtype-specific for (for example, hybridizes to) influenza subtype H5 is not subtype-specific for (for example, does not substantially hybridize to) influenza subtype H3 (seasonal or variant), H7 (Eurasian or North American), or H9. In another example, a primer that is subtype-specific for (for example, hybridizes to) influenza subtype Eurasian H7 is not subtype-specific for (for example, does not substantially hybridize to) influenza subtype H3 (seasonal or variant), H5, North American H7, or H9. In a further example, a primer that is subtype-specific for (for example, hybridizes to) influenza subtype North American H7 is not subtype-specific for (for example, does not substantially hybridize to) influenza subtype H3 (seasonal or variant), H5, Eurasian H7, or H9. In another example, a primer that is subtype-specific for (for example, hybridizes to) influenza subtype H9 is not subtype-specific for (for example, does not substantially hybridize to) influenza subtype H3 (seasonal or variant), H5, or H7 (Eurasian or North American). One of ordinary skill in the art will understand that subtype-specific primers, such as those disclosed herein are also not subtype-specific for (for example, do not hybridize to) other influenza virus subtypes, such as influenza subtype H1.

In some embodiments, the primer is specific for an influenza subtype H3 (seasonal or variant) sequence, such as a nucleic acid including the sequence set forth as any one of SEQ ID NOs: 17-22. In a specific example, a primer specific for an influenza subtype H3 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 1 or SEQ ID NO: 2. In further embodiments, the primer is specific for an influenza subtype H5 sequence, such as a nucleic acid including the sequence set forth as SEQ ID NOs: 53-91. In a specific example, a primer specific for an influenza subtype H5 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 5, SEQ ID NO: 6, SEQ ID NO: 7, SEQ ID NO: 8, SEQ ID NO: 11, or SEQ ID NO: 12. In additional embodiments, the primer is specific for an influenza subtype Eurasian H7 sequence, such as a nucleic acid including the sequence set forth as any one of SEQ ID NOs: 23-28. In a specific example, a primer specific for an influenza subtype Eurasian H7 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 14 or SEQ ID NO: 15. In other embodiments, the primer is specific for an influenza subtype North American H7 sequence, such as a nucleic acid including the sequence set forth as any one of SEQ ID NOs: 110, 11, 112, 113, 114, or 115. In a specific example, a primer specific for an influenza subtype North American H7 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 104 or SEQ ID NO: 105. In additional embodiments, the primer is specific for an influenza subtype H9 sequence, such as a nucleic acid including the sequence set forth as any one of SEQ ID NOs: 116, 117, 118, 119, 120, 121 or 122. In a specific example, a primer specific for an influenza subtype H9 nucleic acid includes a nucleic acid sequence at least 90% identical (such as a nucleic acid sequence at least 91%, 92%, 93%, 94%, 95%, 96%, 97%, 98%, 99%, or even 100% identical) to SEQ ID NO: 107 or SEQ ID NO: 108.

In certain embodiments the primers are included in a set of primers, such as a pair of primers, capable of hybridizing to and amplifying an influenza nucleic acid. Such a set of primers comprises at least one forward primer and at least one reverse primer, where the primers are specific for the amplification of an influenza subtype nucleic acid. In some examples, the set of primers includes at least one pair of primers that is specific for the amplification of influenza subtype H3, subtype H5, subtype Eurasian H7, subtype North American H7, subtype H9, or two or more thereof.

In certain examples, the pair of primers is specific for the amplification of an influenza subtype H3 (seasonal and/or variant) nucleic acid and includes a forward primer at least 90% identical (such as a nucleic acid sequence at least 91%, 92%, 93%, 94%, 95%, 96%, 97%, 98%, 99%, or even 100% identical) to SEQ ID NO: 1 and a reverse primer at least 90% identical (such as a nucleic acid sequence at least 91%, 92%, 93%, 94%, 95%, 96%, 97%, 98%, 99%, or even 100% identical) to SEQ ID NO:2. In other examples, the pair of primers is specific for the amplification of an influenza subtype H5 nucleic acid and includes a forward primer at least 90% identical (such as a nucleic acid sequence at least 91%, 92%, 93%, 94%, 95%, 96%, 97%, 98%, 99%, or even 100% identical) to SEQ ID NO: 5 or SEQ ID NO: 6 and a reverse primer at least 90% identical (such as a nucleic acid sequence at least 91%, 92%, 93%, 94%, 95%, 96%, 97%, 98%, 99%, or even 100% identical) to SEQ ID NO: 7 or SEQ ID NO: 8. In another example, the pair of primers is specific for the amplification of an influenza subtype H5 nucleic acid and includes a forward primer at least 90% identical (such as a nucleic acid sequence at least 91%, 92%, 93%, 94%, 95%, 96%, 97%, 98%, 99%, or even 100% identical) to SEQ ID NO: 11 and a reverse primer at least 90% identical (such as a nucleic acid sequence at least 91%, 92%, 93%, 94%, 95%, 96%, 97%, 98%, 99%, or even 100% identical) to SEQ ID NO:12. In other examples, the pair of primers is specific for the amplification of an influenza subtype Eurasian H7 nucleic acid and includes a forward primer at least 90% identical (such as a nucleic acid sequence at least 91%, 92%, 93%, 94%, 95%, 96%, 97%, 98%, 99%, or even 100% identical) to SEQ ID NO: 14 and a reverse primer at least 90% identical (such as a nucleic acid sequence at least 91%, 92%, 93%, 94%, 95%, 96%, 97%, 98%, 99%, or even 100% identical) to SEQ ID NO: 15. In further examples, the pair of primers is specific for the amplification of an influenza subtype North American H7 nucleic acid and includes a forward primer at least 90% identical (such as a nucleic acid sequence at least 91%, 92%, 93%, 94%, 95%, 96%, 97%, 98%, 99%, or even 100% identical) to SEQ ID NO: 104 and a reverse primer at least 90% identical (such as a nucleic acid sequence at least 91%, 92%, 93%, 94%, 95%, 96%, 97%, 98%, 99%, or even 100% identical) to SEQ ID NO: 105. In other examples, the pair of primers is specific for the amplification of an influenza subtype H9 nucleic acid and includes a forward primer at least 90% identical (such as a nucleic acid sequence at least 91%, 92%, 93%, 94%, 95%, 96%, 97%, 98%, 99%, or even 100% identical) to SEQ ID NO: 107 and a reverse primer at least 90% identical (such as a nucleic acid sequence at least 91%, 92%, 93%, 94%, 95%, 96%, 97%, 98%, 99%, or even 100% identical) to SEQ ID NO: 108.

In further examples, the set of primers also includes one or more additional influenza type or subtype-specific primers (such as one or more primer pairs), such as primers that are specific the amplification of one or more of influenza type A, influenza pandemic 2009 type A, influenza type B, influenza subtype H1, influenza pandemic 2009 subtype H1, influenza virus H3 (seasonal or variant), influenza subtype H5, influenza subtype H7 (Eurasian or North American), and/or influenza subtype H9 (for example SEQ ID NOs: 37-50, 92, 93, 95, 96, 98, 99, 101, and/or 102). In additional embodiments, the set of primers includes one or more control primers, such as one or more primers specific for a human nucleic acid (for example, RNase P, such as SEQ ID NOs: 51 and/or 52).

Figure 1:
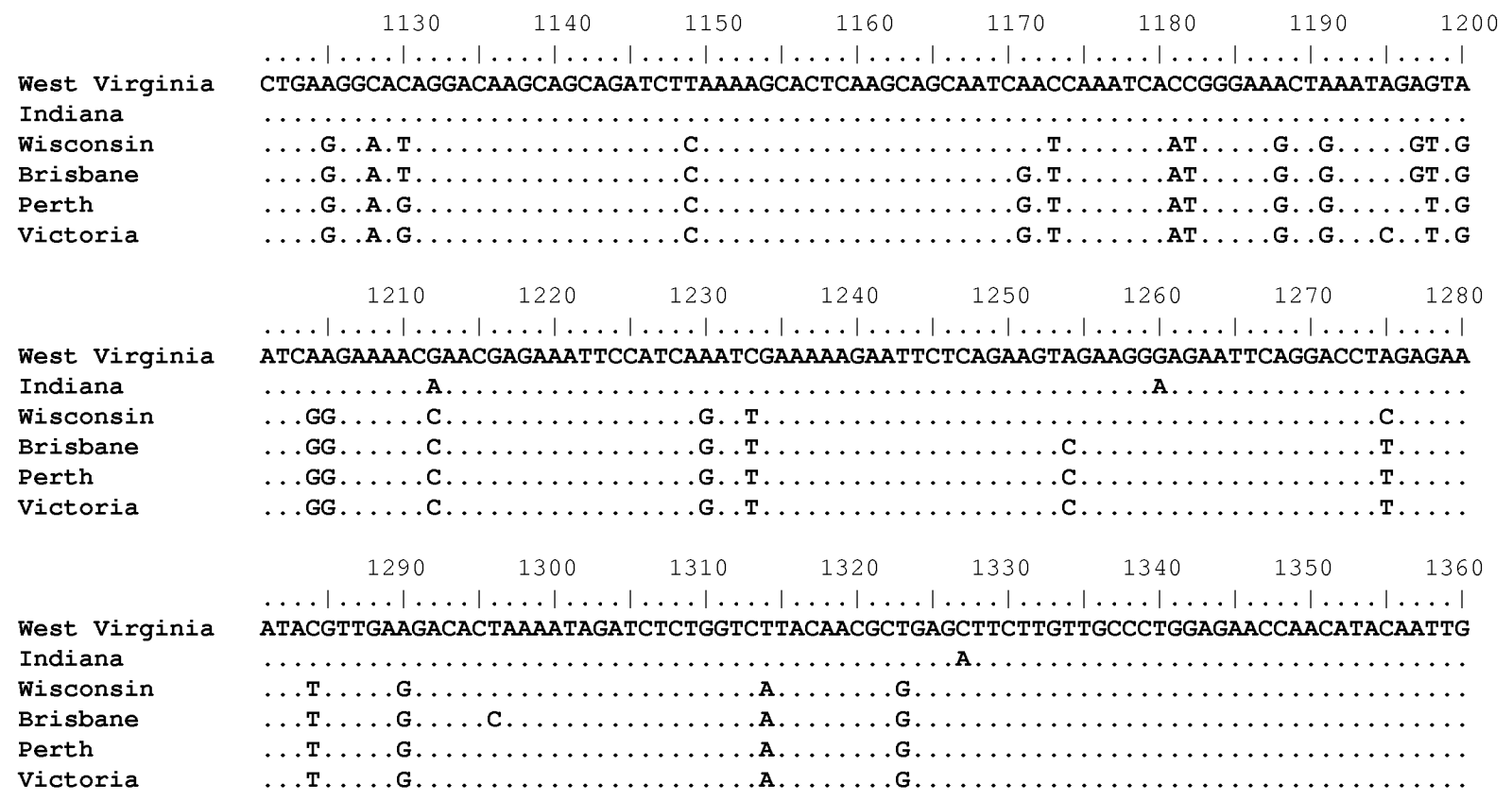

Although exemplary probes and primers are provided in SEQ ID NOs: 1-16 and 104-109, one skilled in the art will appreciate that the primer or probe sequences can be varied slightly by moving the probe or primer a few nucleotides upstream or downstream from the nucleotide positions that they hybridize to on the influenza nucleic acid, provided that the probe or primer is still specific for the influenza sequence, such as specific for the subtype of the influenza sequence, for example specific for any one of SEQ ID NOs: 17-28, 53-91, or 110-122. For example, one of ordinary skill in the art will appreciate that by analyzing sequence alignments of influenza type or subtype genes (for example HA gene sequences, such as those shown in FIGS. 1-6) that variations of the probes or primers disclosed herein can be made for example, by "sliding" the probes and/or primers a few nucleotides 5' or 3' from their positions, and that such variation will still be specific for the influenza viral subtype.

Also provided by the present application are probes and primers that include variations to the nucleotide sequences shown in any of SEQ ID NOs: 1-16 and 104-109, as long as such variations permit detection of the influenza virus nucleic acid, such as an influenza subtype nucleic acid. For example, a probe or primer can have at least 90% sequence identity such as at least 91%, at least 92%, at least 93%, at least 94%, at least 95%, at least 96%, at least 97%, at least 98%, at least 99% to a nucleic acid consisting of the sequence shown in any of SEQ ID NOs: 1-16 and 104-109. In some examples, the number of nucleotides does not change, but the nucleic acid sequence shown in any of SEQ ID NOs: 1-16 and 104-109 can vary at a few nucleotides, such as changes at 1, 2, 3, or 4 nucleotides.

The present application also provides probes and primers that are slightly longer or shorter than the nucleotide sequences shown in any of SEQ ID NOs: 1-16 and 104-109, as long as such deletions or additions permit detection or amplification of the desired influenza nucleic acid, such as an influenza subtype. For example, a probe or primer can include a few nucleotide deletions or additions at the 5'- and/or 3'-end of the probe or primer shown in any of SEQ ID NOs: 1-16 and 104-109, such as addition or deletion of 1, 2, 3, or 4 nucleotides from the 5'- or 3'-end, or combinations thereof (such as a deletion from one end and an addition to the other end). In such examples, the number of nucleotides may change. One of skill in the art will appreciate that sequence alignments (such as those shown in FIGS. 1-6) provide sufficient guidance as to what additions and/or subtractions can be made, while still maintaining specificity for the influenza viral subtype.

Also provided are probes and primers that are degenerate at one or more positions (such as 1, 2, 3, 4, 5, or more positions), for example, a probe or primer that includes a mixture of nucleotides (such as 2, 3, or 4 nucleotides) at a specified position in the probe or primer. In other examples, the probes and/or primers include one or more synthetic bases or alternative bases (such as inosine). In other examples, the probes and/or primers disclosed herein include one or more modified nucleotides or nucleic acid analogues, such as one or more locked nucleic acids (see, e.g., U.S. Pat. No. 6,794,499) or one or more superbases (Nanogen, Inc., Bothell, Wash.). In other examples, the probes and primers disclosed herein include a minor groove binder conjugated to the 5' or 3' end of the oligonucleotide (see, e.g., U.S. Pat. No. 6,486,308).

IV. Methods of Detecting Influenza Virus Nucleic Acids

Methods for the detection of influenza nucleic acids are disclosed, for example to determine if a sample contains an influenza virus. Methods also are provided for determining the type and/or subtype of the influenza viral nucleic acid, for example to determine the type and/or subtype of influenza virus present in a sample. A particular application of the influenza virus specific primers and probes disclosed herein is for the detection and subtyping of influenza viruses in a sample, such as a biological sample obtained from a subject that has or is suspected of having an influenza infection. Thus, in some embodiments the disclosed methods can be used to diagnose if a subject has an influenza infection and/or discriminate the viral subtype with which the subject is infected.

The methods described herein may be used for any purpose for which detection of influenza is desirable, including diagnostic and prognostic applications, such as in laboratory and clinical settings. Appropriate samples include any conventional environmental or biological samples, including clinical samples obtained from a human or animal subject, such as a bird (such as a chicken or turkey) or swine. Suitable samples include all biological samples useful for detection of viral infection in subjects, including, but not limited to, cells, tissues (for example, lung, liver or kidney), bone marrow aspirates, bodily fluids (for example, blood, serum, urine, cerebrospinal fluid, bronchoalveolar lavage, tracheal aspirates or swabs, sputum, nasopharyngeal aspirates or swabs, oropharyngeal aspirates or swabs, saliva), eye swabs, cervical swabs, vaginal swabs, rectal swabs, stool, and stool suspensions. Particularly suitable samples include samples obtained from bronchoalveolar lavage, tracheal aspirates, sputum, nasopharyngeal aspirates, oropharyngeal aspirates, or saliva. Standard techniques for acquisition of such samples are available. See for example, Schluger et al., *J. Exp. Med.* 176:1327-33 (1992); Bigby et al., *Am. Rev. Respir. Dis.* 133:515-18 (1986); Kovacs et al., *NEJM* 318:589-93 (1988); and Ognibene et al., *Am. Rev. Respir. Dis.* 129:929-32 (1984).

In some embodiments, detecting the presence of an influenza nucleic acid sequence in a sample includes the extraction of influenza RNA. RNA extraction relates to releasing RNA from a latent or inaccessible form in a virion, cell, or sample and allowing the RNA to become freely available. In such a state, it is suitable for effective detection and/or amplification of the influenza nucleic acid. Releasing RNA may include steps that achieve the disruption of virions containing viral RNA, as well as disruption of cells that may harbor such virions. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular or viral components, wherein such components may be either particulate or dissolved.

One of ordinary skill in the art will know suitable methods for extracting RNA from a sample; such methods will depend upon, for example, the type of sample in which the influenza RNA is found. For example, the RNA may be extracted using guanidinium isothiocyanate, such as the single-step isolation by acid guanidinium isothiocyanate-phenol-chloroform extraction of Chomczynski et al. (*Anal. Biochem.* 162:156-59, 1987). The sample can be used directly or can be processed, such as by adding solvents, preservatives, buffers, or other compounds or substances. Viral RNA can be extracted using standard methods. For instance, rapid RNA preparation can be performed using a commercially available kit (such as the MAGNA PURE® Compact Nucleic Acid Isolation Kit I (Roche Applied Science, Pleasonton, Calif.); QIAAMP® Viral RNA Mini Kit, QIAAMP® MinElute Virus Spin Kit or RNEASY® Mini Kit (Qiagen, Valencia, Calif.); NUCLISENS® EASY-MAG® or NUCLISENS® MINIMAG® nucleic acid isolation system (bioMérieux, Durham, N.C.); ChargeSwitch® Total RNA Cell Kit (Life Technologies, Carlsbad, Calif.); or MASTERPURE™ Complete DNA and RNA Purification Kit (Epicentre Biotechnologies, Madison, Wis.)). Alternatively, an influenza virion may be disrupted by a suitable detergent in the presence of proteases and/or inhibitors of ribonuclease activity. Additional exemplary methods for extracting RNA are found, for example, in World Health Organization, *Manual for the Virological Investigation of Polio*, World Health Organization, Geneva, 2001.

Detecting an influenza virus nucleic acid in a sample involves contacting the sample with at least one of the influenza specific probes disclosed herein that is capable of hybridizing to an influenza virus nucleic acid under conditions of high stringency or very high stringency (such as a nucleic acid probe capable of hybridizing under high stringency or very high stringency conditions to an influenza nucleic acid nucleic acid set forth as SEQ ID NOs: 17-28, 53-91, or 110-122), for example a probe including a nucleic acid sequence at least 90% identical to the nucleotide sequence set forth as one of SEQ ID NO: 3, SEQ ID NO: 4, SEQ ID NO: 9, SEQ ID NO: 10, SEQ ID NO: 13, SEQ ID NO: 16, SEQ ID NO: 106, or SEQ ID NO: 109, and detecting hybridization between the influenza virus nucleic acid and the probe. Detection of hybridization between the probe and the influenza nucleic acid indicates the presence of the influenza nucleic acid in the sample. In some examples, detection of hybridization between the probe and the influenza virus nucleic acid in the sample diagnoses influenza virus infection in a subject, for example when the sample is a biological sample obtained from the subject.

The influenza virus specific probes disclosed herein can be used to detect the presence of and/or discriminate between influenza subtypes in a sample. For example, contacting a sample with a probe specific for seasonal influenza subtype H3, such as a probe capable of hybridizing under high or very high stringency conditions to an influenza nucleic acid including the sequence set forth as any one of SEQ ID NOs: 19-22, for example a nucleic acid at least 90% identical to the nucleotide sequence set forth as SEQ ID NO: 3, and detecting hybridization between the probe and the influenza nucleic acid indicates that seasonal influenza subtype H3 is present. In another example, contacting a sample with a probe specific for variant influenza subtype H3, such as a probe capable of hybridizing under high or very high stringency conditions to an influenza nucleic acid including the sequence set forth as SEQ ID NO: 17 or SEQ ID NO: 18, for example a nucleic acid at least 90% identical to the nucleotide sequence set forth as SEQ ID NO: 4, and detecting hybridization between the probe and the influenza nucleic acid indicates the presence of variant influenza subtype H3. In another example, contacting a sample with a probe specific for influenza subtype H5, such as a probe capable of hybridizing under high or very high stringency conditions to an influenza nucleic acid including the sequence set forth as SEQ ID NOs: 53-74, for example a nucleic acid at least 90% identical to the nucleotide sequence set forth as SEQ ID NO: 9 or SEQ ID NO: 10, and detecting hybridization between the probe and the influenza nucleic acid indicates the presence of influenza subtype H5. In another example, contacting a sample with a probe specific for influenza subtype H5, such as a probe capable of hybridizing under high or very high stringency conditions to an influenza nucleic acid including the sequence set forth as SEQ ID NOs: 75-91, for example a nucleic acid at least 90% identical to the nucleotide sequence set forth as SEQ ID NO: 13, and detecting the hybridization between the probe and the influenza nucleic acid indicates the presence of influenza subtype H5. In yet another example, contacting a sample with a probe specific for influenza subtype Eurasian H7, such as a probe capable of hybridizing under high or very high stringency conditions to an influenza nucleic acid sequence including the set forth as any one of SEQ ID NOs: 23-28, for example a nucleic acid at least 90% identical to the nucleotide sequence set forth as SEQ ID NO: 16, and detecting hybridization between the probe and the influenza nucleic acid indicates the presence of influenza subtype Eurasian H7. In a further example, contacting a sample with a probe specific for influenza subtype North American H7, such as a probe capable of hybridizing under high or very high stringency conditions to an influenza nucleic acid including the sequence set forth as any one of SEQ ID NOs: 110-115, for example a nucleic acid at least 90% identical to the nucleotide sequence set forth as SEQ ID NO: 106, and detecting hybridization between the probe and the influenza nucleic acid indicates the presence of influenza subtype North American H7. In yet another example, contacting a sample with a probe specific for influenza subtype H9, such as a probe capable of hybridizing under high or very high stringency conditions to an influenza nucleic acid including the sequence set forth as any one of SEQ ID NOs: 116-122, for example a nucleic acid at least 90% identical to the nucleotide sequence set forth as SEQ ID NO: 109, and detecting hybridization between the probe and the influenza nucleic acid indicates the presence of influenza subtype H9.

In some embodiments, the methods further include contacting the sample with additional influenza type-specific and/or influenza subtype-specific probes to further detect or discriminate the type and/or subtype of influenza virus nucleic acid in the sample. In some embodiments, the methods further include contacting the sample with one or more influenza type-specific probes, such as one or more probes specific for influenza type A and/or influenza type B and/or one or more additional influenza subtype-specific probes, such as one or more probes specific for influenza subtype H1, influenza subtype H3 (seasonal or variant), influenza subtype H5, influenza subtype H7 (Eurasian or North American), and/or influenza subtype H9. Exemplary additional probes suitable for the methods disclosed herein are disclosed in International Pat. Publ. No. WO 2007/095155, incorporated by reference herein in its entirety.

In some examples, an influenza A type-specific probe includes a nucleic acid capable of hybridizing under high stringency or very high stringency to an influenza type A M gene sequence. In some examples, the influenza A type-specific probe includes a nucleic acid at least 90% identical (such as a nucleic acid at least 91%, 92%, 93%, 94%, 95%, 96%, 97%, 98%, 99%, or even 100% identical) to the sequence set forth as TGCAGTCCTCGCT-CACTGGGCACG (SEQ ID NO: 29). In other examples, an influenza A type-specific probe is an influenza A pandemic 2009 type-specific probe that includes a nucleic acid capable of hybridizing under high stringency or very high stringency to an influenza type A NP gene sequence. In some examples, the influenza A pandemic 2009 type-specific probe includes a nucleic acid at least 90% identical (such as a nucleic acid at least 91%, 92%, 93%, 94%, 95%, 96%, 97%, 98%, 99%, or even 100% identical) to the sequence set forth as TGAATGGGTCTATCCCGACCAGTGAGTAC (SEQ ID NO: 30). In further examples, an influenza type B specific probe is capable of hybridizing under high or very high stringency conditions to a nucleic acid from influenza B, for example to a nucleic acid from the NS gene of influenza type B. For example, the influenza type B specific probe can include a nucleic acid at least 90% identical (such as a nucleic acid at least 91%, 92%, 93%, 94%, 95%, 96%, 97%, 98%, 99%, or even 100% identical) to the sequence set forth as CCAATTCGAGCAGCTGAAACTGCGGTG (SEQ ID NO: 31).

In some examples, an influenza subtype H1 specific probe includes a nucleic acid capable of hybridizing under high stringency or very high stringency to an influenza subtype H1 HA gene sequence. In some examples, the influenza subtype H1 specific probe includes a nucleic acid at least 90% identical (such as a nucleic acid at least 91%, 92%, 93%, 94%, 95%, 96%, 97%, 98%, 99%, or even 100% identical) to the sequence set forth as TGAYCCAAAGC-CTCTACTCAGTGCGAAAGC (SEQ ID NO: 32). In other examples, an influenza subtype H1 pandemic 2009 specific probe includes a nucleic acid capable of hybridizing under high stringency or very high stringency to an influenza subtype H1 pandemic 2009 HA gene sequence. In some examples, the influenza subtype H1 pandemic 2009 specific probe includes a nucleic acid at least 90% identical (such as a nucleic acid at least 91%, 92%, 93%, 94%, 95%, 96%, 97%, 98%, 99%, or even 100% identical) to the sequence set forth as ATACATCCGATCACMATTGGAAAATGTCC (SEQ ID NO: 33). In other examples, an influenza subtype North American H7 specific probe includes a nucleic acid capable of hybridizing under high stringency or very high stringency to an influenza subtype North American H7 gene sequence. In some examples, the influenza subtype North American H7 specific probe includes a nucleic acid at least 90% identical (such as a nucleic acid at least 91%, 92%, 93%, 94%, 95%, 96%, 97%, 98%, 99%, or even 100% identical) to the sequence set forth as AAAGCACCCA-RTCTGCAATAGATCAGATCACAGGC (SEQ ID NO: 34). In other examples, an influenza subtype H9 specific probe includes a nucleic acid capable of hybridizing under high stringency or very high stringency to an influenza subtype H9 gene sequence. In some examples, the influenza subtype H9 specific probe includes a nucleic acid at least 90% identical (such as a nucleic acid at least 91%, 92%, 93%, 94%, 95%, 96%, 97%, 98%, 99%, or even 100% identical) to the sequence set forth as CCCAGAACAR-GAAGGCAGCAAACCCCATTG (SEQ ID NO: 35).

In some examples, the methods also include contacting the sample with a positive control probe, such as a probe capable of hybridizing to a human nucleic acid, for example when the subject is a human. In some examples, the positive control probe is a probe capable of hybridizing to a human RNase P nucleic acid, such as a probe including the nucleic acid sequence set forth as TTCTGACCTGAAGGCTCT-GCGCG (SEQ ID NO: 36).

In some embodiments, the probe is detectably labeled, either with an isotopic or non-isotopic label; in alternative embodiments, the influenza nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization determined. In some examples the hybridization results in a detectable change in signal such as in increase or decrease in signal, for example from the labeled probe. Thus, detecting hybridization comprises detecting a change in signal from the labeled probe during or after hybridization relative to signal from the label before hybridization.

In some embodiments, influenza virus nucleic acids present in a sample are amplified prior to or substantially simultaneously with using a hybridization probe for detection. For instance, it can be advantageous to amplify a portion of the influenza virus nucleic acid, and detect the presence of the amplified influenza virus nucleic acid, for example, to increase the number of nucleic acids that can be detected, thereby increasing the signal obtained. Influenza specific nucleic acid primers can be used to amplify a region that is at least about 50, at least about 60, at least about 70, at least about 80 at least about 90, at least about 100, at least about 200, at least about 300, or more base pairs in length to produce amplified influenza specific nucleic acids. Any nucleic acid amplification method can be used to detect the presence of influenza in a sample. In one specific, non-limiting example, polymerase chain reaction (PCR) is used to amplify the influenza nucleic acid sequences. In other specific, non-limiting examples, real-time PCR, reverse transcriptase-polymerase chain reaction (RT-PCR), real-time reverse transcriptase-polymerase chain reaction (rRT-PCR), ligase chain reaction, or transcription-mediated amplification is used to amplify the influenza nucleic acid. In a specific example, the influenza virus nucleic acid is amplified by rRT-PCR. Techniques for nucleic acid amplification are well-known to those of ordinary skill in the art.

Typically, at least two primers are utilized in the amplification reaction, however it is envisioned that one primer can be utilized, for example to reverse transcribe a single stranded nucleic acid such as a single-stranded influenza RNA. Amplification of the influenza nucleic acid involves contacting the influenza nucleic acid with one or more primers that are capable of hybridizing to and directing the amplification of an influenza nucleic acid (such as a nucleic acid capable of hybridizing under high stringency or very high stringency conditions to an influenza nucleic acid, for example a primer that is least 90% identical to the nucleotide sequence set forth as one of SEQ ID NO: 1, SEQ ID NO: 2, SEQ ID NO: 5, SEQ ID NO: 6, SEQ ID NO: 7, SEQ ID NO: 8, SEQ ID NO: 11, SEQ ID NO: 12, SEQ ID NO: 14, SEQ ID NO: 15, SEQ ID NO: 104, SEQ ID NO: 105, SEQ ID NO: 107, or SEQ ID NO: 108). In some embodiments, the sample is contacted with at least one primer that is specific for an influenza subtype, such as those disclosed herein.

In some embodiments, the sample is contacted with at least one pair of primers that include a forward and reverse primer that both hybridize to an influenza nucleic acid specific for an influenza subtype, such as influenza subtype seasonal H3, influenza subtype variant H3, influenza subtype H5, influenza subtype Eurasian H7, influenza subtype North American H7, or influenza subtype H9. Examples of suitable primer pairs for the amplification of influenza subtype-specific nucleic acids are described above in Section IIIB.

In additional embodiments, the methods further include amplifying one or more influenza type-specific and/or influenza subtype-specific nucleic acids to further detect or discriminate the type and/or subtype of influenza virus nucleic acid in the sample. In some embodiments, the methods further include contacting the sample with one or more additional influenza type-specific primers, such as one or more primers specific for influenza type A and/or influenza type B and/or one or more influenza subtype-specific primers specific, such as one or more primers specific for influenza subtype H1, influenza subtype H3, influenza subtype H5, influenza subtype H7, and/or influenza subtype H9. Exemplary additional primers suitable for the methods disclosed herein are disclosed in International Pat. Publ. No. WO 2007/095155, incorporated by reference herein in its entirety.

In some embodiments, the methods include contacting the sample with one or more primers capable of hybridizing to and directing the amplification of an influenza type A nucleic acid molecule (such as an influenza type A M gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence set forth as GACCRATCCTGTCACCTCT-GAC (SEQ ID NO: 37) or AGGGCATTYTGGA-CAAAKCGTCTA (SEQ ID NO: 38). In several embodiments, a pair of primers capable of hybridizing to and directing the amplification of an influenza type A nucleic acid molecule includes the primers set forth as SEQ ID NO: 37 and SEQ ID NO: 38.

In additional embodiments, the methods further include contacting the sample with one or more primers capable of hybridizing to and directing the amplification of an influenza type A pandemic 2009 nucleic acid molecule (such as influenza pandemic 2009 type A NP gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence set forth as TTGCAGTAGCAAGTGGGCATGA (SEQ ID NO: 39) or TCTTGTGAGCTGGGTTTTCATTTG (SEQ ID NO:40). In several embodiments, a pair of primers capable of hybridizing to and directing the amplification of an influenza type A pandemic 2009 nucleic acid molecule includes the primers set forth as SEQ ID NO: 39 and SEQ ID NO: 40.

In further embodiments, the methods further include contacting the sample with one or more primers capable of hybridizing to and directing the amplification of an influenza type B nucleic acid molecule (such as an influenza type B NS gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence set forth as TCCT-CAAYTCACTCTTCGAGCG (SEQ ID NO: 41) or CGGT-GCTCTTGACCAAATTGG (SEQ ID NO: 42). In several embodiments, a pair of primers capable of hybridizing to and directing the amplification of an influenza type B nucleic acid molecule includes the primers set forth as SEQ ID NO: 41 and SEQ ID NO: 42.

In still further embodiments, the methods further include contacting the sample with one or more primers capable of hybridizing to and directing the amplification of an influenza subtype H1 nucleic acid molecule (such as an influenza subtype H1 HA gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence set forth as AACTACTACTGGACTCTRCTKGAA (SEQ ID NO: 43) or CCATTGGTGCATTTGAGKTGATG (SEQ ID NO: 44). In several embodiments, a pair of primers capable of hybridizing to and directing the amplification of an influenza subtype H1 nucleic acid molecule includes the primers set forth as SEQ ID NO: 43 and SEQ ID NO: 44.

In additional embodiments, the methods further include contacting the sample with one or more primers capable of hybridizing to and directing the amplification of an influenza H1 pandemic 2009 nucleic acid molecule (such as an influenza subtype H1 pandemic 2009 HA gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence set forth as GTGCTATAAACACCAGCCTC-CCATT (SEQ ID NO: 45) or AGACGGGAYATTCCT-CAATCCTG (SEQ ID NO: 46). In several embodiments, a pair of primers capable of hybridizing to and directing the amplification of an influenza H1 pandemic 2009 nucleic acid molecule includes the primers set forth as SEQ ID NO: 45 and SEQ ID NO: 46.

In further embodiments, the methods further include contacting the sample with one or more primers capable of hybridizing to and directing the amplification of an influenza subtype North American H7 nucleic acid molecule (such as an influenza subtype North American H7 HA gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence set forth as AAATGCACAAGGA-GAGGGAACTG (SEQ ID NO: 47) or CATTGCYACYA-ASAGYTCAGCRT (SEQ ID NO: 48). In several embodiments, a pair of primers capable of hybridizing to and directing the amplification of an influenza subtype North American H7 nucleic acid molecule includes the primers set forth as SEQ ID NO: 47 and SEQ ID NO: 48.

In still further embodiments, the methods further include contacting the sample with one or more primers capable of hybridizing to and directing the amplification of an influenza subtype H9 nucleic acid molecule (such as such as an influenza subtype H9 HA gene nucleic acid) and includes a nucleic acid sequence that is at least 90% identical, such as at least 91%, 92%, 93%, 94%, 95%, 96%, 97%, 98%, 99%, or even 100% identical, to the nucleic acid sequence set forth as CAAGCTGGAATCTGARGGAACTTACA (SEQ ID NO: 49) or GCATCTGCAAGATCCATTGGACAT (SEQ ID NO: 50). In several embodiments, a pair of primers capable of hybridizing to and directing the amplification of an influenza subtype H9 nucleic acid molecule includes the primers set forth as SEQ ID NO: 49 and SEQ ID NO: 50.

In further embodiments, the methods also include contacting the sample with one or more positive control primers capable of hybridizing to and directing the amplification of a human RNase P nucleic acid molecule and includes a nucleic acid sequence that is at least 90% identical, such as at least 91%, 92%, 93%, 94%, 95%, 96%, 97%, 98%, 99%, or even 100% identical, to the nucleic acid sequence set forth as AGATTTGGACCTGCGAGCG (SEQ ID NO: 51) or GAGCGGCTGTCTCCACAAGT (SEQ ID NO: 52). In several embodiments, a pair of primers capable of hybridizing to and directing the amplification of a human RNase P nucleic acid molecule includes the primers set forth as SEQ ID NO: 51 and SEQ ID NO: 52.

Any type of thermal cycler apparatus can be used for the amplification of the influenza nucleic acids and/or the determination of hybridization. Examples of suitable apparatuses include a PTC-100® Peltier Thermal Cycler (MJ Research, Inc.; San Francisco, Calif.), a ROBOCYCLER® 40 Temperature Cycler (Stratagene; La Jolla, Calif.), or a GENEAMP® PCR System 9700 (Applied Biosystems; Foster City, Calif.). For real-time PCR, any type of real-time thermocycler apparatus can be used. For example, a BioRad iCycler iQ™, LIGHTCYCLER™ (Roche; Mannheim, Germany), a 7700 Sequence Detector (Perkin Elmer/Applied Biosystems; Foster City, Calif.), ABI™ systems such as the 7000, 7500, 7700, or 7900 systems (Applied Biosystems; Foster City, Calif.), or an MX4000™, MX3000™ or MX3005™ (Stratagene; La Jolla, Calif.), and Cepheid SMARTCYCLER™ can be used to amplify nucleic acid sequences in real-time. One of ordinary skill in the art can select additional thermocycler platforms suitable for the methods disclosed herein.

The amplified influenza nucleic acid, for example an influenza type or subtype-specific nucleic acid, can be detected in real-time, for example by real-time PCR such as real-time RT-PCR, in order to determine the presence, the identity, and/or the amount of an influenza type or subtype-specific nucleic acid in a sample. In this manner, an amplified nucleic acid sequence, such as an amplified influenza nucleic acid sequence, can be detected using a probe specific for the product amplified from the influenza sequence of interest, such as an influenza sequence that is specific for influenza type A, type B, subtype H1, H3 (seasonal or variant), H5, North American H7, Eurasian H7, and/or H9. Detecting the amplified product includes the use of labeled probes that are sufficiently complementary and hybridize to the amplified nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid of interest includes the combined use of PCR amplification and a labeled probe such that the product is measured using real-time RT-PCR. In another embodiment, the detection of an amplified target nucleic acid of interest includes the transfer of the amplified target nucleic acid to a solid support, such as a blot, for example a Northern blot, and probing the blot with a probe, for example a labeled probe, that is complementary to the amplified target nucleic acid. In yet another embodiment, the detection of an amplified target nucleic acid of interest includes the hybridization of a labeled amplified target nucleic acid to probes disclosed herein that are an arrayed in a predetermined array with an addressable location and that are complementary to the amplified target nucleic acid.

In one embodiment, fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN® probe) can identify a probe that specifically hybridizes to the nucleic acid of interest and in this way, using influenza type and/or subtype-specific probes, can detect the presence, identity, and/or amount of an influenza type and/or subtype in a sample. In one embodiment, fluorescently-labeled DNA probes used to identify amplification products have spectrally distinct emission wavelengths, thus allowing them to be distinguished within the same reaction tube (for example, using multiplex PCR, multiplex RT-PCR or multiplex rRT-PCR).

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid.

In some examples, the disclosed methods can predict with a sensitivity of at least 90% and a specificity of at least 90% for presence of an influenza virus nucleic acid or an influenza subtype H3 (seasonal or variant), H5, H7 (Eurasian or North American), or H9 nucleic acid, such as a sensitivity of at least 91%, 92%, 93%, 94%, 95%, 96%, 97%, 98%, 99%, or even 100% and a specificity of at least of at least 91%, 92%, 93%, 94%, 95%, 96%, 97%, 98%, 99%, or even 100%. In other examples, disclosed methods can detect presence of an influenza virus nucleic acid or an influenza subtype H3 (seasonal or variant), H5, H7 (Eurasian or North American), or H9 nucleic acid in a sample with a limit of detection (LOD) of about $10^1$-$10^8$ EID$_{50}$/ml, about $10^4$-$10^7$ EID$_{50}$/ml, about $10^1$-$10^4$ EID$_{50}$/ml, about $10^2$-$10^5$ EID$_{50}$/ml, or about $10^3$-$10^6$ EID$_{50}$/ml (such as about $10^1$, $10^2$, $10^3$, $10^4$, $10^5$, $10^6$, $10^7$, or $10^8$ EID$_{50}$/mL).

V. Arrays

Arrays containing a plurality of heterogeneous probes for the detection, typing, and/or subtyping of influenza viruses are disclosed. Such arrays may be used to rapidly detect and/or identify the type and/or subtype of an influenza virus in a sample. For example the arrays can be used to determine the presence of influenza A, pandemic influenza A, and/or influenza B in a sample and to determine if the influenza virus is of subtype H1, H3 (seasonal or variant), H5, H7 (North American or Eurasian), and/or H9.

Arrays are arrangements of addressable locations on a substrate, with each address containing a nucleic acid, such as a probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, an influenza profiling array includes one or more influenza subtype-specific probes (such as 2, 3, 4, 5, 6, 7, 8, 9, 10, 11, 12, 13, 14, 15, 20, 25, 50, 100, or more probes), such as one or more influenza subtype seasonal H3, variant H3, H5, Eurasian H7, North American H7, and/or H9 probes. In some examples, the array includes 1, 2, 3, 4, 5, 6, 7, 8, or more probes, such as 1, 2, 3, 4, 5, 6, 7, or all of the probes at least 90% identical to the nucleic acid sequences set forth as SEQ ID NO: 3, SEQ ID NO: 4, SEQ ID NO: 9, SEQ ID NO: 10, SEQ ID NO: 13, SEQ ID NO: 16, SEQ ID NO: 106, or SEQ ID NO: 109. In one example, the array includes all of the probes set forth as SEQ ID NO: 3, SEQ ID NO: 4, SEQ ID NO: 9, SEQ ID NO: 10, SEQ ID NO: 13, SEQ ID NO: 16, SEQ ID NO: 106, and SEQ ID NO: 109, such as these sequences in separate wells of a multi-well plate.

In some embodiments, the array also includes additional probes, such as additional influenza virus type-specific or subtype-specific probes. In some examples, the array includes one or more influenza type-specific probes, such as one or more influenza A, pandemic 2009 influenza A, or influenza B type-specific probes. For example, the array may include one or more (such as 1, 2, or all) of the probes set forth as SEQ ID NO: 29, SEQ ID NO: 30, and SEQ ID NO: 31. In additional embodiments, the array also includes one or more additional subtype-specific probes, such as one or more influenza subtype H1, influenza H1 pandemic 2009, influenza subtype H3, influenza subtype H5, influenza subtype North American H7, influenza subtype Eurasian H9, or influenza subtype H9 probes. In some examples, the array includes one or more (such as 1, 2, 3, 4, 5, 6, 7, or all) of the probes set forth as SEQ ID NO: 32, SEQ ID NO: 33, SEQ ID NO: 34, SEQ ID NO: 35, SEQ ID NO: 94, SEQ ID NO: 97, SEQ ID NO: 100, and SEQ ID NO: 103.

In further embodiments, the array also includes one or more control probes, such as one or more positive or negative control probes. In one example, the array includes at least one positive control probe, such as a probe capable of hybridizing to a human nucleic acid, such as RNase P probe (for example, SEQ ID NO: 36).

In some embodiments, an influenza profiling array is a collection of separate probes at the array addresses. The influenza profiling array is then contacted with a sample suspected of containing influenza nucleic acids under conditions allowing hybridization between the probe and nucleic acids in the sample to occur. Any sample potentially containing, or even suspected of containing, influenza nucleic acids may be used, including nucleic acid extracts, such as amplified or non-amplified DNA or RNA preparations. A hybridization signal from an individual address on the array (such as a well) indicates that the probe hybridizes to a nucleotide within the sample. This system permits the simultaneous analysis of a sample by plural probes and yields information identifying the influenza nucleic acids contained within the sample. In alternative embodiments, the array contains influenza nucleic acids and the array is contacted with a sample containing a probe. In any such embodiment, either the probe or the influenza nucleic acids may be labeled to facilitate detection of hybridization.

The nucleic acids may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples (such as one or more probes) occurring on the array a plurality of times (twice or more) to provide an added feature to the array, such as redundant activity or to provide internal controls.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

Influenza profiling arrays may vary in structure, composition, and intended functionality, and may be based on either a macroarray or a microarray format, or a combination thereof. Such arrays can include, for example, at least 5, at least 10, at least 15, at least 20, at least 25, at least 50, at least 100, or more addresses, usually with a single type of nucleic acid at each address. In one example, the array is a 96-well plate. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medical research laboratories, universities, or other institutions without the need for investment in specialized and expensive reading equipment.

Examples of substrates for the arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). In some examples, the array substrate is a multi-well plate, such as a 96-well plate or a 384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

Addresses in an array may be of a relatively large size, such as large enough to permit detection of a hybridization signal without the assistance of a microscope or other equipment. Thus, addresses may be as small as about 0.1 mm across, with a separation of about the same distance. Alternatively, addresses may be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (for example, larger addresses will usually be found on larger arrays, while smaller addresses may be found on smaller arrays). Such a correlation is not necessary, however.

The arrays herein may be described by their densities (the number of addresses in a certain specified surface area). For macroarrays, array density may be about one address per square decimeter (or one address in a 10 cm by 10 cm region of the array substrate) to about 50 addresses per square centimeter (50 targets within a 1 cm by 1 cm region of the substrate). For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GENECHIP® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample may be labeled, such as with a fluorescent label and, after hybridization, the hybridization signals may be detected and analyzed.

VI. Kits

The nucleic acid primers and probes disclosed herein can be supplied in the form of a kit for use in the detection, typing, and/or subtyping of influenza, including kits for any of the arrays described above. In such a kit, an appropriate amount of one or more of the nucleic acid probes and/or primers is provided in one or more containers or held on a substrate. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, multi-well plates, ampoules, or bottles. The kits can include either labeled or unlabeled nucleic acid probes for use in detection, typing, and/or subtyping of influenza nucleic acids (such as those disclosed herein). The kits can additionally include one or more control probes and/or primers, for example for the detection of human RNase P.

In some embodiments, one or more primers (as described above), such as pairs of primers, may be provided in pre-measured single use amounts in individual, typically disposable, wells, tubes, or equivalent containers. With such an arrangement, the sample to be tested for the presence of influenza nucleic acids can be added to the individual tubes or wells and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A kit may include more than two primers in order to facilitate the PCR amplification of a larger number of influenza nucleotide sequences.

In some embodiments, kits also may include the reagents necessary to carry out hybridization and/or PCR amplification reactions, including DNA sample preparation reagents, appropriate buffers (such as polymerase buffer), salts (for example, magnesium chloride), and deoxyribonucleotides (dNTPs).

Particular embodiments include a kit for detecting and typing and/or subtyping an influenza nucleic acid based on the arrays described above. Such a kit includes at least one probe specific for an influenza nucleic acid (as described above) and instructions. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed tubes) or the wells of an array substrate (for example, a 96-well microtiter plate sealed with a protective plastic film). In some embodiments, the probes are included on an array, such as the arrays described above. In other particular embodiments, the kit includes equipment, reagents, and instructions for extracting and/or purifying nucleotides from a sample.

In particular examples, the kits disclosed herein include at least one probe for the detection of an influenza virus in a sample, such as one or more (such as 1, 2, 3, 4, 5, 6, 7, or 8) probes having a nucleic acid sequence at least 90% identical to the sequences set forth as SEQ ID NO: 3, SEQ ID NO: 4, SEQ ID NO: 9, SEQ ID NO: 10, SEQ ID NO: 13, SEQ ID NO: 16, SEQ ID NO: 106, or SEQ ID NO: 109. In some examples, the kits further include at least one primer for the amplification of an influenza virus nucleic acid, for example one or more primers (such as 1, 2, 3, 4, 5, 6, 7, 8, 9, 10, 11, 12, 13, 14, or more) primers having a nucleic acid sequence at least 90% identical to the sequences set forth as SEQ ID NO: 1, SEQ ID NO: 2, SEQ ID NO: 5, SEQ ID NO: 6, SEQ ID NO: 7, SEQ ID NO: 8, SEQ ID NO: 11, SEQ ID NO: 12, SEQ ID NO: 14, SEQ ID NO: 15, SEQ ID NO: 104, SEQ ID NO: 105, SEQ ID NO: 107, or SEQ ID NO: 108. The kit may include one or more pairs of primers, including SEQ ID NO: 1 and SEQ ID NO: 2; SEQ ID NO: 5 or SEQ ID NO: 6 and SEQ ID NO: 7 or SEQ ID NO: 8; SEQ ID NO: 11 and SEQ ID NO: 12; SEQ ID NO: 14 and SEQ ID NO: 15; SEQ ID NO: 104 and SEQ ID NO: 105; and/or SEQ ID NO: 107 and SEQ ID NO: 108.

In one specific embodiment, the kit includes at least one probe having a nucleic acid sequence at least 90% identical to the sequence set forth as SEQ ID NO: 3 and/or SEQ ID NO: 4 and a pair of primers having a nucleic acid sequence at least 90% identical to the sequence set forth as SEQ ID NO: 1 and SEQ ID NO: 2; at least one probe having a nucleic acid sequence at least 90% identical to the sequence set forth as SEQ ID NO: 9 and/or SEQ ID NO: 10 and a pair of primers having a nucleic acid sequence at least 90% identical to the sequence set forth as SEQ ID NO: 5 or SEQ ID NO: 6 and SEQ ID NO: 7 or SEQ ID NO: 8; at least one probe having a nucleic acid sequence at least 90% identical to the sequence set forth as SEQ ID NO: 13 and a pair of primers having a nucleic acid sequence at least 90% identical to the sequence set forth as SEQ ID NO: 11 and SEQ ID NO: 12; at least one probe having a nucleic acid sequence at least 90% identical to the sequence set forth as SEQ ID NO: 16 and a pair of primers having a nucleic acid sequence at least 90% identical to the sequence set forth as SEQ ID NO: 14 and SEQ ID NO: 15; at least one probe having a nucleic acid sequence at least 90% identical to the sequence set forth as SEQ ID NO: 106 and a pair of primers having a nucleic acid sequence at least 90% identical to the sequence set forth as SEQ ID NO: 104 and SEQ ID NO: 105; and/or at least one probe having a nucleic acid sequence at least 90% identical to the sequence set forth as SEQ ID NO: 109 and a pair of primers having a nucleic acid sequence at least 90% identical to the sequence set forth as SEQ ID NO: 107 and SEQ ID NO: 108.

The disclosed kits may further include one or more additional probes and/or primers, for example for the detection and/or discrimination or for the further typing and/or subtyping of influenza virus nucleic acids in a sample. The probes and primers may include one or more of SEQ ID NOs: 29-35, 37-50, and SEQ ID NOs: 92-103. The kits may additionally include one or more control probes and/or primers, for example for the detection of a human nucleic acid, for example one or more of SEQ ID NO: 36, SEQ ID NO: 51, and SEQ ID NO: 52.

In some examples, the kits may include materials for obtaining, collecting, or storing a sample, such as lancets, needles, syringes, microscope slides, blood collection tubes, and the like.

The present disclosure is illustrated by the following non-limiting Examples.

EXAMPLES

Example 1

Materials and Methods

This example describes probes and primers and methods used for the detection, typing and subtyping of influenza virus.

Primer and probe sequences for real-time PCR are shown in Table 1. Probes were labeled with 6-carboxyfluorescein (FAM) at the 5' end, an internal Black Hole Quencher 1 (BHQ1) at "T," and a spacer at the 3' end to prevent extension of the probe by Taq polymerase.

TABLE 1

Real-time PCR Primers and Probes

| Primer/Probe | Sequence (5' to 3') | SEQ ID NO: |
|---|---|---|
| H3 Universal Forward | GATCTYAAAAGCACTCARGCAGC | 1 |
| H3 Universal Reverse | AGGTCCTGAATTCTYCCTTCKAC | 2 |
| H3 Seasonal probe (Sea H3) | GATCTYAAAAGCACTCARGCAGCTCCCGA"T"CAA YCKATTCAGCTTCCCATTGA | 3 |
| H3 Variant probe (H3v) | TCTTGATTAC"T"CTRTTYAGTTTCCCGGTG | 4 |
| H5a Forward 1 | TGGAAAGTGTRAGAAACGGRACRTA | 5 |
| H5a Forward 2 | TGGAAAGTATAAGRAACGGAACRTA | 6 |
| H5a Reverse 1 | CTAGGGARCTCGCCACTGTWGA | 7 |
| H5a Reverse 2 | CTAGDGAACTCGCARCTGTTGA | 8 |
| H5a Probe 1 | TGACTACCCGCAG"T"ATTCAGAAGAAKCAAGAYT AA | 9 |
| H5a Probe 2 | CAACTATCCGCAG"T"ATTCAGAAGAAGCAAGATT AA | 10 |
| H5b Forward | GGAATGYCCCAAATATGTGAAATCAA | 11 |
| H5b Reverse | CCRCTCCCCTGCTCRTTRCT | 12 |
| H5b Probe | TACCCA"T"ACCAACCATCTACCATYCCCTGCCAT | 13 |
| EuH7 Forward | AATGCACARGGRGAGGGAACTGC | 14 |
| EuH7 Reverse | CATTGCTACYAAGAGTTCAGCRTT | 15 |
| EuH7 Probe | ACCACACYTC"T"GTYATRGAATCTCTGGTCCA | 16 |
| NA H7 Forward | AAAYGCACAAGGAGARGGAACTGC | 104 |
| NA H7 Reverse | GCATTRTACGACCATAYCTCAGTCATT | 105 |
| NA H7 Probe | AAAGCACYCARTC"T"GCAATAGATCAGATCACAGG | 106 |
| H9 Forward | CTGGARTCTGARGGRACTTACAA | 107 |
| H9 Reverse | AARAAGGCAGCAAACCCCATTG | 108 |
| H9 Probe | CYATTTAT"T"CRACTGTCGCCTCATCTCTTG | 109 |

R = A + G; Y = C + T; K = G + T; W = A + T; D = G + A + T

Hydrolysis probe (TAQMAN®) rRT-PCR reactions were performed using Invitrogen SuperScript® III Platinum® One-Step qRT-PCR kit (Life Technologies, Carlsbad, Calif.), Ambion AgPath-ID® One-Step RT PCR kit (Ambion, Austin, Tex.), and gScript™ One-Step qRT-PCR kit (Quanta Biosciences, Gaithersburg, Md.), according to the manufacturer's recommended procedures. Primer and probe reaction concentrations were 0.8 μM and 0.2 μM, respectively.

Each reaction included 20 μl of rRT-PCR master mix. The master mix was prepared as shown in Table 2.

TABLE 2 rRT-PCR Master Mix

| | Invitrogen | Ambion AgPath | Quanta |
|---|---|---|---|
| Nuclease free water | N × 5.5 μl | N × 5.0 μl | N × 5.5 μl |
| Forward primer (0.8 μM final concentration) | N × 0.5 μl | N × 0.5 μl | N × 0.5 μl |
| Reverse primer (0.8 μM final concentration) | N × 0.5 μl | N × 0.5 μl | N × 0.5 μl |
| Probe (0.2 μM final concentration) | N × 0.5 μl | N × 0.5 μl | N × 0.5 μl |
| RT Mix | N × 0.5 μl | N × 1.0 μl | N × 0.5 μl |
| 2X PCR Master Mix | N × 12.5 μl | N × 12.5 μl | N × 12.5 μl |
| Total volume | N × 20.0 μl | N × 20.0 μl | N × 20.0 μl |

N is the number of samples including non-template controls plus 1.

Twenty microliters of each master mix was added into individual wells of a 96 well plate. Then 5 μl of sample (or control) was added to each well. Prior to an rRT-PCR run, the 96 well plate was centrifuged at 500×g for 30 seconds at 4° C. The plate was loaded into a thermocycler and subjected to the PCR cycle as shown in Table 3. Reactions were carried out in a 7500 Fast Dx Real-Time PCR instrument (Applied Biosystems, Foster City, Calif.) or an MX3005 QPCR system (Stratagene, La Jolla, Calif.). The reaction volume was 25 μl.

TABLE 3 rRT-PCR conditions

|  | Invitrogen | Ambion AgPath | Quanta |
| --- | --- | --- | --- |
| Reverse Transcription | 50° C. for 30 min | 50° C. for 30 min | 50° C. for 30 min |
| Taq inhibitor inactivation | 95° C. for 2 min | 95° C. for 10 min | 95° C. for 5 min |
| PCR amplification (45 cycles) | 95° C. for 15 sec | 95° C. for 15 sec | 95° C. for 15 sec |
|  | 55° C. for 30 sec* | 55° C. for 30 sec* | 55° C. for 30 sec* |

*Fluorescence data was collected during the 55° C. incubation step.

Example 2

Detection of Influenza A/H3 Seasonal and Variant Viruses by rRT-PCR

This example describes detection of Influenza A H3 seasonal and variant viruses by rRT-PCR assay.

HA gene sequences of seasonal and variant H3 influenza viruses were compared (FIG. 1). Universal forward and reverse primers were designed to amplify both forms of the virus and probes were designed to discriminate between the seasonal and variant forms of the virus (Table 1). rRT-PCR was performed as described in Example 1 using two seasonal viruses and two variant viruses. The assay also included previously described Influenza A primers (SEQ ID NOs: 37 and 38) and probe (SEQ ID NO: 29) (also described in International Patent Publication No. WO 2007/095155; referred to herein as "Lindstrom"). As shown in Table 4, the assay discriminated between the two forms of the virus.

TABLE 4 rRT-PCR A/H3v and Sea A/H3 assay against influenza A/H3 viruses

|  |  | rRT-PCR Ct value* | | |
| --- | --- | --- | --- | --- |
| Influenza Virus | Type | InfA (Lindstrom) | H3v | Sea H3 |
| A/West_Virginia/06/2011_H3v | A/H3 variant | 19.54 | 19.22 | — |
| A/Indiana/08/2011_H3v | A/H3 variant | 20.48 | 22.36 | — |
| A/Wisconsin/67/2005_vaccine seed | Seasonal A/H3 vaccine seed virus | 13.85 | — | 13.82 |
| A/Perth/16/2009_vaccine seed | Seasonal A/H3 vaccine seed virus | 15.39 | — | 15.10 |

*dash indicates no signal was detected

The limit of detection (LOD) of the seasonal and variant H3 assays were tested (Tables 5 and 6). The LOD was compared to influenza A primers (SEQ ID NOs: 37 and 38) and probe (SEQ ID NO: 29) and H3 primers and probes (forward primer: AAGCATTCCYAATGACAAACC (SEQ ID NO: 92); reverse primer: ATTGCRCCRAATATGC-CTCTAGT (SEQ ID NO: 93); probe: CAGGATCA-CATATGGGSCCTGTCCCAG (SEQ ID NO: 94)) previously disclosed in Lindstrom. As shown in Table 5, the LOD for the H3 variant assay was lower than either the influenza A or previous H3 assay. Table 6 shows that the LOD for the H3 seasonal assay was lower than the previous H3 assay and comparable to the influenza A assay.

TABLE 5

CDC rRT-PCR A/H3v Assay Limit of Detection (LoD) (EID$_{50}$/ml) (N = 5)

|  |  | rRT-PCR result | | |
| --- | --- | --- | --- | --- |
| Influenza A/H3 Variant Virus | Conc. (EID$_{50}$/ml) | H3v | InfA (Lindstrom) | H3 (Lindstrom) |
| A/West_Virginia/06/2011 | $1.6 \times 10^{1.9}$ | 5/5 | 5/5 | <u>5/5</u> |
|  | $3.2 \times 10^{0.9}$ | 5/5 | <u>5/5</u> | 5/5 |
|  | $6.4 \times 10^{0.9}$ | <u>5/5</u> | 4/5 | 2/5 |

Underline: LOD

TABLE 6

CDC rRT-PCR Sea A/H3 Assay Limit of Detection (LoD) (EID$_{50}$/ml) (N = 5)

|  |  | rRT-PCR result | | |
| --- | --- | --- | --- | --- |
| Seasonal Influenza A/H3 Virus | Conc. (EID$_{50}$/ml) | H3Sea | InfA (Lindstrom) | H3 (Lindstrom) |
| A/Perth/16/2009 | $4 \times 10^{2.2}$ | 5/5 | 5/5 | <u>5/5</u> |
|  | $8 \times 10^{1.2}$ | 5/5 | <u>5/5</u> | 3/5 |

Underline: LOD

Example 3

Detection of Influenza A/H5N1 Viruses by rRT-PCR

This example describes detection of Influenza A H5/N1 viruses by rRT-PCR assay.

Figure 2:
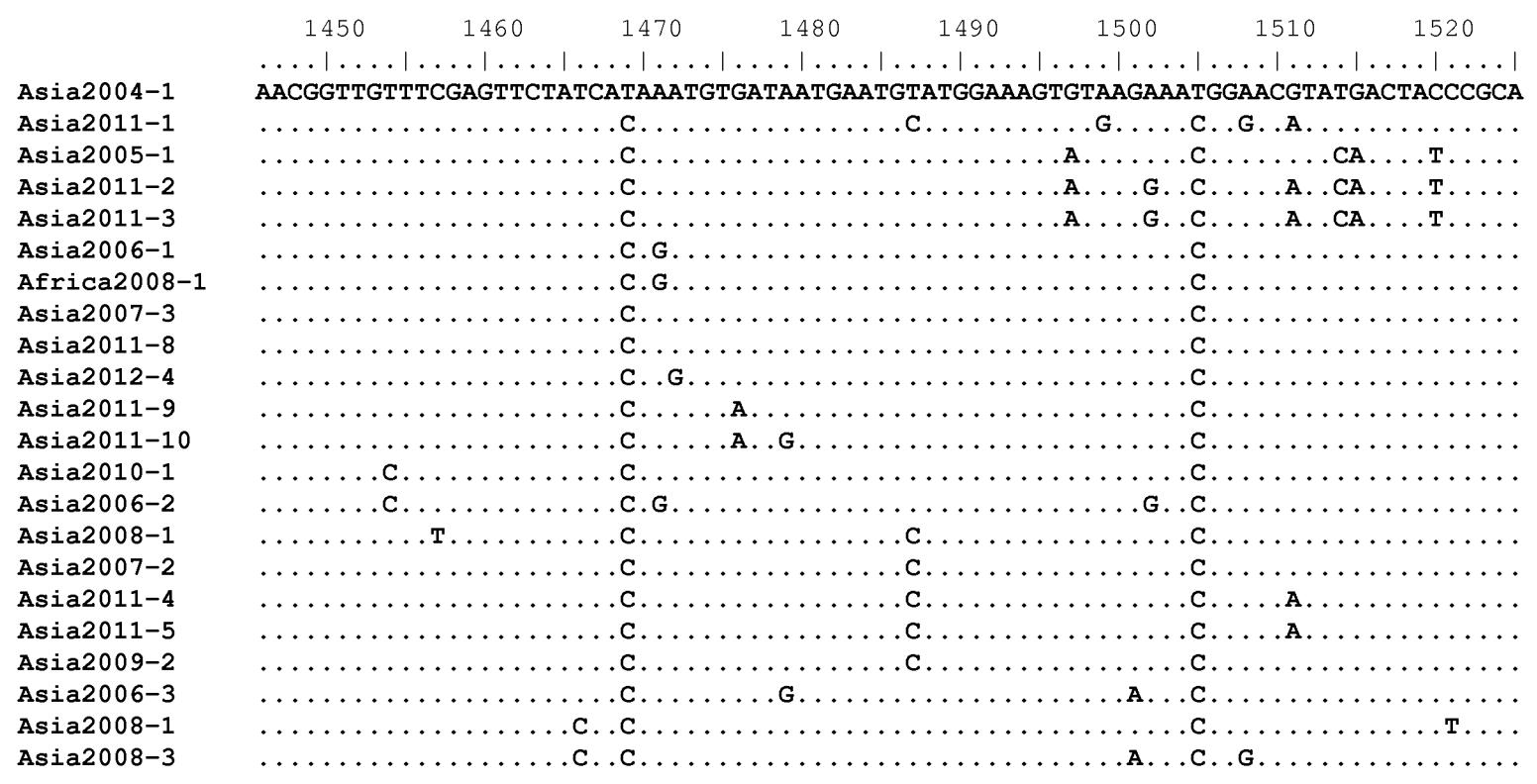
Figure 2:
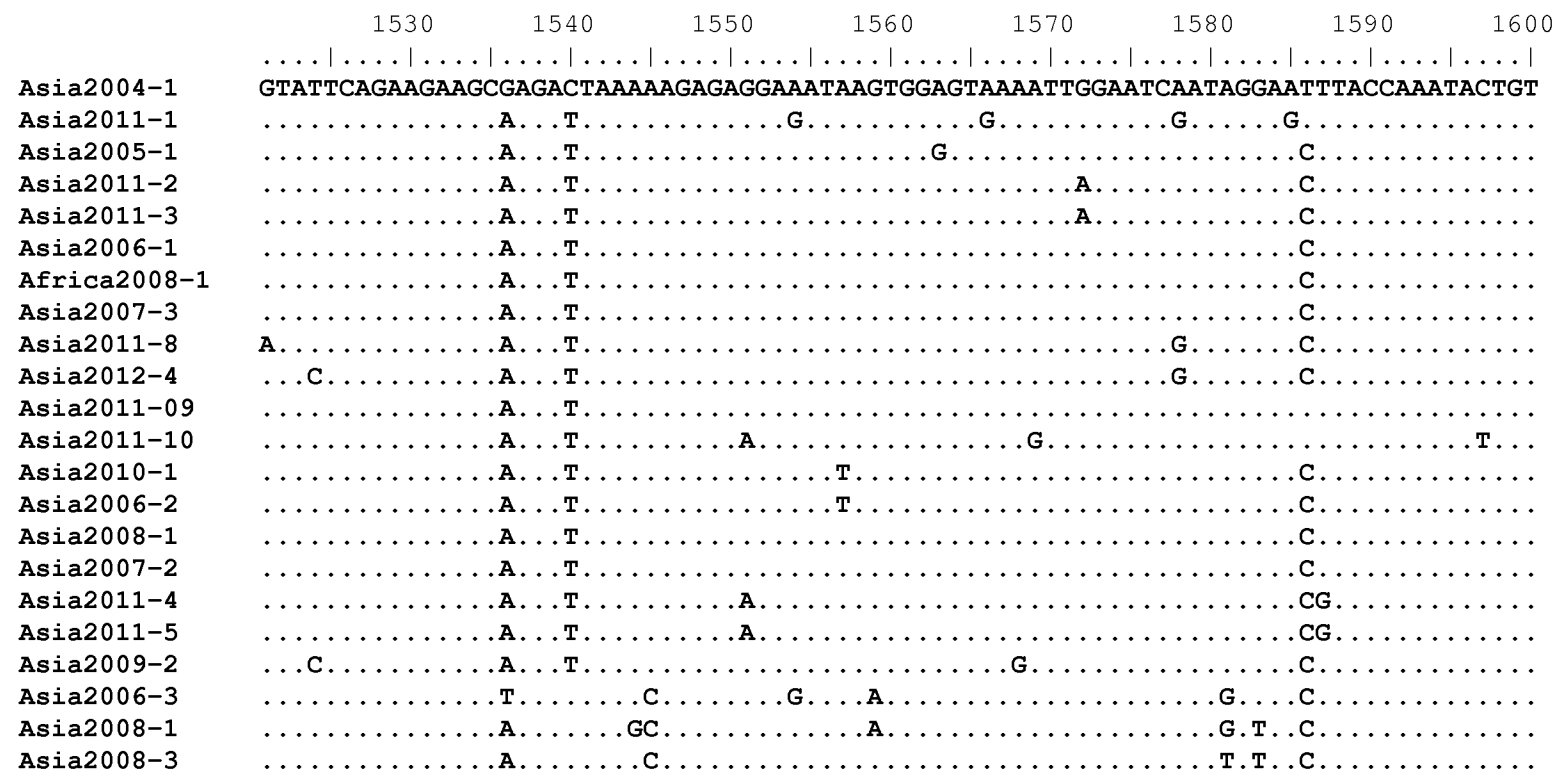
Figure 2:
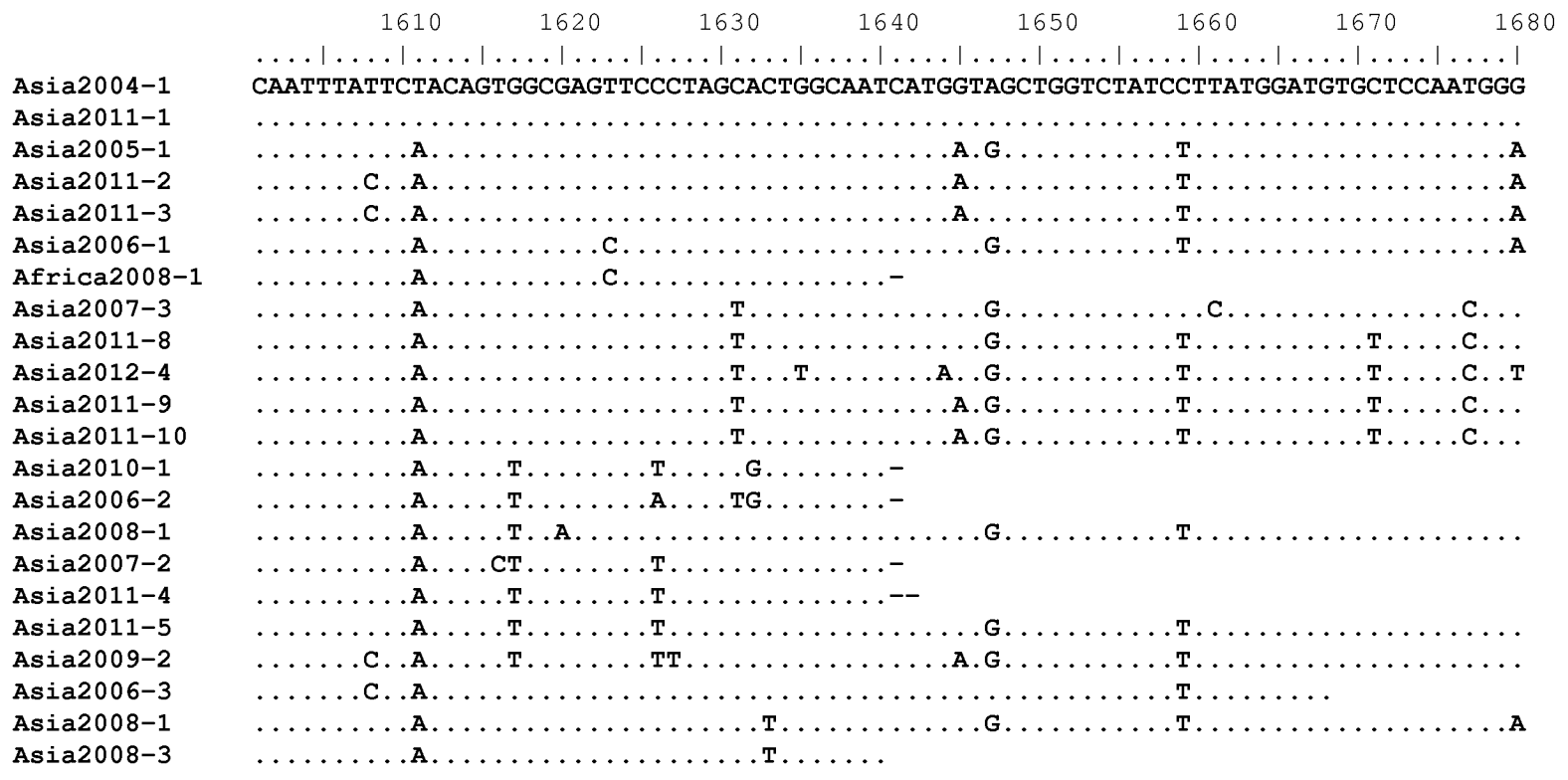

HA gene sequences of H5 influenza viruses were compared (FIGS. 2 and 3). Forward and reverse primers and probes were designed to amplify and detect two different regions of the H5 gene (Table 1). The assay evaluated detection of influenza A viruses from various clades using the H5a (SEQ ID NOs: 5-9) and H5b (SEQ ID NOs: 11-13)

primers and probes described in Example 1, previously described H5a and H5b primers and probes (H5a forward primer: TGGAAAGTRTAARAAACGGAACGT (SEQ ID NO: 95); H5a reverse primer: YGCTAGGGARCTCGC-CACTG (SEQ ID NO: 96); H5a probe: TGACTAC-CCGCAGTATTCAGAAGAAGCAAGACTAA (SEQ ID NO: 97); H5b forward primer: GGAATGYCCCAAATAT-GTGAAATCAA (SEQ ID NO: 98); H5b reverse primer: CCACTCCCCTGCTCRTTGCT (SEQ ID NO: 99); H5b probe: TACCCATACCAACCATCTACCATTCCCTGC-CAT (SEQ ID NO: 100), all described in Lindstrom), and previously described Influenza A primers and probe (SEQ ID NOs: 37, 38 and 29, respectively, also described in Lindstrom). The data are provided in Tables 7 and 8. The performance of the assay was evaluated by LOD against HA of emerging genetic clades. The H5a and H5b primers and probes described herein showed increased sensitivity (decreased Ct values) compared to the previous primers and probes with respect to samples from clades 1.1, 2.1.3, 2.2.2, 2.3.4 (H5a) and clades 1, 1.1, 2.1, 2.3.2.1, 2.3.4, and 7.1 (H5b).

TABLE 7 rRT-PCR H5a assay analytical sensitivity (inclusivity) with highly pathogenic avian influenza A/H5N1 viruses

| Influenza A/ H5N1 viruses | Clade | rRt-PCR Ct value | | |
|---|---|---|---|---|
| | | H5a (Lindstrom) | H5a | InfA (Lindstrom) |
| Asia2004-1 | 1 | 30.19 | 30.35 | 30.08 |
| Asia2007-1 | 1.1 | 29.31 | 27.64* | 27.65 |
| Asia2011-1 | 1.1 | 15.99 | 11.59* | 12.47 |
| Asia2005-1 | 2.1 | 29.35 | 30.00 | 30.23 |
| Asia2011-2 | 2.1.3 | 14.24 | 11.97* | 11.04 |
| Asia2011-3 | 2.1.3 | 13.12 | 11.06* | 9.62 |
| Asia2012-1 | 2.1.3 | 22.84 | 22.43 | 19.87 |
| Asia2006-1 | 2.2 | 29.75 | 28.79 | 29.66 |
| Africa2008-1 | 2.2.1 | 15.42 | 16.26 | 15.37 |
| Asia2011-4 | 2.2.2 | 13.55 | 11.73* | 12.16 |
| Asia2006-2 | 2.3.4 | 30.98 | 21.89* | 22.36 |
| Asia2007-2 | 2.3.4 | 23.62 | 14.00* | 13.27 |
| Asia2008-1 | 2.3.4 | 18.46 | 15.72* | 12.40 |
| Asia2009-1 | 2.3.4 | 19.86 | 12.52* | 13.01 |
| Asia2007-3 | 2.3.2.1 | 13.58 | 12.65 | 13.84 |

TABLE 7-continued rRT-PCR H5a assay analytical sensitivity (inclusivity) with highly pathogenic avian influenza A/H5N1 viruses

| Influenza A/ H5N1 viruses | Clade | rRt-PCR Ct value | | |
|---|---|---|---|---|
| | | H5a (Lindstrom) | H5a | InfA (Lindstrom) |
| Asia2010-1 | 2.3.4.1 | 16.80 | 16.20 | 15.56 |
| Asia2011-5 | 2.3.4.2 | 12.56 | 11.28 | 10.46 |
| Asia2006-3 | 4 | 21.93 | 20.58 | 22.21 |
| Asia2008-1 | 7.1 | 22.48 | 23.05 | 23.92 |

*Substantial improvement over previous assay (Lindstrom)

TABLE 8 rRT-PCR H5b assay analytical sensitivity (inclusivity) with highly pathogenic avian influenza A/H5N1 viruses

| Influenza A/ H5N1 viruses | Clade | rRt-PCR Ct value | | |
|---|---|---|---|---|
| | | H5b (Lindstrom) | H5b | InfA (Lindstrom) |
| Asia2004-1 | 1 | 23.90 | 20.58* | 21.65 |
| Asia2012-2 | 1.1 | 25.25 | 25.64 | 22.99 |
| Asia2012-3 | 1.1 | 14.28 | 14.76 | 13.81 |
| Asia2005-1 | 2.1 | 26.63 | 22.28* | 22.05 |
| Asia2012-1 | 2.1.3 | 14.61 | 12.89 | 12.57 |
| Asia2006-1 | 2.2 | 28.91 | 26.17 | 24.69 |
| Africa2008-2 | 2.2.1 | 22.14 | 21.88 | 21.02 |
| Africa2012-1 | 2.2.1 | 21.41 | 21.39 | 20.33 |
| Asia2011-5 | 2.2.2 | 31.78 | 31.99 | 30.28 |
| Asia2011-7 | 2.2.2 | 30.52 | 30.23 | 28.35 |
| Asia2012-2 | 2.3.2.1 | 25.94 | 26.00 | 23.90 |
| Asia2012-3 | 2.3.2.1 | 31.66 | 31.38 | 29.60 |
| Asia2007-3 | 2.3.2.1 | 27.77 | 24.89* | 22.48 |
| Asia2006-2 | 2.3.4 | 31.00 | 27.90* | 26.71 |
| Asia2010-1 | 2.3.4.1 | 13.13 | 10.84 | 11.49 |
| Asia2006-3 | 4 | 31.83 | 28.59 | 27.80 |
| Asia2008-1 | 7.1 | 30.76 | 27.70* | 25.90 |

*Substantial improvement over previous assay (Lindstrom)

The sensitivity of the assay was also tested with varying concentrations of qualified highly pathogenic influenza A/H5N1 viruses. As shown in Table 9, the H5a assay disclosed herein showed improved sensitivity for an influenza A/H5N1 virus from clade 2.3.4.3 compared to the Lindstrom H5a and H5b and influenza A assays.

TABLE 9 rRT-PCR A/H5 assay analytical sensitivity (inclusivity) with qualified highly pathogenic avian influenza A/H5N1 viruses (n = 3)

| Virus | Clade | Conc. ($EID_{50}$/ml) | rRT-PCR Ct value (mean) | | | | |
|---|---|---|---|---|---|---|---|
| | | | H5a Lindstrom | H5a | H5b Lindstrom | H5b | InfA Lindstrom |
| Asia2011-8 | 2.3.2.1 (Barn-SW-like) | $10^{3.83}$ | 27.31 | 28.43 | 29.1 | 29.37 | 29.61 |
| Asia2012-4 | 2.3.2.1 (Barn-SW-like) | $10^{3.50}$ | 32.74 | 34.48 | 32.54 | 32.39 | 36.11 |
| Asia2011-9 | 2.3.2.1 (Hubei-like) | $10^{3.83}$ | 29.55 | 30.53 | 31.16 | 31.36 | 31.99 |
| Asia2011-10 | 2.3.2.1 (Hubei-like) | $10^{3.50}$ | 29.68 | 30.59 | 36.45 | 35.41 | 30.7 |
| Asia2011-5 | 2.3.4.2 | $10^{3.75}$ | 32.81 | 32.54 | 33.96 | 33.37 | 33.08 |
| Asia2009-2 | 2.3.4.3 | $10^{3.25}$ | 37.83 | 31.63* | 38.01 | 36.93 | 32.52 |
| Asia2008-3 | 7.2 | $10^{3.50}$ | 26.75 | 28.01 | 37.08 | 35.02 | 30.17 |

Example 4

Detection of H7 Influenza Virus by rRT-PCR

This example describes detection of Eurasian and North American H7 influenza viruses by rRT-PCR assay.

HA gene sequences of Eurasian H7 influenza viruses (FIG. 4) and North American H7 influenza viruses (FIG. 5) were compared. Forward and reverse primers were designed to amplify the viruses and a probes were designed (Table 1). rRT-PCR assays were performed as described in Example 1 using the primers and probe disclosed herein. In some cases, the assay also included previously described Eurasian H7 primers and probe (forward primer: GCTTCAGGCAT-CAAAATGCACAAGG (SEQ ID NO: 101); reverse primer: CATTGCTACYAAGAGTTCAGCRT (SEQ ID NO: 102); probe ACCACACTTCTGTCATGGAATCTCTGGTCCA (SEQ ID NO: 103)) or North American H7 primers (SEQ ID NOs: 47 and 48) and probe (SEQ ID NO: 34) and Influenza A primers (SEQ ID NOs: 37 and 38) and probe (SEQ ID NO: 29) (all described in Lindstrom et al.). Performance was evaluated by LOD against HA gene of Eurasian H7 viruses or North American H7 viruses. As shown in Table 10, the primers and probe described herein resulted in improved sensitivity for two of the Eurasian H7 viruses. As shown in Table 11, the primers and probe described herein resulted in improved sensitivity for four of the six tested North American H7 viruses.

TABLE 10

CDC rRT-PCR Eu A/H7 assay analytical sensitivity (inclusivity) with qualified Eurasian influenza A/H7 viruses (N = 3)

| Influenza A/H7 viruses | Conc. (EID$_{50}$/ml) | rRt-PCR Ct value (mean) | | |
|---|---|---|---|---|
| | | EuH7 (Lindstrom) | EuH7 | InfA (Lindstrom) |
| Asia2013-1 (H7N9) | $10^{4.0}$ | 32.71 | 30.71* | 28.89 |
| Asia2009-1 (H7N3) | $10^{4.1}$ | 33.56 | 31.82* | 33.98 |
| Africa2007-1 (H7N3) | $10^{3.5}$ | 31.85 | 32.52 | 34.48 |
| Europe2007-1 (H7N3) | $10^{2.9}$ | 31.16 | 31.04 | 32.06 |
| Europe2000-1 (H7N3) | $10^{4.5}$ | 27.32 | 27.87 | 29.38 |

*Improvement over previous assay (Lindstrom)

TABLE 11

CDC rRT-PCR NA H7 assay analytical sensitivity (inclusivity) against North American lineage A/H7 influenza viruses (N = 3)

| Influenza A/ H7 viruses | Conc. (EID$_{50}$/ml) | rRt-PCR Ct value (mean) | | |
|---|---|---|---|---|
| | | NA H7 (Lindstrom) | NA H7 | InfA (Lindstrom) |
| North America2008-1 (H7N3) | $10^{6.9}$ | 33.75 | 21.35* | 23.7 |
| North America2012-1 (H7N3) | $10^{6.2}$ | 38.1 | 22.32* | 23.8 |
| North America2011-1 (H7N9) | | 35.41 | 21.34* | 24.01 |
| North America2011-2 (H7N9) | | 29.92 | 14.25* | 16.98 |
| North America2009-1 (H7N9) | | 27.59 | 14.038* | 14.29 |
| North America2003-1 (H7N2) | | 18.17 | 18.35 | 19.19 |

*Improvement over previous assay (Lindstrom)

Example 5

Detection of H9 Influenza Virus by rRT-PCR

This example describes detection of H9 influenza viruses by rRT-PCR assay.

HA gene sequences of H9 influenza viruses were compared (FIG. 6). Forward and reverse primers were designed to amplify the viruses and a probes were designed (Table 1). rRT-PCR assays were performed as described in Example 1 using the primers and probe disclosed herein. In some cases, the assay also included previously described H9 primers (SEQ ID NOs: 49 and 50) and probe (SEQ ID NO: 35) and Influenza A primers (SEQ ID NOs: 37 and 38) and probe (SEQ ID NO: 29) (all described in Lindstrom et al.). Performance was evaluated by LOD against HA gene of H9 viruses. As shown in Table 12, the primers and probe described herein resulted in improved sensitivity for six of the seven tested viruses.

TABLE 12

CDC rRT-PCR H9 assay analytical sensitivity (inclusivity) against influenza A/H9 viruses (N = 3)

| Influenza A/ H9 viruses | Conc. (EID$_{50}$/ml) | rRt-PCR Ct value (mean) | | |
|---|---|---|---|---|
| | | H9 (Lindstrom) | H9 | InfA (Lindstrom) |
| Asia2011-1 (H9N2) | $10^{7.5}$ | 23.06 | 21.16* | 21.1 |
| Asia2012-1 (H9N2) | | 14.69 | 13.47* | 12.22 |
| Asia2009-1 (H9N2) | $10^{6.5}$ | 23.74 | 21.89* | 22.67 |
| Asia2012-2 (H9N2) | | 17.21 | 16.11* | 16.55 |
| Asia2009-2(H9N2) | $10^{5.4}$ | 20.15 | 18.02* | 17.36 |
| Asia2008-1 (H9N2) | $10^{6.9}$ | 20.1 | 20.1 | 20.74 |
| Asia2006-1 (H9N2) | $10^{7.1}$ | 25.95 | 24.32* | 22.26 |

*Improvement over previous assay (Lindstrom)

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A set of primers for the amplification of an influenza virus nucleic acid, comprising at least two primers consisting of the nucleic acid sequence of any one of SEQ ID NO: 5, SEQ ID NO: 6, SEQ ID NO: 7, SEQ ID NO: 8, SEQ ID NO: 11, SEQ ID NO: 12, SEQ ID NO: 107, or SEQ ID NO: 108.

2. The set of primers of claim 1, wherein the set comprises:

one or more forward primers consisting of the nucleic acid sequence of any one of SEQ ID NO: 5, SEQ ID NO: 6, SEQ ID NO: 11, or SEQ ID NO: 107; and one or more reverse primers consisting of the nucleic acid sequence of any one of SEQ ID NO: 7, SEQ ID NO: 8, SEQ ID NO: 12, or SEQ ID NO: 108, wherein the set of primers is capable of hybridizing to and directing the amplification of the influenza virus nucleic acid.

3. The set of primers of claim 2, wherein the forward and reverse primers are a pair of primers, and wherein the pair of primers:

(a) is specific for the amplification of influenza subtype H5 and the set comprises:

(i) a forward primer consisting of SEQ ID NO: 5 or SEQ ID NO: 6 and a reverse primer consisting of SEQ ID NO: 7 or SEQ ID NO: 8; or (ii) a forward primer consisting of SEQ ID NO: 11 and a reverse primer consisting of SEQ ID NO: 12;

(b) is specific for influenza subtype H9 and comprises a forward primer consisting of SEQ ID NO: 107 and a reverse primer consisting of SEQ ID NO: 108.

4. The set of primers of claim 1, further comprising at least one primer comprising or consisting of the nucleic acid sequence set forth as any one of SEQ ID NOs: 1, 2, 14, 15, 37-52, 92, 93, 95, 96, 98, 99, 101, 102, 104, or 105.

5. A kit for detecting an influenza virus nucleic acid in a sample, comprising:

at least one probe consisting of the nucleic acid sequence of SEQ ID NO: 9, SEQ ID NO: 13, or SEQ ID NO: 109, and at least one attached label, wherein the at least one attached label is a radioactive isotope, enzyme substrate, co-factor, ligand, chemiluminescent agent, fluorophore, fluorescence quencher, hapten, enzyme, or combinations thereof; and (i) at least one pair of primers comprising a forward primer consisting of SEQ ID NO: 5 or SEQ ID NO: 6 and a reverse primer consisting of SEQ ID NO: 7 or SEQ ID NO: 8;

(ii) at least one pair of primers comprising a forward primer consisting of SEQ ID NO: 11 and a reverse primer consisting of SEQ ID NO: 12;

(iii) at least one pair of primers comprising a forward primer consisting of SEQ ID NO: 107 and a reverse primer consisting of SEQ ID NO: 108.

6. The kit of claim 5, further comprising at least one probe comprising or consisting of the nucleic acid sequence set forth as any one of SEQ ID NOs: 3, 4, 10, 16, 29, 30, 31, 32, 33, 34, 35, 94, 97, 100, 103 or 106.

7. The kit of claim 5, further comprising at least one primer comprising or consisting of the nucleic acid sequence set forth as any one of SEQ ID NOs: 1, 2, 14, 15, 37, 38, 39, 40, 41, 42, 43, 44, 45, 46, 47, 48, 49, 50, 92, 93, 95, 96, 98, 99, 101, 102, 104, or 105.

8. A method for detecting an influenza virus nucleic acid in a sample, comprising:

contacting the sample with one or more of the probes and the pairs of primers of the kit of claim 5;

amplifying the influenza virus nucleic acid by polymerase chain reaction (PCR), real-time PCR, reverse transcriptase-PCR, real-time reverse transcriptase-PCR, ligase chain reaction, or transcription-mediated amplification; and detecting hybridization between the amplified influenza virus nucleic acid and the one or more probes.

9. The method of claim 8, further comprising discriminating between presence of an influenza virus H5 subtype nucleic acid and/or an influenza virus subtype H9 nucleic acid.

10. The method of claim 8, wherein the probe and the pair of primers consists of:

a probe consisting of the nucleic acid sequence of SEQ ID NO: 9, a forward primer consisting of SEQ ID NO: 5 or SEQ ID NO: 6, and a reverse primer consisting of SEQ ID NO: 7 or SEQ ID NO: 8, or a probe consisting of the nucleic acid sequence of SEQ ID NO: 13, a forward primer consisting of SEQ ID NO: 11, and a reverse primer consisting of SEQ ID NO: 12, and hybridization of the probe to the influenza virus nucleic acid indicates the presence of influenza subtype H5 in the sample; and/or a probe consisting of the nucleic acid sequence of SEQ ID NO: 109, a forward primer consisting of SEQ ID NO: 107, and a reverse primer consisting of SEQ ID NO: 108, and hybridization of the probe to the influenza virus nucleic acid indicates the presence of influenza subtype H9 in the sample.

11. The method of claim 8, further comprising contacting the sample with at least one probe comprising or consisting of the nucleic acid sequence set forth as SEQ ID NO: 3, 4, 10, 16, 29, 30, 31, 32, 33, 34, 35, 36, 94, 97, 100, 103, or 106.

12. The method of claim 8, further comprising contacting the sample with at least one primer comprising or consisting of the nucleic acid sequence set forth as any one of SEQ ID NOs: 1, 2, 14, 15, 37-52, 92, 93, 95, 96, 98, 99, 101, 102, 104, or 105.

13. The method of claim 8, wherein the sample comprises a biological sample obtained from a subject or an environmental sample.

14. The method of claim 13, wherein the biological sample obtained from the subject comprises bronchoalveolar lavage, tracheal aspirate, sputum, nasopharyngeal aspirate, oropharyngeal aspirate, or saliva.

* * * * *

SEQUENCE LISTING

<160> NUMBER OF SEQ ID NOS: 122

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide - H3 Universal
      forward

<400> SEQUENCE: 1
gatctyaaaa gcactcargc agc                                              23

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide - H3 Universal
      reverse

<400> SEQUENCE: 2
aggtcctgaa ttctyccttc kac                                              23

<210> SEQ ID NO 3
<211> LENGTH: 53
<212> TYPE: DNA
<213> ORGANISM: Artificial Sequence
<220> FEATURE:
<223> OTHER INFORMATION: Synthetic oligonucleotide - H3 seasonal probe

<400> SEQUENCE: 3
gatctyaaaa gcactcargc agctcccgat caayckattc agcttcccat tga             53

<210> SEQ ID NO 4
<211> LENGTH: 29
<212> TYPE: DNA
<213> ORGANISM: Artificial Sequence
<220> FEATURE:
<223> OTHER INFORMATION: Synthetic oligonucleotide - H3 variant probe

<400> SEQUENCE: 4
tcttgattac tctrttyagt ttcccggtg                                        29

<210> SEQ ID NO 5
<211> LENGTH: 25
<212> TYPE: DNA
<213> ORGANISM: Artificial Sequence
<220> FEATURE:
<223> OTHER INFORMATION: synthetic oligonucleotide - H5a forward 1

<400> SEQUENCE: 5
tggaaagtgt ragaaacggr acrta                                            25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide - H5a forward 2

<400> SEQUENCE: 6
tggaaagtat aagraacgga acrta                                            25

<210> SEQ ID NO 7
<211> LENGTH: 22

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide - H5a reverse 1

<400> SEQUENCE: 7
ctagggarct cgccactgtw ga                                          22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide - H5a reverse 2

<400> SEQUENCE: 8
ctagdgaact cgcarctgtt ga                                          22

<210> SEQ ID NO 9
<211> LENGTH: 35
<212> TYPE: DNA
<213> ORGANISM: Artificial Sequence
<220> FEATURE:
<223> OTHER INFORMATION: Synthetic oligonucleotide - H5a probe 1

<400> SEQUENCE: 9
tgactacccg cagtattcag aagaakcaag aytaa                            35

<210> SEQ ID NO 10
<211> LENGTH: 35
<212> TYPE: DNA
<213> ORGANISM: Artificial Sequence
<220> FEATURE:
<223> OTHER INFORMATION: Synthetic oligonucleotide - H5a probe 2

<400> SEQUENCE: 10
caactatccg cagtattcag aagaagcaag attaa                            35

<210> SEQ ID NO 11
<211> LENGTH: 26
<212> TYPE: DNA
<213> ORGANISM: Artificial Sequence
<220> FEATURE:
<223> OTHER INFORMATION: Synthetic oligonucleotide - H5b forward

<400> SEQUENCE: 11
ggaatgyccc aaatatgtga aatcaa                                      26

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide - H5b reverse

<400> SEQUENCE: 12
ccrctcccct gctcrttrct                                             20

<210> SEQ ID NO 13
<211> LENGTH: 33
<212> TYPE: DNA
<213> ORGANISM: Artificial Sequence
<220> FEATURE:
<223> OTHER INFORMATION: Synthetic oligonucleotide - H5b probe

<400> SEQUENCE: 13

```
tacccatacc aaccatctac catyccctgc cat                              33
```

<210> SEQ ID NO 14
<211> LENGTH: 23
<212> TYPE: DNA
<213> ORGANISM: Artificial Sequence
<220> FEATURE:
<223> OTHER INFORMATION: Synthetic oligonucleotide - EuH7 forward

<400> SEQUENCE: 14

```
aatgcacarg grgagggaac tgc                                         23
```

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide - EuH7 reverse

<400> SEQUENCE: 15

```
cattgctacy aagagttcag crtt                                        24
```

<210> SEQ ID NO 16
<211> LENGTH: 31
<212> TYPE: DNA
<213> ORGANISM: Artificial Sequence
<220> FEATURE:
<223> OTHER INFORMATION: Synthetic oligonucleotide - EuH7 probe

<400> SEQUENCE: 16

```
accacacytc tgtyatrgaa tctctggtcc a                                31
```

<210> SEQ ID NO 17
<211> LENGTH: 240
<212> TYPE: DNA
<213> ORGANISM: Influenza A virus

<400> SEQUENCE: 17

```
ctgaaggcac aggacaagca gcagatctta aaagcactca agcagcaatc aaccaaatca    60
ccgggaaact aaatagagta atcaagaaaa cgaacgagaa attccatcaa atcgaaaaag   120
aattctcaga agtagaaggg agaattcagg acctagagaa atacgttgaa gacactaaaa   180
tagatctctg gtcttacaac gctgagcttc ttgttgccct ggagaaccaa catacaattg   240
```

<210> SEQ ID NO 18
<211> LENGTH: 240
<212> TYPE: DNA
<213> ORGANISM: Influenza A virus

<400> SEQUENCE: 18

```
ctgaaggcac aggacaagca gcagatctta aaagcactca agcagcaatc aaccaaatca    60
ccgggaaact aaatagagta atcaagaaaa caaacgagaa attccatcaa atcgaaaaag   120
aattctcaga agtagaagga agaattcagg acctagagaa atacgttgaa gacactaaaa   180
tagatctctg gtcttacaac gctgagattc ttgttgccct ggagaaccaa catacaattg   240
```

<210> SEQ ID NO 19
<211> LENGTH: 240
<212> TYPE: DNA
<213> ORGANISM: Influenza A virus

<400> SEQUENCE: 19

```
ctgagggaat aggacaagca gcagatctca aaagcactca agcagcaatc aatcaaatca    60
```
atgggaagct gaataggttg atcgggaaaa ccaacgagaa attccatcag attgaaaaag 120
aattctcaga agtagaaggg agaattcagg acctcgagaa atatgttgag gacactaaaa 180
tagatctctg gtcatacaac gcggagcttc ttgttgccct ggagaaccaa catacaattg 240

<210> SEQ ID NO 20
<211> LENGTH: 240
<212> TYPE: DNA
<213> ORGANISM: Influenza A virus

<400> SEQUENCE: 20
ctgagggaat aggacaagca gcagatctca aaagcactca agcagcaatc gatcaaatca 60
atgggaagct gaataggttg atcgggaaaa ccaacgagaa attccatcag attgaaaaag 120
aattctcaga agtcgaaggg agaattcagg accttgagaa atatgttgag gacaccaaaa 180
tagatctctg gtcatacaac gcggagcttc ttgttgccct ggagaaccaa catacaattg 240

<210> SEQ ID NO 21
<211> LENGTH: 240
<212> TYPE: DNA
<213> ORGANISM: Influenza A virus

<400> SEQUENCE: 21
ctgagggaag aggacaagca gcagatctca aaagcactca agcagcaatc gatcaaatca 60
atgggaagct gaatagattg atcgggaaaa ccaacgagaa attccatcag attgaaaaag 120
aattctcaga agtcgaaggg agaattcagg accttgagaa atatgttgag gacactaaaa 180
tagatctctg gtcatacaac gcggagcttc ttgttgccct ggagaaccaa catacaattg 240

<210> SEQ ID NO 22
<211> LENGTH: 240
<212> TYPE: DNA
<213> ORGANISM: Influenza A virus

<400> SEQUENCE: 22
ctgagggaag aggacaagca gcagatctca aaagcactca agcagcaatc gatcaaatca 60
atgggaagct gaatcgattg atcgggaaaa ccaacgagaa attccatcag attgaaaaag 120
aattctcaga agtcgaaggg agaattcagg accttgagaa atatgttgag gacactaaaa 180
tagatctctg gtcatacaac gcggagcttc ttgttgccct ggagaaccaa catacaattg 240

<210> SEQ ID NO 23
<211> LENGTH: 320
<212> TYPE: DNA
<213> ORGANISM: Influenza A virus

<400> SEQUENCE: 23
aggcctattt ggtgctatag cgggtttcat tgaaaatgga tgggaaggcc taattgatgg 60
ttggtatggt ttcagacacc agaatgcaca gggagaggga actgctgcag attacaaaag 120
cactcaatcg gcaattgatc aaataacagg aaaattaaac cggcttatag aaaaaaccaa 180
ccaacaattt gagttgatag acaatgaatt caatgaggta gagaagcaaa tcggtaatgt 240
gataaattgg accagagatt ctataacaga agtgtggtca tacaatgctg aactcttggt 300
agcaatggag aaccagcata 320

<210> SEQ ID NO 24
<211> LENGTH: 320
<212> TYPE: DNA

<213> ORGANISM: Influenza A virus

<400> SEQUENCE: 24

```
aggcctattt ggtgctatag cgggtttcat tgaaaatgga tgggaaggcc taattgatgg     60
ttggtatggt ttcagacacc agaatgcaca gggagaggga actgctgcag attacaaaag    120
cactcaatcg gcaattgatc aaataacagg aaaattaaac cggcttatag aaaaaaccaa    180
ccaacaattt gagttgatag acaatgaatt cactgaggta gagaagcaaa tcggtaatgt    240
gataaattgg accagagatt ctataacaga agtgtggtca tacaatgctg aactcttggt    300
agcaatggag aaccagcata                                                320
```

<210> SEQ ID NO 25
<211> LENGTH: 320
<212> TYPE: DNA
<213> ORGANISM: Influenza A virus

<400> SEQUENCE: 25

```
aggcctgttt ggtgccatag caggttttat tgaaaacgga tgggaaggtc tgattgatgg     60
atggtatggc ttcagacatc aaaacgcaca aggagaagga actgctgcag attacaagag    120
cactcaatca gcaattgatc aaataacagg aaagttaaat cgactcatag aaaaaaccaa    180
tcaacaattt gagttgatag acaatgagtt cactgaggtt gaaaagcaga ttggcaatgt    240
gataaattgg accagagatt ctataacaga ggtgtggtca tacaatgctg aactcttagt    300
agcaatggag aaccagcaca                                                320
```

<210> SEQ ID NO 26
<211> LENGTH: 320
<212> TYPE: DNA
<213> ORGANISM: Influenza A virus

<400> SEQUENCE: 26

```
aggcctattt ggtgccatag cgggtttcat tgaaaatgga tgggaaggtc tgattgacgg     60
gtggtatggc ttcaggcatc aaaatgcaca aggggagggg actgctgcag attacaaaag    120
cacccaatca gcaattgatc aaataacagg aaaattaaac cggcttattg aaaaaactaa    180
ccaacaattt gagttgatag acaatgagtt cactgaggtt gaaaagcaaa ttggcaatgt    240
gataaattgg accagagatt ccatgacaga agtgtggtcc tataacgctg aactcttggt    300
agcaatggag aatcagcaca                                                320
```

<210> SEQ ID NO 27
<211> LENGTH: 320
<212> TYPE: DNA
<213> ORGANISM: Influenza A virus

<400> SEQUENCE: 27

```
aggcctattt ggtgctatag cgggtttcat tgaaaacgga tgggaaggtc tgattgacgg     60
gtggtatggc ttcaggcatc agaatgcaca aggggaggga actgctgcag attacaaaag    120
cacccaatca gcaattgatc agataacagg gaaattaaac cggcttatag aaaaaactaa    180
ccaacaattc gagttaatag ataatgaatt cactgaggtt gaaagacaaa ttggcaatgt    240
gataaattgg accagagatt ccatgacaga agtgtggtcc tataacgctg aactcttggt    300
agcaatggag aatcagcaca                                                320
```

<210> SEQ ID NO 28
<211> LENGTH: 320

<212> TYPE: DNA
<213> ORGANISM: Influenza A virus

<400> SEQUENCE: 28

```
aggcctattt ggtgctatag cgggtttcat tgaaaatgga tgggaaggtc tgattgatgg      60
gtggtatggc ttcaggcatc aaaatgcaca aggggaggga actgctgcag attacaaaag     120
cacccaatca gcaattgatc aaataacagg aaaattaaac cggcttatag aaaaaactaa     180
ccaacaattt gagttaatag acaatgaatt cactgaggtt gaaaagcaaa ttggcaatgt     240
gataaattgg accagagatt ccatgacaga agtgtggtcc tataacgctg aactcttggt     300
agcaatggag aatcagcaca                                                 320
```

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide - influenza A probe

<400> SEQUENCE: 29

```
tgcagtcctc gctcactggg cacg                                             24
```

<210> SEQ ID NO 30
<211> LENGTH: 29
<212> TYPE: DNA
<213> ORGANISM: Artificial Sequence
<220> FEATURE:
<223> OTHER INFORMATION: Synthetic oligonucleotide - influenza A
      pandemic 2009 probe

<400> SEQUENCE: 30

```
tgaatgggtc tatcccgacc agtgagtac                                        29
```

<210> SEQ ID NO 31
<211> LENGTH: 27
<212> TYPE: DNA
<213> ORGANISM: Artificial Sequence
<220> FEATURE:
<223> OTHER INFORMATION: Synthetic oligonucleotide - influenza type B
      probe

<400> SEQUENCE: 31

```
ccaattcgag cagctgaaac tgcggtg                                          27
```

<210> SEQ ID NO 32
<211> LENGTH: 30
<212> TYPE: DNA
<213> ORGANISM: Artificial Sequence
<220> FEATURE:
<223> OTHER INFORMATION: Synthetic oligonucleotide - influenza H1 probe

<400> SEQUENCE: 32

```
tgayccaaag cctctactca gtgcgaaagc                                       30
```

<210> SEQ ID NO 33
<211> LENGTH: 29
<212> TYPE: DNA
<213> ORGANISM: Artificial Sequence
<220> FEATURE:
<223> OTHER INFORMATION: Synthetic oligonucleotide - influenza H1
      pandemic 2009 probe

<400> SEQUENCE: 33

```
atacatccga tcacmattgg aaaatgtcc                                        29
```

<210> SEQ ID NO 34
<211> LENGTH: 35
<212> TYPE: DNA
<213> ORGANISM: Artificial Sequence
<220> FEATURE:
<223> OTHER INFORMATION: Synthetic oligonucleotide - influenza North
    American H7 probe

<400> SEQUENCE: 34
aaagcaccca rtctgcaata gatcagatca caggc        35

<210> SEQ ID NO 35
<211> LENGTH: 29
<212> TYPE: DNA
<213> ORGANISM: Artificial Sequence
<220> FEATURE:
<223> OTHER INFORMATION: Synthetic oligonucleotide - influenza H9 probe

<400> SEQUENCE: 35
ccagaacarg aaggcagcaa accccattg        29

<210> SEQ ID NO 36
<211> LENGTH: 23
<212> TYPE: DNA
<213> ORGANISM: Artificial Sequence
<220> FEATURE:
<223> OTHER INFORMATION: Synthetic oligonucleotide - human RNase P probe

<400> SEQUENCE: 36
ttctgacctg aaggctctgc gcg        23

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide - influenza A forward

<400> SEQUENCE: 37
gaccratcct gtcacctctg ac        22

<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide - influenza A reverse

<400> SEQUENCE: 38
agggcattyt ggacaaakcg tcta        24

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide - influenza A
    pandemic 2009 forward

<400> SEQUENCE: 39
ttgcagtagc aagtgggcat ga        22

<210> SEQ ID NO 40
<211> LENGTH: 24
<212> TYPE: DNA

<213> ORGANISM: Artificial Sequence
<220> FEATURE:
<223> OTHER INFORMATION: Synthetic oligonucleotide - influenza A
      pandemic 2009 reverse

<400> SEQUENCE: 40
tcttgtgagc tgggttttca tttg                                          24

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide - influenza B forward

<400> SEQUENCE: 41
tcctcaaytc actcttcgag cg                                            22

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide - influenzaB reverse

<400> SEQUENCE: 42
cggtgctctt gaccaaattg g                                             21

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide - influenza H1
      forward

<400> SEQUENCE: 43
aactactact ggactctrct kgaa                                          24

<210> SEQ ID NO 44
<211> LENGTH: 23
<212> TYPE: DNA
<213> ORGANISM: Artificial Sequence
<220> FEATURE:
<223> OTHER INFORMATION: Synthetic oligonucleotide - influenza H1
      reverse

<400> SEQUENCE: 44
ccattggtgc atttgagktg atg                                           23

<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide - influenza H1
      pandemic 2009 forward

<400> SEQUENCE: 45
gtgctataaa caccagcctc ccatt                                         25

<210> SEQ ID NO 46
<211> LENGTH: 23
<212> TYPE: DNA
<213> ORGANISM: Artificial Sequence
<220> FEATURE:
<223> OTHER INFORMATION: Synthetic oligonucleotide - influenza H1 pandemic 2009 reverse

<400> SEQUENCE: 46
agacgggaya ttcctcaatc ctg                                              23

<210> SEQ ID NO 47
<211> LENGTH: 23
<212> TYPE: DNA
<213> ORGANISM: Artificial Sequence
<220> FEATURE:
<223> OTHER INFORMATION: Synthetic oligonucleotide - influenza North
      American H7 forward

<400> SEQUENCE: 47
aaatgcacaa ggagagggaa ctg                                              23

<210> SEQ ID NO 48
<211> LENGTH: 23
<212> TYPE: DNA
<213> ORGANISM: Artificial Sequence
<220> FEATURE:
<223> OTHER INFORMATION: Synthetic oligonucleotide - influenza North
      American H7 reverse

<400> SEQUENCE: 48
cattgcyacy aasagytcag crt                                              23

<210> SEQ ID NO 49
<211> LENGTH: 26
<212> TYPE: DNA
<213> ORGANISM: Artificial Sequence
<220> FEATURE:
<223> OTHER INFORMATION: Synthetic oligonucleotide - influenza H9
      forward

<400> SEQUENCE: 49
caagctggaa tctgarggaa cttaca                                           26

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide - influenza H9
      reverse

<400> SEQUENCE: 50
gcatctgcaa gatccattgg acat                                             24

<210> SEQ ID NO 51
<211> LENGTH: 19
<212> TYPE: DNA
<213> ORGANISM: Artificial Sequence
<220> FEATURE:
<223> OTHER INFORMATION: Synthetic oligonucleotide - human RNase P
      forward

<400> SEQUENCE: 51
agatttggac ctgcgagcg                                                   19

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide - human RNase P
      reverse

<400> SEQUENCE: 52
gagcggctgt ctccacaagt                                                    20

<210> SEQ ID NO 53
<211> LENGTH: 240
<212> TYPE: DNA
<213> ORGANISM: Influenza A virus

<400> SEQUENCE: 53
aacggttgtt tcgagttcta tcataaatgt gataatgaat gtatggaaag tgtaagaaat        60
ggaacgtatg actacccgca gtattcagaa gaagcgagac taaaaagaga ggaaataagt       120
ggagtaaaat tggaatcaat aggaatttac caaatactgt caatttattc tacagtggcg       180
agttccctag cactggcaat catggtagct ggtctatcct tatggatgtg ctccaatggg       240

<210> SEQ ID NO 54
<211> LENGTH: 240
<212> TYPE: DNA
<213> ORGANISM: Influenza A virus

<400> SEQUENCE: 54
aacggttgtt tcgagttcta tcacaaatgt gataatgaat gcatggaaag tgtgagaaac 60
gggacatatg actacccgca gtattcagaa gaagcaagat taaaaagaga ggagataagt 120
ggagtgaaat tggaatcgat aggagtttac caaatactgt caatttattc tacagtggcg 180
agttccctag cactggcaat catggtagct ggtctatcct tatggatgtg ctccaatggg 240

<210> SEQ ID NO 55
<211> LENGTH: 240
<212> TYPE: DNA
<213> ORGANISM: Influenza A virus

<400> SEQUENCE: 55
aacggttgtt tcgagttcta tcacaaatgt gataatgaat gtatggaaag tataagaaac 60
ggaacgtaca actatccgca gtattcagaa gaagcaagat taaaaagaga ggaaataagt 120
ggggtaaaat tggaatcaat aggaacttac caaatactgt caatttattc aacagtggcg 180
agttccctag cactggcaat catgatggct ggtctatctt tatggatgtg ctccaatgga 240

<210> SEQ ID NO 56
<211> LENGTH: 240
<212> TYPE: DNA
<213> ORGANISM: Influenza A virus

<400> SEQUENCE: 56
aacggttgtt tcgagttcta tcacaaatgt gataatgaat gtatggaaag tataaggaac 60
ggaacataca actatccgca gtattcagaa gaagcaagat taaaaagaga ggaaataagt 120
ggggtaaaat tagaatcaat aggaacttac caaatactgt caatttactc aacagtggcg 180
agttccctag cactggcaat catgatagct ggtctatctt tatggatgtg ctccaatgga 240

<210> SEQ ID NO 57
<211> LENGTH: 240
<212> TYPE: DNA
<213> ORGANISM: Influenza A virus

<400> SEQUENCE: 57
aacggttgtt tcgagttcta tcacaaatgt gataatgaat gtatggaaag tataaggaac 60

```
ggaacataca actatccgca gtattcagaa gaagcaagat taaaaagaga ggaaataagt ggaacgtatg actacccgca gtactcagaa gaagcaagat taaaaagaga ggaaataagt    120
ggagtaaaat tggaatcgat aggaacttac caaatactgt caatttattc aacagtggcg    180
agttccctag tacttgcaat catagtggct ggtctatctt tatggatgtg ttccaacggt    240

<210> SEQ ID NO 63
<211> LENGTH: 240
<212> TYPE: DNA
<213> ORGANISM: Influenza A virus

<400> SEQUENCE: 63
aacggttgtt tcgagttcta tcacaaatgt aataatgaat gtatggaaag tgtaagaaac     60
ggaacgtatg actacccgca gtattcagaa gaagcaagat taaaaagaga ggaaataagt    120
ggagtaaaat tggaatcaat aggaatttac caaatactgt caatttattc aacagtggcg    180
agttccctag tactggcaat catgatggct ggtctatctt tatggatgtg ttccaacggg    240

<210> SEQ ID NO 64
<211> LENGTH: 240
<212> TYPE: DNA
<213> ORGANISM: Influenza A virus

<400> SEQUENCE: 64
aacggttgtt tcgagttcta tcacaaatgt aatgatgaat gtatggaaag tgtaagaaac     60
ggaacgtatg actacccgca gtattcagaa gaagcaagat taaaaagaga agaaataagt    120
ggagtaaagt tggaatcaat aggaatttac caaatattgt caatttattc aacagtggcg    180
agttccctag tactggcaat catgatggct ggtctatctt tatggatgtg ttccaacggg    240

<210> SEQ ID NO 65
<211> LENGTH: 200
<212> TYPE: DNA
<213> ORGANISM: Influenza A virus

<400> SEQUENCE: 65
aacggttgct tcgagttcta tcacaaatgt gataatgaat gtatggaaag tgtaagaaac     60
ggaacgtatg actacccgca gtattcagaa gaagcaagat taaaaagaga ggaaattagt    120
ggagtaaaat tggaatcaat aggaacttac caaatactgt caatttattc aacagttgcg    180
agttctctag cgctggcaat                                                 200

<210> SEQ ID NO 66
<211> LENGTH: 200
<212> TYPE: DNA
<213> ORGANISM: Influenza A virus

<400> SEQUENCE: 66
aacggttgct tcgagttcta tcacagatgt gataatgaat gtatggaaag tgtaaggaac     60
ggaacgtatg actacccgca gtattcagaa gaagcaagat taaaaagaga ggaaattagt    120
ggagtaaaat tggaatcaat aggaacttac caaatactgt caatttattc aacagttgcg    180
agttcactag tgctggcaat                                                 200

<210> SEQ ID NO 67
<211> LENGTH: 240
<212> TYPE: DNA
<213> ORGANISM: Influenza A virus

<400> SEQUENCE: 67

```
aacggttgtt ttgagttcta tcacaaatgt gataatgaat gcatggaaag tgtaagaaac      60
ggaacgtatg actacccgca gtattcagaa gaagcaagat taaaaagaga ggaaataagt     120
ggagtaaaat tggaatcaat aggaacttac caaatactgt caatttattc aacagttgca     180
agttccctag cactggcaat catggtggct ggtctatctt tatggatgtg ctccaatggg     240
```

<210> SEQ ID NO 68
<211> LENGTH: 200
<212> TYPE: DNA
<213> ORGANISM: Influenza A virus

<400> SEQUENCE: 68

```
aacggttgtt tcgagttcta tcacaaatgt gataatgaat gcatggaaag tgtaagaaac      60
ggaacgtatg actacccgca gtattcagaa gaagcaagat taaaaagaga ggaaataagt     120
ggagtaaaat tggaatcaat aggaacttac caaatactgt caatttattc aacagctgcg     180
agttctctag cactggcaat                                                  200
```

<210> SEQ ID NO 69
<211> LENGTH: 200
<212> TYPE: DNA
<213> ORGANISM: Influenza A virus

<400> SEQUENCE: 69

```
aacggttgtt tcgagttcta tcacaaatgt gataatgaat gcatggaaag tgtaagaaac      60
ggaacatatg actacccgca gtattcagaa gaagcaagat taaaaagaga agaaataagt     120
ggagtaaaat tggaatcaat aggaacgtac caaatactgt caatttattc aacagttgcg     180
agttctctag cactggcaat                                                  200
```

<210> SEQ ID NO 70
<211> LENGTH: 240
<212> TYPE: DNA
<213> ORGANISM: Influenza A virus

<400> SEQUENCE: 70

```
aacggttgtt tcgagttcta tcacaaatgt gataatgaat gcatggaaag tgtaagaaac      60
ggaacatatg actacccgca gtattcagaa gaagcaagat taaaaagaga agaaataagt     120
ggagtaaaat tggaatcaat aggaacgtac caaatactgt caatttattc aacagttgcg     180
agttctctag cactggcaat catggtggct ggtctatctt tatggatgtg ctccaatggg     240
```

<210> SEQ ID NO 71
<211> LENGTH: 240
<212> TYPE: DNA
<213> ORGANISM: Influenza A virus

<400> SEQUENCE: 71

```
aacggttgtt tcgagttcta tcacaaatgt gataatgaat gcatggaaag tgtaagaaac      60
ggaacgtatg actacccgca gtactcagaa gaagcaagat taaaaagaga ggaaataagt     120
ggagtaagat tggaatcaat aggaacttac caaatactgt caatttactc aacagttgcg     180
agttctttag cactggcaat catgatggct ggtctatctt tatggatgtg ctccaatggg     240
```

<210> SEQ ID NO 72
<211> LENGTH: 228
<212> TYPE: DNA
<213> ORGANISM: Influenza A virus

<400> SEQUENCE: 72

-continued aacggttgtt tcgagttcta tcacaaatgt gatgatgaat gtatggaaag tgtaaaaaac 60
ggaacgtatg actacccgca gtattcagaa gaagctagac taaacagaga ggagataaat 120
ggagtaaaat tggaatcaat gggaacttac caaatactgt caatttactc aacagtggcg 180
agttccctag cactggcaat catggtagct ggtctatctt tatggatg 228

<210> SEQ ID NO 73
<211> LENGTH: 240
<212> TYPE: DNA
<213> ORGANISM: Influenza A virus

<400> SEQUENCE: 73
aacggttgtt tcgagttcta ccacaaatgt gataatgaat gtatggaaag tgtaagaaac 60
ggaacgtatg actactcgca gtattcagaa gaagcaagac taagcagaga ggaaataaat 120
ggagtaaaat tggaatcaat ggtaacttac caaatactgt caatttattc aacagtggcg 180
agttccctag cattggcaat catggtggct ggtctatctt tatggatgtg ctccaatgga 240

<210> SEQ ID NO 74
<211> LENGTH: 200
<212> TYPE: DNA
<213> ORGANISM: Influenza A virus

<400> SEQUENCE: 74
aacggttgtt tcgagttcta ccacaaatgt gataatgaat gtatggaaag tgtaaaaaac 60
gggacgtatg actacccgca gtattcagaa gaagcaagac taaacagaga ggaaataagt 120
ggagtaaaat tggaatcaat tgtaacttac caaatactgt caatttattc aacagtggcg 180
agttccctag cattggcaat 200

<210> SEQ ID NO 75
<211> LENGTH: 320
<212> TYPE: DNA
<213> ORGANISM: Influenza A virus

<400> SEQUENCE: 75
gtcaaactcc aatgggggcg ataaactcta gcatgccatt ccacaatata caccctctca 60
ccattgggga atgccccaaa tatgtgaaat caaacagatt agtccttgcg actgggctca 120
gaaatagccc tcaaagagag agaagaagaa aaaagagagg attatttgga gctatagcag 180
gttttataga gggaggatgg cagggaatgg tagatggttg gtatgggtac caccatagca 240
atgagcaggg gagtgggtac gctgcagaca aagaatccac tcaaaaggca atagatggag 300
tcaccaataa ggtcaactcg 320

<210> SEQ ID NO 76
<211> LENGTH: 320
<212> TYPE: DNA
<213> ORGANISM: Influenza A virus

<400> SEQUENCE: 76
gtcaaactcc aatgggggcg ataaactcta gtatgccatt ccacaatata catcctctca 60
ctattgggga atgccccaaa tatgtgaaat cagacagact agtacttgcg accgggctca 120
gaaatagccc tcaaagagag ggaagaagaa aaaagagagg gttatttgga gctatagcag 180
gttttataga gggaggatgg caggggatgg tagatggttg gtatgggtac caccatagca 240
atgagcaggg aagcgggtac gctgcagaca aagaatccac tcaaaaggct atagatggag 300

```
tcaccaataa ggtcaactcg                                               320
```

<210> SEQ ID NO 77
<211> LENGTH: 320
<212> TYPE: DNA
<213> ORGANISM: Influenza A virus

<400> SEQUENCE: 77

```
gtcaaactcc aatgggggcg ataaactcta gtatgccatt ccacaacata caccctctca    60
ccatcgggga atgccccaaa tatgtgaaat caaacagatt agtccttgca cagggctca   120
gaaatagccc tcaaagagag agcagaagaa aaaagagagg actatttgga gctatagcag   180
gttttataga gggaggatgg cagggaatgg tagatggttg gtatgggtac caccatagca   240
atgagcaggg gagtgggtac gctgcagaca agaatccac tcaaaaggca atagatggag    300
tcaccaataa ggtcaactca                                               320
```

<210> SEQ ID NO 78
<211> LENGTH: 320
<212> TYPE: DNA
<213> ORGANISM: Influenza A virus

<400> SEQUENCE: 78

```
gtcaaactcc aatagggcg ataaactcta gtatgccatt ccacaacatc caccctctca    60
ccatcgggga atgccccaaa tatgtgaaat caaacagatt agtccttgcg actgggctca   120
gaaatagccc tcaaggagag agaagaagaa aaaagagagg actatttgga gctatagcag   180
gttttataga gggaggatgg cagggaatgg tagatggttg gtatgggtac caccatagca   240
acgagcaggg gagtgggtac gctgcagaca agaatccac tcaaaaggca atagatggag    300
tcaccaataa ggtcaactcg                                               320
```

<210> SEQ ID NO 79
<211> LENGTH: 320
<212> TYPE: DNA
<213> ORGANISM: Influenza A virus

<400> SEQUENCE: 79

```
gtcaaactcc aatagggcg ataaactcca gtatgccatt ccacaacatc caccctctca    60
ccatcgggga atgccccaaa tatgtgaaat caaacagatt agtccttgct actgggctca   120
gaaatagccc tcaaggagag agaagaagaa aaaagagagg actatttgga gctatagcag   180
gttttataga gggaggatgg cagggaatgg tagatggttg gtatgggtac caccatagta   240
acgagcaggg gagtgggtac gctgcagaca agaatccac tcaaaaggca atagatggag    300
tcaccaataa ggtcaactcg                                               320
```

<210> SEQ ID NO 80
<211> LENGTH: 317
<212> TYPE: DNA
<213> ORGANISM: Influenza A virus

<400> SEQUENCE: 80

```
gtcagactcc gatggggcg ataaactcta gtatgccatt ccacaacata caccctctca    60
ccataggaga atgtcccaaa tatgtgaaat caaacaaatt agtccttgcg actgggctca   120
gaaatagtcc tcaaagagag agaagaagaa aaagaggact gtttggagct atagcaggtt   180
ttataggg aggatggcag ggaatggtag atggttggta tgggtaccac cacagcaatg   240
agcaggggag tggatatgct gcagacaaag aatccactca aaaggcaata gacggagtca    300
```

```
ccaataaggt caactcg                                                  317
```

<210> SEQ ID NO 81
<211> LENGTH: 320
<212> TYPE: DNA
<213> ORGANISM: Influenza A virus

<400> SEQUENCE: 81

```
gtcagactcc gatgggggcg ataaattcta gtatgccatt ccacaacata caccctctca    60
ccatcggaga atgtcccaaa tatgtgaaat caaacaaatt agtccttgcg actgggctca   120
gaaatagtcc tcaaatagag agaagaagaa gaaaaagggg actgtttgga gctatagcag   180
gttttataga gggaggatgg cagggaatgg tagatggttg gtatgggtac catcacagca   240
atgagcaggg gagtgggtat gctgcagaca agaatccac tcaaaaggca atagatgggg    300
tcaccaataa agtcaactcg                                               320
```

<210> SEQ ID NO 82
<211> LENGTH: 320
<212> TYPE: DNA
<213> ORGANISM: Influenza A virus

<400> SEQUENCE: 82

```
gtcagactcc gatgggggcg ataaattcta gtatgccatt ccacaacata caccctctca    60
ccatcggaga atgccccaaa tatgtgaaat caaacaaatt agtccttgcg actgggctca   120
gaaatagtcc tcaaatagag agaagaagaa gaaaaagggg actgtttgga gctatagcag   180
gttttataga gggaggatgg cagggaatgg tagatggttg gtatgggtac catcacagca   240
atgagcaggg gagtggatac gctgcagaca agaatccac tcaaaaggca atagatgggg    300
tcaccaataa agtcaactcg                                               320
```

<210> SEQ ID NO 83
<211> LENGTH: 317
<212> TYPE: DNA
<213> ORGANISM: Influenza A virus

<400> SEQUENCE: 83

```
gtcagactcc gatagggggcg ataaactcca gtatgccatt ccacaacata caccctctca   60
ccatcggaga atgtcccaaa tatgtgaaat caaacaaact agtccttgcg actgggctca   120
gaaatagtcc tcaaagagag agaagaagaa aaagaggatt gtttggagct atagcaggtt   180
ttatagaggg aggatggcag ggaatggtag atggttggta tgggtaccac cacagcaatg   240
agcaggggag tgggtacgct gcagacaaag aatctactca aaaggcaata gacggagtca   300
ccaataaggt caactcg                                                  317
```

<210> SEQ ID NO 84
<211> LENGTH: 317
<212> TYPE: DNA
<213> ORGANISM: Influenza A virus

<400> SEQUENCE: 84

```
gtcagactcc tatggggcg ataaactcta gtatgccatt ccacaacata catccctca     60
ccatcggaga atgtcccaaa tatgtgaaat caaacaaatt agtccttgcg actgggctca   120
gaaatagtcc tcaaagagag agaagaagaa aaagaggatt gtttggagct atagcagggt   180
ttatagaggg aggatggcag ggaatggtag atggttggta tgggtaccac cacagcaacg   240
```
agcaggggag tgggtacgct gcagacaaag aatctactca aaaggcaata gacggagtca 300
ccaataaggt caactcg 317

<210> SEQ ID NO 85
<211> LENGTH: 317
<212> TYPE: DNA
<213> ORGANISM: Influenza A virus

<400> SEQUENCE: 85
gtcaaactcc gatagggggcg ataaactcta gtatgccatt ccacaatata caccctctca 60
ccatcgggga atgccccaaa tatgtgaaat caaacaaatt agtccttgcg actgggctca 120
gaaatagtcc tctaagagaa aggagaagaa aaagaggact atttggagct atagcagggt 180
ttatagaggg aggatggcag ggaatggtag atggttggta tgggtaccac caaagtaatg 240
agcaggggag tgggtacgct gcagacaaag aatccaccca aaaggcaata gatggagtta 300
ccaataaggt caactct 317

<210> SEQ ID NO 86
<211> LENGTH: 293
<212> TYPE: DNA
<213> ORGANISM: Influenza A virus

<400> SEQUENCE: 86
gtcaaactcc aatagggggcg ataaactcta gtatgccatt ccacaatata caccctctca 60
ccatcgggga atgccccaaa tatgtgaaat caaacaaatt agtccttgcg actgggctca 120
gaaatagtcc tcgactattt ggagctatag cagggtttat agagggagga tggcagggaa 180
tggtagatgg ttggtatggg taccaccaaa gtaatgagca ggggagtggg tacgctgcag 240
acagagaatc cacccaaaag gcaatagatg gagtcaccaa taaggtcaac tct 293

<210> SEQ ID NO 87
<211> LENGTH: 317
<212> TYPE: DNA
<213> ORGANISM: Influenza A virus

<400> SEQUENCE: 87
gtcaaactcc agtagggggcg ataaactcta gtatgccatt ccacaacata caccatctca 60
ctatcgggga atgccccaaa tatgtgaaat caaacaaatt agtccttgcg actgggctca 120
ggaatagtgc tctaagagaa aaaagaagaa aaagaggact atttggagct atagcaggtt 180
ttatagaggg aggatggcag ggaatggtag atggttggta tgggtaccac catagcaatg 240
agcaggggag tgggtatgct gcagacaaag aatccactca aaaggcaata gatggagtca 300
ccaataaggt caactcg 317

<210> SEQ ID NO 88
<211> LENGTH: 317
<212> TYPE: DNA
<213> ORGANISM: Influenza A virus

<400> SEQUENCE: 88
gtcaaactcc aatagggggcg ataaactcta gtatgccatt ccacaacata caccctctca 60
ccatcgggga atgccccaaa tatgtgaaat caaacaaatt agtccttgcg actgggctca 120
gaaatagtcc tctaagagaa agaagaagaa aaagaggact atttggagct atagcaggtt 180
ttatagaggg cggatggcag ggaatggtag atggttggta tgggtttcac catagcaatg 240
agcaggggag tgggtatgct gcagacaaag aatccactca aaaggcaata gatggagtca 300

```
ccaataaggt caactca                                                  317

<210> SEQ ID NO 89
<211> LENGTH: 320
<212> TYPE: DNA
<213> ORGANISM: Influenza A virus

<400> SEQUENCE: 89
gtcaaactcc aatgggggcg ataaactcta gtatgccatt ccacaacata caccctctca     60
ccatcgggga atgccccaaa tatgtgaaat caaacagatt agtccttgca actggactca    120
gaaatacgcc tcaaagagag agaaggagaa aaaagagagg actatttgga gccatagcag    180
gttttattga gggaggatgg cagggaatgg tagacggttg gtatgggtac caccatagca    240
atgagcaggg gagtggatac gctgcagaca aagaatccac tcaaaaggca atagatggaa    300
tcaccaataa ggtcaactcg                                                320

<210> SEQ ID NO 90
<211> LENGTH: 320
<212> TYPE: DNA
<213> ORGANISM: Influenza A virus

<400> SEQUENCE: 90
gtcaaactcc aatgggggcg ataaattcta gtatgccatt ccacaacata caccctctca     60
ccatcgggga atgccccaaa tatgtgaagt caaacagatt agtcctcgc

```
<212> TYPE: DNA
<213> ORGANISM: Artificial Sequence
<220> FEATURE:
<223> OTHER INFORMATION: Synthetic oligonucleotide - influenza H3
      reverse

<400> SEQUENCE: 93
attgcrccra atatgcctct agt                                          23

<210> SEQ ID NO 94
<211> LENGTH: 27
<212> TYPE: DNA
<213> ORGANISM: Artificial Sequence
<220> FEATURE:
<223> OTHER INFORMATION: Synthetic oligonucleotide - influenza H3 probe

<400> SEQUENCE: 94
caggatcaca tatgggscct gtcccag                                      27

<210> SEQ ID NO 95
<211> LENGTH: 24
<212> TYPE: DNA
<213> ORGANISM: Artificial Sequence
<220> FEATURE:
<223> OTHER INFORMATION: Synthetic oligonucleotide - influenza H5a
      forward

<400> SEQUENCE: 95
tggaaagtrt aaraaacgga acgt                                         24

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide - influenza H5a
      reverse

<400> SEQUENCE: 96
ygctagggar ctcgccactg                                              20

<210> SEQ ID NO 97
<211> LENGTH: 35
<212> TYPE: DNA
<213> ORGANISM: Artificial Sequence
<220> FEATURE:
<223> OTHER INFORMATION: Synthetic oligonucleotide - influenza H5a probe

<400> SEQUENCE: 97
tgactacccg cagtattcag aagaagcaag actaa                             35

<210> SEQ ID NO 98
<211> LENGTH: 26
<212> TYPE: DNA
<213> ORGANISM: Artificial Sequence
<220> FEATURE:
<223> OTHER INFORMATION: Synthetic oligonucleotide - influenza H5b
      forward

<400> SEQUENCE: 98
ggaatgyccc aaatatgtga aatcaa                                       26

<210> SEQ ID NO 99
<211> LENGTH: 20
<212> TYPE: DNA
<213> ORGANISM: Artificial Sequence
<220> FEATURE:
```

<223> OTHER INFORMATION: Synthetic oligonucleotide - influenza H5b
      reverse

<400> SEQUENCE: 99
ccactcccct gctcrttgct                                                     20

<210> SEQ ID NO 100
<211> LENGTH: 33
<212> TYPE: DNA
<213> ORGANISM: Artificial Sequence
<220> FEATURE:
<223> OTHER INFORMATION: Synthetic oligonucleotide - influenza H5b probe

<400> SEQUENCE: 100
tacccatacc aaccatctac cattccctgc cat                                      33

<210> SEQ ID NO 101
<211> LENGTH: 25
<212> TYPE: DNA
<213> ORGANISM: Artificial Sequence
<220> FEATURE:
<223> OTHER INFORMATION: Synthetic oligonucleotide - influenza Eurasian
      H7 forward

<400> SEQUENCE: 101
gcttcaggca tcaaaatgca caagg                                               25

<210> SEQ ID NO 102
<211> LENGTH: 23
<212> TYPE: DNA
<213> ORGANISM: Artificial Sequence
<220> FEATURE:
<223> OTHER INFORMATION: Synthetic oligonucleotide - influenza Eurasian
      H7 reverse

<400> SEQUENCE: 102
cattgctacy aagagttcag crt                                                 23

<210> SEQ ID NO 103
<211> LENGTH: 31
<212> TYPE: DNA
<213> ORGANISM: Artificial Sequence
<220> FEATURE:
<223> OTHER INFORMATION: Synthetic oligonucleotide - influenza Eurasian
      probe

<400> SEQUENCE: 103
accacacttc tgtcatggaa tctctggtcc a                                        31

<210> SEQ ID NO 104
<211> LENGTH: 24
<212> TYPE: DNA
<213> ORGANISM: Artificial Sequence
<220> FEATURE:
<223> OTHER INFORMATION: Synthetic oligonucleotide - influenza North
      American H7 forward

<400> SEQUENCE: 104
aaaygcacaa ggagarggaa ctgc                                                24

<210> SEQ ID NO 105
<211> LENGTH: 27
<212> TYPE: DNA
<213> ORGANISM: Artificial Sequence
<220> FEATURE:
<223> OTHER INFORMATION: Synthetic oligonucleotide - influenza North
      American H7 reverse

<400> SEQUENCE: 105
gcattrtacg accatayctc agtcatt 27

<210> SEQ ID NO 106
<211> LENGTH: 34
<212> TYPE: DNA
<213> ORGANISM: Artificial Sequence
<220> FEATURE:
<223> OTHER INFORMATION: Synthetic oligonucleotide - influenza North American H7 probe

<400> SEQUENCE: 106
aaagcacyca rtctgcaata gatcagatca cagg 34

<210> SEQ ID NO 107
<211> LENGTH: 23
<212> TYPE: DNA
<213> ORGANISM: Artificial Sequence
<220> FEATURE:
<223> OTHER INFORMATION: Synthetic oligonucleotide - influenza H9 forward

<400> SEQUENCE: 107
ctggartctg arggractta caa 23

<210> SEQ ID NO 108
<211> LENGTH: 22
<212> TYPE: DNA
<213> ORGANISM: Artificial Sequence
<220> FEATURE:
<223> OTHER INFORMATION: Synthetic oligonucleotide - influenza H9 reverse

<400> SEQUENCE: 108
aaraaggcag caaaccccat tg 22

<210> SEQ ID NO 109
<211> LENGTH: 30
<212> TYPE: DNA
<213> ORGANISM: Artificial Sequence
<220> FEATURE:
<223> OTHER INFORMATION: Synthetic oligonucleotide - influenza H9 probe

<400> SEQUENCE: 109
cyatttattc ractgtcgcc tcatctcttg 30

<210> SEQ ID NO 110
<211> LENGTH: 240
<212> TYPE: DNA
<213> ORGANISM: Influenza A virus

<400> SEQUENCE: 110
aaaatgcaca aggagaagga actgcagctg actacaaaag cacccaatct gcaatagatc 60
agatcacagg caaattgaat cgtctaattg acaaaacaaa tcagcagttt aaactgatag 120
acaatgaatt cagtgaaata gagcaacaaa ttgggaatgt cattaactgg acacgagact 180
caatgactga ggtatggtcg tacaatgctg aattgctggt agcaatggaa aatcagcaca 240

<210> SEQ ID NO 111
<211> LENGTH: 240
<212> TYPE: DNA
<213> ORGANISM: Influenza A virus

<400> SEQUENCE: 111

```
aaaatgcaca aggagaagga actgcagctg attacaaaag cactcaatct gcgatagatc    60
agatcacagg caaattgaat cgtctaattg acaaaacaaa tcagcagttt gaactgatag   120
acaacgaatt cagtgaaata gaacaacaaa ttgggaatgt cattaactgg acacgagatt   180
caatgactga ggtatggtcg tacaatgctg aattgctggt agctatggaa aatcagcaca   240
```

<210> SEQ ID NO 112
<211> LENGTH: 240
<212> TYPE: DNA
<213> ORGANISM: Influenza A virus

<400> SEQUENCE: 112

```
aaaatgcaca aggagaagga actgcagctg attacaaaag cactcaatct gcaatagacc    60
agatcacagg caaattgaat cgtctaatcg acaaaacaaa tcagcagttt gaactgatag   120
acaacgaatt cagtgaaata gaacaacaaa ttgggaatgt cattaactgg acacgagatt   180
caatgactga gatatggtcg tacaatgctg aattgctggt agctatggaa aatcagcaca   240
```

<210> SEQ ID NO 113
<211> LENGTH: 240
<212> TYPE: DNA
<213> ORGANISM: Influenza A virus

<400> SEQUENCE: 113

```
aaaatgcaca aggagaagga actgcagctg attacaaaag cactcaatct gcaatagacc    60
agatcacagg caaattgaat cgtctaatcg acaaaacaaa tcagcagttt gaactgatag   120
acaacgaatt cagtgaaata gaacaacaaa ttgggaatgt cattaactgg acacgagatt   180
caatgactga gatatggtcg tacaatgctg aattgctggt agctatggaa aatcagcaca   240
```

<210> SEQ ID NO 114
<211> LENGTH: 240
<212> TYPE: DNA
<213> ORGANISM: Influenza A virus

<400> SEQUENCE: 114

```
aaaatgcaca agggaagga actgcagctg actacaaaag cactcaatct gcaatagatc    60
agatcacaag caaattgaat cgtctaattg acaaaacaaa tcagcagttt gaactgatag   120
acaacgaatt cagtgaaata gaacaacaaa ttgggaatgt cattaactgg acacgagact   180
caatgactga ggtatggtcg tacaatgctg aattgctggt agcaatggaa aatcagcata   240
```

<210> SEQ ID NO 115
<211> LENGTH: 240
<212> TYPE: DNA
<213> ORGANISM: Influenza A virus

<400> SEQUENCE: 115

```
aaaatgcaca aggagaggga actgcagctg actacaaaag cacccagtct gcaatagatc    60
agatcacagg caaattgaat cgtttaattg gcaaaacaaa tcagcagttt gagctgatag   120
acaatgagtt caatgagata gaacaacaaa taggaaatgt cattaattgg acaagagacg   180
caatgactga gatatggtcg tataatgctg agctcttggt ggcaatggaa aatcagcata   240
```

<210> SEQ ID NO 116
<211> LENGTH: 152
<212> TYPE: DNA
<213> ORGANISM: Influenza A virus

```
<400> SEQUENCE: 116
aaggcagaaa atagaaggga taaagctgga gtctgagggg acttacaaaa tcctcactat      60
ttattcgact gtcgcctcat ctcttgtact tgcaatgggg tttgctgcct tcttgttctg     120
ggccatgtct aatggatcat gcaggtgcaa ca                                   152

<210> SEQ ID NO 117
<211> LENGTH: 152
<212> TYPE: DNA
<213> ORGANISM: Influenza A virus

<400> SEQUENCE: 117
gaggcagaaa atagaaggga taaagctgga gtctgagggg acttacaaaa tcctcactat     60
ttattcgact gtcgcctcat ctcttgtact tgcaatgggg tttgctgcct tcttgttctg    120
ggccatgtct aatggatcat gcaggtgcaa ca                                  152

<210> SEQ ID NO 118
<211> LENGTH: 136
<212> TYPE: DNA
<213> ORGANISM: Influenza A virus

<400> SEQUENCE: 118
ggggtgaaac tggaatctga ggggacttac aagatcctca ccatttattc gactgtcgcc     60
tcatctcttg tgcttgcaat ggggtttgct gcctttttat tctgggccat gtccaatgga   120
tcttgcagat gcaaca                                                    136

<210> SEQ ID NO 119
<211> LENGTH: 152
<212> TYPE: DNA
<213> ORGANISM: Influenza A virus

<400> SEQUENCE: 119
aagacagaaa atagaggggg tcaagctgga atctgaagga acttacaaaa tcctcaccat     60
ttattcgact gtcgcctcat ctattgtgat tgcaatgggg tttgctgcct ttttattctg   120
ggccatgtcc aatgggtctt gcagatgcaa ca                                  152

<210> SEQ ID NO 120
<211> LENGTH: 136
<212> TYPE: DNA
<213> ORGANISM: Influenza A virus

<400> SEQUENCE: 120
ggggtgaaac tggaatctga gggaacttac aagatcctca ccatttattc gactgtcgcc     60
tcatctcttg tgattgcaat ggggtttgct gccttttat tctgggccat gtccaatgga    120
tcttgcagat gcaaca                                                    136

<210> SEQ ID NO 121
<211> LENGTH: 137
<212> TYPE: DNA
<213> ORGANISM: Influenza A virus

<400> SEQUENCE: 121
aagacagaaa atagaggggg tcaagctgga atctgaagga acttacaaaa tcctcaccat     60
ttattcgact gtcgcctcat ctcttgtgat tgcaatgggg tttgctgcct tcttgttctg   120
ggccatgtcc aatgggt                                                   137
```

```
<210> SEQ ID NO 122
<211> LENGTH: 152
<212> TYPE: DNA
<213> ORGANISM: Influenza A virus

<400> SEQUENCE: 122
acggcagaaa atagaagggg tcaagctaga atctgaggga acttacagaa tccttaccat      60
ttattcgacc gtcgcctcat ctcttgtgct tgcaataggg tttgctgcct tcttattctg     120
ggccatgtcc aatgggtctt gcaggtgcaa ca                                   152
```